United States Patent
Mecheri et al.

(10) Patent No.: US 11,642,404 B2
(45) Date of Patent: May 9, 2023

(54) PLASMODIUM WITH HISTAMINE RELEASING FACTOR (HRF) DEFICIENCY FOR USE AS A VACCINE

(71) Applicants: INSTITUT PASTEUR, Paris (FR); INSTITUT NATIONAL DE LA SANTE ET DE LA RECHERCHE MEDICALE, Paris (FR)

(72) Inventors: Salah Mecheri, Fontenay-le-fleury (FR); Robert Menard, Clamart (FR); Claudia Demarta-Gatsi, Paris (FR)

(73) Assignees: INSTITUT PASTEUR, Paris (FR); INSTITUT NATIONAL DE LA SANTE ET DE LA RECHERCHE MEDICALE, Paris (FR)

(*) Notice: Subject to any disclaimer, the term of this patent is extended or adjusted under 35 U.S.C. 154(b) by 0 days.

(21) Appl. No.: 17/151,516

(22) Filed: Jan. 18, 2021

(65) Prior Publication Data
US 2021/0393760 A1    Dec. 23, 2021

Related U.S. Application Data

(62) Division of application No. 16/318,365, filed as application No. PCT/IB2017/001096 on Jul. 18, 2017, now Pat. No. 10,898,564.

(60) Provisional application No. 62/363,686, filed on Jul. 18, 2016.

(51) Int. Cl.
| | |
|---|---|
| *A61K 39/002* | (2006.01) |
| *A61K 39/015* | (2006.01) |
| *A61P 33/06* | (2006.01) |
| *A61K 35/68* | (2006.01) |
| *C07K 16/20* | (2006.01) |
| *G01N 33/569* | (2006.01) |
| *A61K 39/00* | (2006.01) |

(52) U.S. Cl.
CPC ............ *A61K 39/015* (2013.01); *A61K 35/68* (2013.01); *A61P 33/06* (2018.01); *C07K 16/205* (2013.01); *G01N 33/56905* (2013.01); *A61K 2039/5254* (2013.01); *G01N 2333/445* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 10,898,564 B2 | 1/2021 | Mecheri et al. | |
| 2014/0154289 A1* | 6/2014 | Vaquero | A61K 39/015 424/272.1 |

OTHER PUBLICATIONS

Demarta-Gatsi, "Protection against malaria is induced by blood stage-arresting Histamine Releasing Factor (HRF)-deficient Plasmodium parasites,"—Research Institut Pasteur Event, https://research.pasteur.fr/en/event/protection-against-malaria-is-induced-by-blood-stage-arresting-histamine-releasing-factor-hrf-deficient-plasmodium-parasites/ (retrieved on Dec. 13, 2017).

Demarta-Gatsi, "Protection against malaria is induced by blood stage-arresting Histamine Releasing Factor (HRF)-deficient Plasmodium parasites," https://research.pasteur.fr/en/member/claudia-demarta-gatsi/ (retrieved on Dec. 13, 2017).

Mathieu et al., "Plasmodium berghei histamine-releasing factor favours liver-stage development via inhibition of IL-6 production and associates with a severe outcome of disease: Malaria parasite HRF controls pathogenicity," Cellular Microbiology, 17(4):542-558 (2014).

Pied et al., "Inhibitory activity of IL-6 on malaria hepatic stages," Parasite Immunology, 13(2):211-217 (1991).

Demarta-Gatsi et al., "Immunological memory to blood-stage malaria infection is controlled by the histamine releasing factor (HRF) of the parasite," Scientific Reports, 7(1):1-14 (2017).

Demarta-Gatsi et al., "Proetection against malaria in mice is induced by blood stage-arresting histamine-releasing factor (HRF)-deficient parasites," the Journal of Experimental Medicine, 213(8):1419-1428 (2016).

International Search Report for PCT/IB2017/001096 dated Dec. 14, 2017 (4 pages).

* cited by examiner

Primary Examiner — Jennifer E Graser
(74) Attorney, Agent, or Firm — Arrigo, Lee, Guttman & Mouta-Bellum LLP

(57) ABSTRACT

A method of generating an antibody and cellular immune response against a *Plasmodium* in a primate, comprising administering at least $10^3$ genetically modified live *Plasmodium* to the primate, wherein the genetically modified live *Plasmodium* is a species selected from *Plasmodium falciparum, Plasmodium vivax, Plasmodium ovale, Plasmodium malariae, Plasmodium knowlesi, Plasmodium coatneyi, Plasmodium cynomolgi*, and *Plasmodium simium*, and wherein the genetically modified live *Plasmodium* does not produce functional histamine releasing factor (HRF) protein, to thereby induce an antibody and cellular immune response against the *Plasmodium* in the primate. In some embodiments at least $10^4$ genetically modified live *Plasmodium* is administered to the primate. An immunogenic composition for administration to a primate, comprising a at least $10^3$ genetically modified live *Plasmodium* wherein the genetically modified live *Plasmodium* is a species selected from *Plasmodium falciparum, Plasmodium vivax, Plasmodium ovale, Plasmodium malariae, Plasmodium knowlesi, Plasmodium coatneyi, Plasmodium cynomolgi*, and *Plasmodium simium*, and wherein the genetically modified live *Plasmodium* does not produce functional histamine releasing factor (HRF) protein; and at least one pharmaceutically acceptable excipient and/or support. In some embodiments the immunogenic composition comprises at least $10^3$ genetically a modified live *Plasmodium*.

15 Claims, 21 Drawing Sheets

Specification includes a Sequence Listing.

PLASMODIUM WITH HISTAMINE RELEASING FACTOR (HRF) DEFICIENCY FOR USE AS A VACCINE

INTRODUCTION

Malaria is an infectious disease caused by a eukaryotic single-cell parasite of the *Plasmodium* genus. This parasitic disease is present throughout the world and causes serious economic and health problems in developing countries. *P. falciparum* is the most harmful species of the five types of *Plasmodium* infecting humans. According to the World Health Organization (WHO), *P. falciparum* is responsible for 250 to 500 million cases of acute disease and approximately one million deaths each year (especially children less than 5 years old and pregnant women). Cerebral malaria is a severe neurological complication of malaria which is responsible for the vast majority of lethal cases of the disease. Even if the individual survives, cerebral malaria can lead to serious neurological after effects, in particular in young children, whose immune system is in the process of forming. The pathogenesis of cerebral malaria is complex and still far from being completely elucidated. At the current time, it is accepted that the cerebral pathology is probably the result of the sequestration of parasitized red blood cells in the microvessels of the main organs (spleen, lungs, heart, intestines, kidneys, liver and brain) and of the production of pro-inflammatorycytokines in these same organs, resulting in a systemic syndrome and state which can lead to the death of the individual.

Combating malaria is one of the major challenges for the WHO but, to date, all efforts aimed at controlling this disease have failed. During the past thirty years, even though WHO figures appear to be encouraging, the situation has worsened because of the occurrence of the resistance of anopheles mosquitoes to insecticides and of the growing chemoresistance of *P. falciparum* to antimalarial drugs (even used in combinations).

Combating malaria is made difficult by the absence of a vaccine which is actually effective against the disease. The first attempts at developing a vaccine go back to the 1970s. Since then, there has been an increasing number of vaccine trials, but the latter are faced with the complexity of the development of the parasite in its two successive hosts, humans and mosquitoes, and also with an extremely complicated mechanism for evading the immune system involving a considerable antigenic variation of the parasite.

This variation during the erythrocytic phase of the parasite makes conventional preventive vaccination using *Plasmodium* protein-peptide complexes extremely difficult. A malaria vaccine produced from proteins of the parasite is currently in phase III of clinical trials (RTS,S from GlaxoSmithKline Biologicals). However, the results obtained during phase II show that this vaccine reduces the occurrence of clinical malaria by only 35% and that of severe malaria by only 49%.

Obtaining a vaccine which is effective against the erythrocytic forms of the parasite is a major challenge in the context of eradication of the disease, given that such a vaccine would make it possible both to reduce the symptoms and also the parasite load and the amount of gametocytes in the blood and therefore to reduce transmission of the parasite.

Live attenuated parasites, in particular genetically attenuated parasites (GAPs), are increasingly considered as vaccines against malaria. Pre-erythrocytic GAPs fail to develop in the liver, whereas blood-stage GAPs cause abortive infections in the blood. In both cases, GAP infection induces solid protection against challenge.

The notion that attenuated blood-stage parasites can confer protection originated in early studies using irradiated parasites (Miyagami et al., 1987; Waki et al., 1982). More recently, it was found that infecting individuals with low doses of *P. falciparum*-infected red blood cells (iRBCs) followed by rapid curative treatment induced strong cell-mediated immunity and durable protection against challenge (Pombo et al., 2002). Subsequently, blood-stage GAPs were generated in rodent parasites, targeting genes involved in the purine salvage pathway in *P. yoelii* (Aly et al., 2010; Ting et al., 2008) or genes encoding a protease involved in hemoglobin degradation (Spaccapelo et al., 2010) and a merozoite surface protein involved in adhesion to RBC (Spaccapelo et al., 2011) in *P. berghei*. These GAPs multiply suboptimally in the blood and cause infections that eventually self-resolve. Notably, abortive GAP-induced infections confer lasting protection against challenge with blood stages or mosquito transmission stages, and depends on both cellular and humoral immunity (Aly et al., 2010; Ting et al., 2008).

Recently, we described the crucial role of histamine releasing factor (HRF), also known as translationally controlled tumour protein (TCTP), during development of *P. berghei* ANKA (PbANKA) in the host liver (Mathieu et al., 2015). In vivo development of HRF-deficient PbANKA parasites is severely impaired in the liver, caused by elevated levels of interleukin 6 (IL-6) (Pied et al., 1991). To test whether HRF might also modulate blood-stage multiplication, we deleted the HRF-encoding gene in *P. berghei* NK65 (PbNK65). PbANKA induces cerebral malaria in susceptible mice, with lesions starting at day 5 post-infection (p.i.) and mice dying from day 7-8 p.i. (Beghdadi et al., 2008), which precludes studies on adaptive immunity. In contrast, PbNK65 does not cause cerebral malaria but hyperparasitemia, leading to mouse death by severe anemia around day 25 p.i. It thus provides an opportunity to track immune responses against blood-stage parasites over a longer period of time.

SUMMARY

In a first aspect, methods of generating an antibody and cellular immune response against a *Plasmodium* in a primate are provided. In some embodiments the methods comprise administering at least $10^3$ genetically modified live *Plasmodium* to the primate to thereby induce an antibody and cellular immune response against the *Plasmodium* in the primate. In some embodiments the genetically modified live *Plasmodium* is a species selected from *Plasmodium falciparum*, *Plasmodium vivax*, *Plasmodium ovale*, *Plasmodium malariae Plasmodium knowlesi*, *Plasmodium coatneyi*, *Plasmodium cynomolgi*, and *Plasmodium simium*. In some embodiments the genetically modified live *Plasmodium* does not produce functional histamine releasing factor (HRF) protein.

In some embodiments of the methods the HRF coding sequence is deleted in the genome of the genetically modified live *Plasmodium*.

In some embodiments of the methods the genetically modified live *Plasmodium* is a *Plasmodium falciparum*.

In some embodiments of the methods the genetically modified live *Plasmodium* does not cause cerebral malaria when administered to the primate.

In some embodiments of the methods the primate is a human.

In some embodiments of the methods the antibody response comprises an IgG3 and IgG1 antibody response that is a protective response equivalent to the antibody response comprising an IgG2c/IgG2a antibody response in mice. In some embodiments the antibody response is detectable by Western blot. In some embodiments the antibody response is detectable by an ELISA assay.

In some embodiments of the methods the cellular immune response comprises phagocytic cells, and preferably FcγR+ CD11b+ phagocytic cells, and more preferably neutrophils.

In some embodiments of the methods, administering the genetically modified live *Plasmodium* induces a decrease of at least 50% in PD1+ spleen cells, and preferably a reduction of at least 50% in PD1+ CD8+ and in PD1+ CD4+ cells in spleen.

In some embodiments of the methods the genetically modified live *Plasmodium* does not produce a functional form of one or more of purine nucleoside phosphorylase, nucleoside transporter 1, UIS3, UIS4, p52, p36, and HMGB2.

In some embodiments of the methods the HMGB2 coding sequence is deleted in the genome of the genetically modified live *Plasmodium*.

In some embodiments of the methods the genetically modified live *Plasmodium* is an intra-erythrocytic form.

In some embodiments of the methods the genetically modified live *Plasmodium* is in the form of intra-erythrocytic trophozoites, merozoites or schizonts.

In some embodiments of the methods the genetically modified live *Plasmodium* is in the form of intra-erythrocytic merozoites or schizonts.

In some embodiments of the methods the genetically modified live *Plasmodium* is in the form of sporozoites.

In some embodiments of the methods the likelihood that the primate will develop *Plasmodium* parasitemia following challenge with a wild type live *Plasmodium* is reduced by at least 75% for a period of at least 68 days following administration of the genetically modified live *Plasmodium*.

In some embodiments of the methods the likelihood that the primate will develop *Plasmodium* parasitemia following challenge with a wild type live *Plasmodium* is reduced by at least 75% for a period of at least 396 days following administration of the genetically modified live *Plasmodium*.

In some embodiments of the methods the likelihood that the primate will develop a blood stage *Plasmodium* infection following challenge with a wild type live *Plasmodium* is reduced by at least 75% for a period of at least 25 days following administration of the genetically modified live *Plasmodium*.

In some embodiments of the methods administering the genetically modified live *Plasmodium* induces an increase of at least 50% in plasma IL-6.

In some embodiments of the methods an infectious dose of at least $10^4$ genetically modified live *Plasmodium* is administered.

In another aspect, immunogenic compositions for administration to a primate are provided. In some embodiments the immunogenic compositions comprise at least $10^3$ genetically modified live *Plasmodium* and at least one pharmaceutically acceptable excipient and/or support. In some embodiments of the immunogenic compositions the genetically modified live *Plasmodium* is a species selected from *Plasmodium falciparum, Plasmodium vivax, Plasmodium ovale, Plasmodium malariae Plasmodium knowlesi, Plasmodium coatneyi, Plasmodium cynomolgi*, and *Plasmodium simium*. In some embodiments of the immunogenic compositions the genetically modified live *Plasmodium* does not produce functional histamine releasing factor (HRF) protein.

In some embodiments of the immunogenic compositions the HRF coding sequence is deleted in the genome of the genetically modified live *Plasmodium*.

In some embodiments of the immunogenic compositions the genetically modified live *Plasmodium* is a *Plasmodium falciparum*.

In some embodiments of the immunogenic compositions the genetically modified live *Plasmodium* does not cause cerebral malaria when administered to the primate.

In some embodiments of the immunogenic compositions the primate is a human.

In some embodiments of the immunogenic compositions, administering the immunogenic composition to the primate generates an antibody and cellular immune response against a *Plasmodium* in the primate. In some embodiments the antibody response in primate comprises an IgG3 and IgG1 antibody response that is a protective response equivalent to the antibody response comprising an IgG2c/IgG2a antibody response in mice. In some embodiments the antibody response is detectable by Western blot. In some embodiments the antibody response is detectable by an ELISA assay.

In some embodiments of the immunogenic compositions administering the immunogenic composition to the primate generates a cellular immune response comprising phagocytic cells, and preferably FcγR+ CD11b+ phagocytic cells, and more preferably neutrophils.

In some embodiments of the immunogenic compositions, administering the immunogenic composition to the primate induces a decrease of at least 50% in PD1+ spleen cells, and preferably a reduction of at least 50% in PD1+ CD8+ and in PD1+ CD4+ cells in spleen.

In some embodiments of the immunogenic compositions the genetically modified live *Plasmodium* does not produce a functional form of one or more of purine nucleoside phosphorylase, nucleoside transporter 1, UIS3, UIS4, p52, p36, and HMGB2.

In some embodiments of the immunogenic compositions the HMGB2 coding sequence is deleted in the genome of the genetically modified live *Plasmodium*.

In some embodiments of the immunogenic compositions the genetically modified live *Plasmodium* is in an intra-erythrocytic form.

In some embodiments of the immunogenic compositions the genetically modified live *Plasmodium* is in the form of intra-erythrocytic trophozoites, merozoites or schizonts.

In some embodiments of the immunogenic compositions the genetically modified live *Plasmodium* is in the form of intra-erythrocytic merozoites or schizonts.

In some embodiments of the immunogenic compositions the genetically modified live *Plasmodium* is in the form of sporozoites.

In some embodiments of the immunogenic compositions administering the immunogenic composition to the primate induces a protective immune response such that the likelihood that the primate will develop *Plasmodium* parasitemia following challenge with a wild type live *Plasmodium* is reduced by at least 75% for a period of at least 68 days following administration of the genetically modified live *Plasmodium*.

In some embodiments of the immunogenic compositions administering the immunogenic composition to the primate induces a protective immune response such that the likelihood that the primate will develop *Plasmodium* parasitemia following challenge with a wild type live *Plasmodium* is reduced by at least 75% for a period of at least 396 days following administration of the genetically modified live *Plasmodium*.

In some embodiments of the immunogenic compositions administering the immunogenic composition to the primate induces a protective immune response such that the likelihood that the primate will develop a blood stage *Plasmodium* infection following challenge with a wild type live *Plasmodium* is reduced by at least 75% for a period of at least 25 days following administration of the genetically modified live *Plasmodium*.

In some embodiments of the immunogenic compositions administering the immunogenic composition to the primate induces an increase of at least 50% in plasma IL-6.

In some embodiments the immunogenic compositions further comprise at least one immunological adjuvant.

In some embodiments the immunological adjuvant is selected from muramyl peptide type adjuvants, trehalose dimycolate (TDM), lipopolysaccharide (LPS), monophosphoryl lipid A (MPL), carboxymethylcellulose, complete Freund's adjuvant, incomplete Freund's adjuvant, adjuvants of "oil-in-water" emulsion type optionally supplemented with squalene or squalane, mineral adjuvants, bacterial toxins, CpG oligodeoxynucleotides, saponins, synthetic copolymers, cytokines, imidazoquinolones, and combinations thereof.

In some embodiments the immunogenic compositions are formulated for parenteral administration to a primate.

In some embodiments the immunogenic compositions are formulated for administration of an infectious dose of at least $10^4$ genetically modified live *Plasmodium*.

Also provided are uses of an immunogenic composition according to the invention for manufacturing a medicament for generating an antibody and cellular immune response against a *Plasmodium* in a primate.

Also provided are uses of an immunogenic composition according to the invention for manufacturing a medicament for vaccinating a primate against a *Plasmodium*.

Also provided are immunogenic compositions according to the invention for use in generating an antibody response against a *Plasmodium* in a primate.

In a particular embodiment of each of the above described aspects of the invention, the *Plasmodium* parasite is *P. falciparum* and the primate is a human being.

Figure 5:
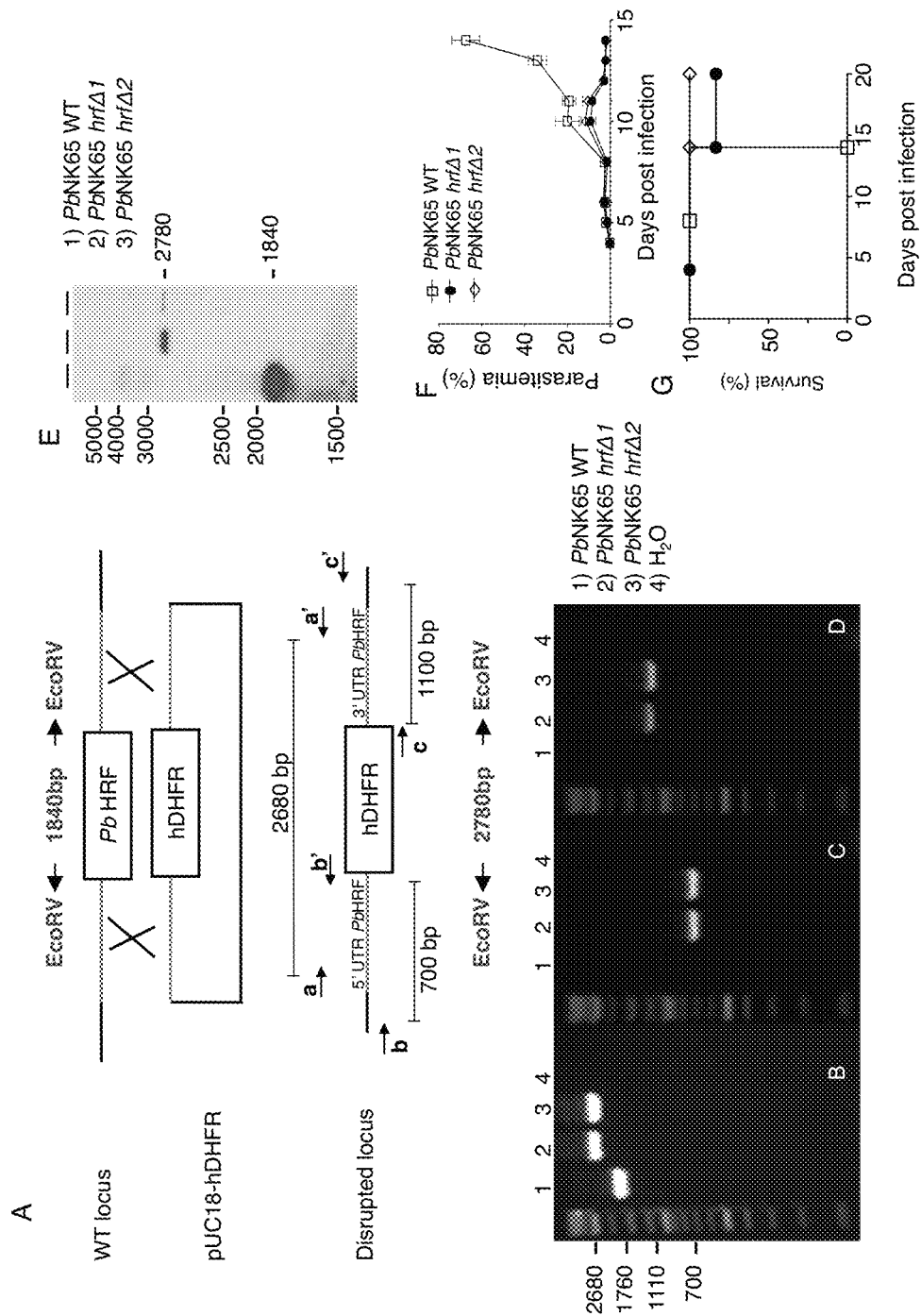

FIG. 5: Disruption of the pbhrf gene in PbNK65 parasites. (A) Schematic representation of the strategy utilized to delete the pbhrf open reading frame in PbNK65 parasites using double-crossover homologous recombination. Red lines represent regions of homology. Successful recombination disrupts the HRF-coding sequence and replaces it with the drug resistance marker hDHFR. (B-D) Specific PCR primers (see table 2) were used to assess genomic integration of hDHFR in PbNK65-hrfΔ clones. Primers used for PCR analysis include (B) a+a', (C) b+b' and (D) c+c', with genomic DNA from: Lane 1, WT parasites; Lane 2, hrfΔ clone 1; Lane 3, hrfΔ clone 2; or Lane 4, $H_2O$. (E) Southern blot analysis of the pbhrf locus in PbNK65 WT and or PbNK65-hrfΔ1 and PbNK65-hrfΔ 2 mutant locus in PbNK65 parasites. WT locus=1840 bp while hDHFR insertion=2780 bp. (F, G) C57BL/6 mice were inoculated with either $10^5$ GFP-expressing WT or PbNK65-hrfΔ1 or PbNK65-hrfΔ2 iRBCs and (F) parasitaemia or (G) survival (Kaplan-Meier survival plots: log-rank test, n=11, P=0.007) followed over time. Experiments were replicated three times.

Figure 1:
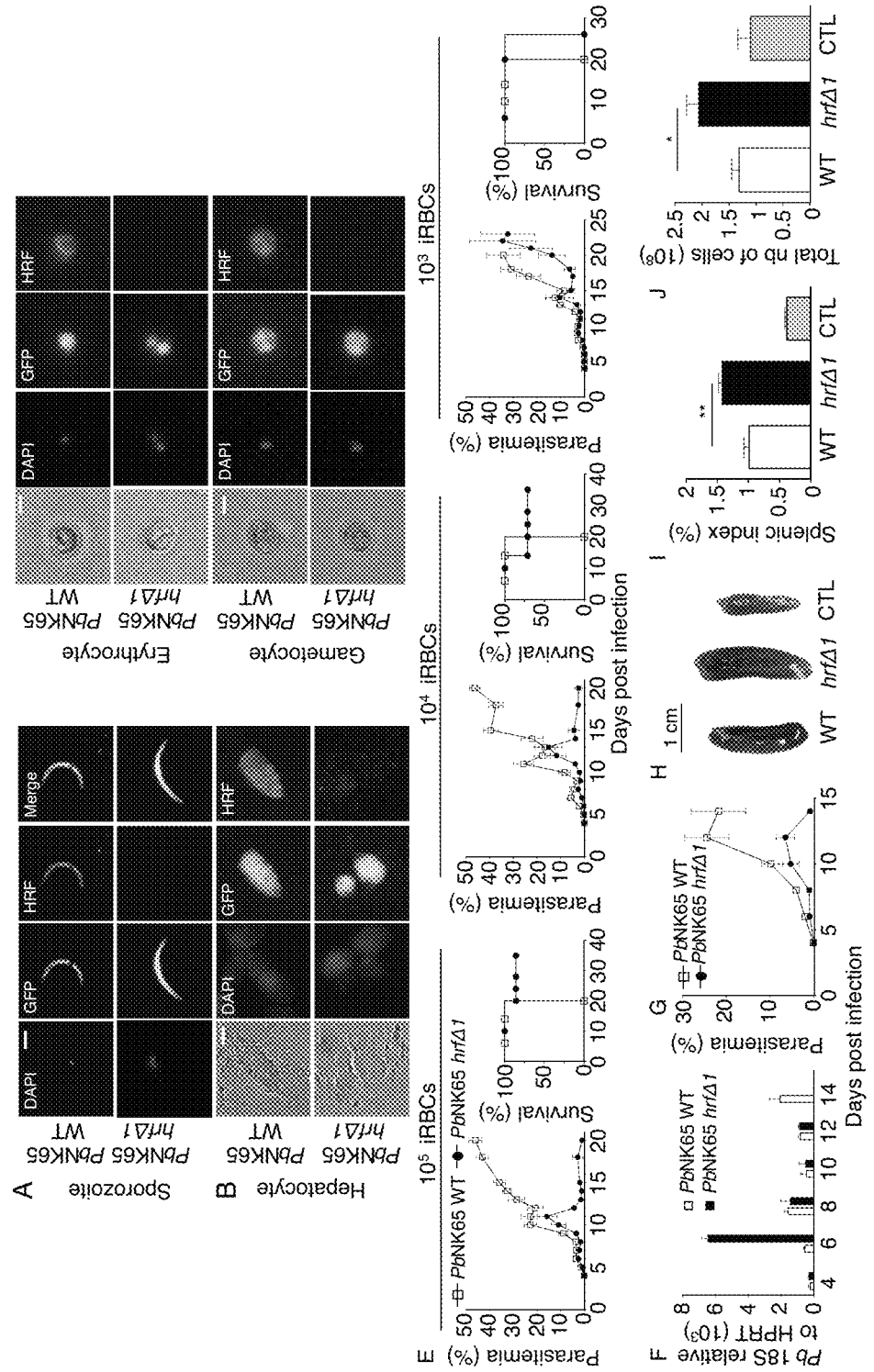
FIG. 1: PbHRF protein expression and phenotype of mutant parasites. Anti HRF-based immunofluorescence (Red) was used to detect HRF in GFP-expressing WT or PbNK65-hrfΔ1 (A) sporozoites, (B) liver stages obtained 48 h post-infection of HepG2 cells with sporozoites at a MOI of 1:1, (C) infected erythrocytes, and (D) gametocytes. Nuclear DNA stained with DAPI and phase-contrast images are shown. (E) Blood-stage parasitemia and survival of C57BL/6 mice (Kaplan-Meier survival plots) after intraperitoneal injection of $10^5$, $10^4$, $10^3$ WT or PbNK65-hrfΔ1-infected iRBCs were measured over several days. Kinetics of parasite load in the spleen of WT or PbNK65-hrfΔ1-infected mice was determined by (F) RT-qPCR analysis of *P. berghei* 18s rRNA expression relative to mouse HPRT mRNA levels, or (G) flow cytometric analysis of parasitaemia. (H) Spleen size of WT or PbNK65-hrfΔ1-infected mice at day 6 p.i. (I) Splenic index and total cell number (J) were compared at day 6 p.i between mice infected with $10^5$ WT or PbNK65-hrfΔ1 iRBCs. CTL: splenic index and cell number from naïve mice. Error bars, SEM. Data are representative of three (A-D, H-J), six (E), and two (F, G) independent experiments with 5 to 6 mice per group. (A-D) 100× magnification, scale bar=6 mm. * P=0.029, ** P=0.003, Mann-Whitney test.
Figure 2:
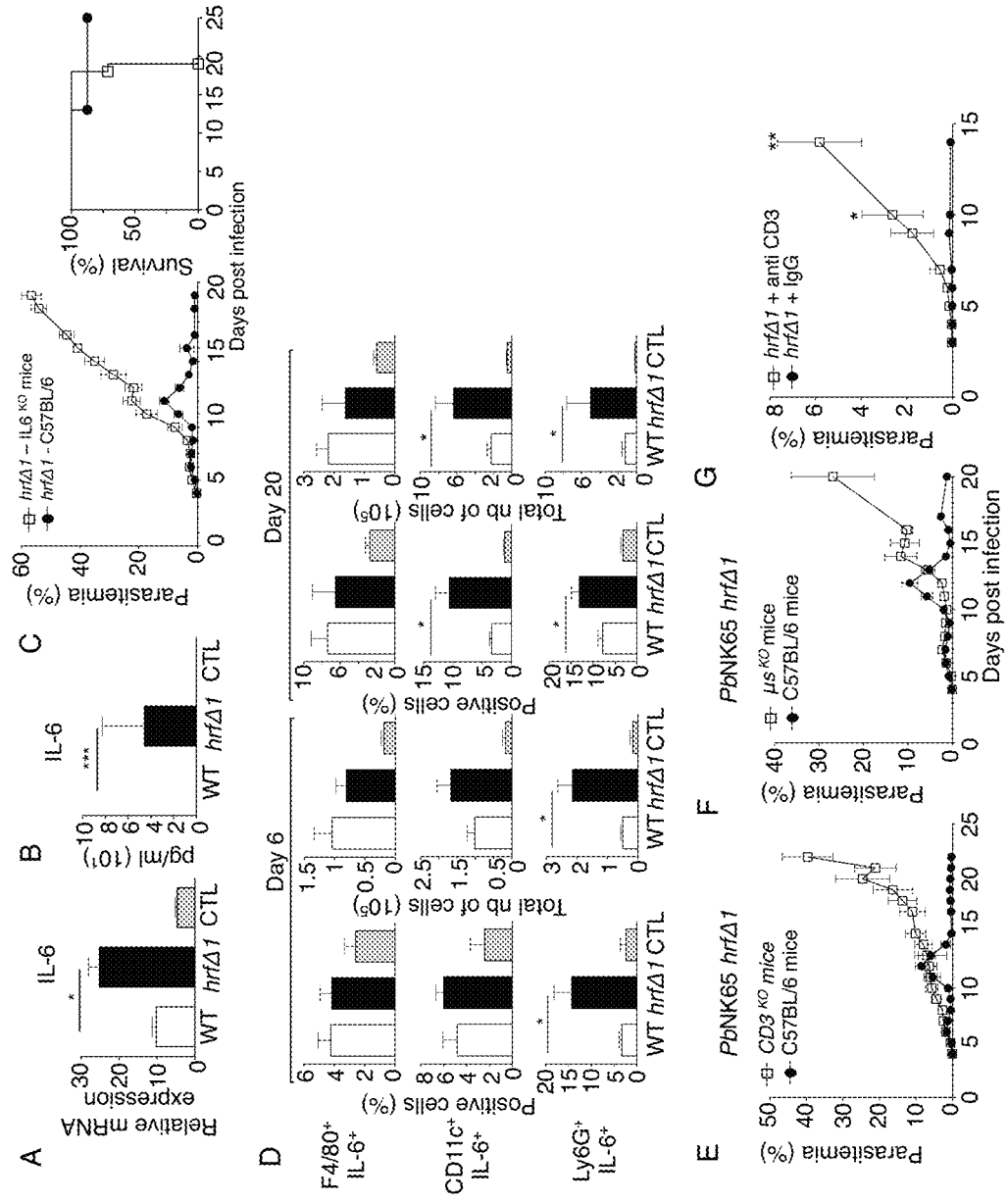
FIG. 2: IL-6 expression by neutrophils and dendritic cells and T and B cells are essential for the clearance of PbNK65-hrfΔ parasites. mRNA levels (RT-qPCR) normalized to HPRT of IL-6 in the spleen (A), and in the serum (ELISA) (B) measured at day 6 p.i. from WT or PbNK65-hrfΔ1 infected mice. CTL: mRNA and sera from naïve mice. (C) Wild-type or IL-6$^{KO}$ C57BL/6 mice were infected i.p. with $10^5$ PbNK65-hrfΔ1 iRBC s. Parasitemia and mouse survival (Kaplan-Meier survival plots: log-rank test, p=0.0046) were followed over time. (D) Frequency and absolute numbers of IL-6-expressing splenic macrophages, dendritic cells, and neutrophils at day 6 and day 20 p.i. from mice (5 per group) infected with $10^5$ WT or PbNK65-hrfΔ1 iRBC s or from naïve mice (CTL). (E) Wild-type or T-cell deficient, or (F) B cell-deficient C57BL/6 mice were infected intraperitoneally with $10^5$ PbNK65-hrfΔ1 iRBC s and parasitaemia was followed over time. (G) Protected mice were treated with IgG or with anti-CD3 depleting antibody one day prior a challenge with WT parasites followed by two booster injections of anti-CD3 at day 1 and 3 post-challenge. Error bars, SEM. Data are representative of four (A, B), three (C, E-G), and two (D) independent experiments with 5 to 7 mice per group. * 0.0028 <P<0.046,  P=0.019, * P=0.0097, Mann-Whitney test.
Figure 3:
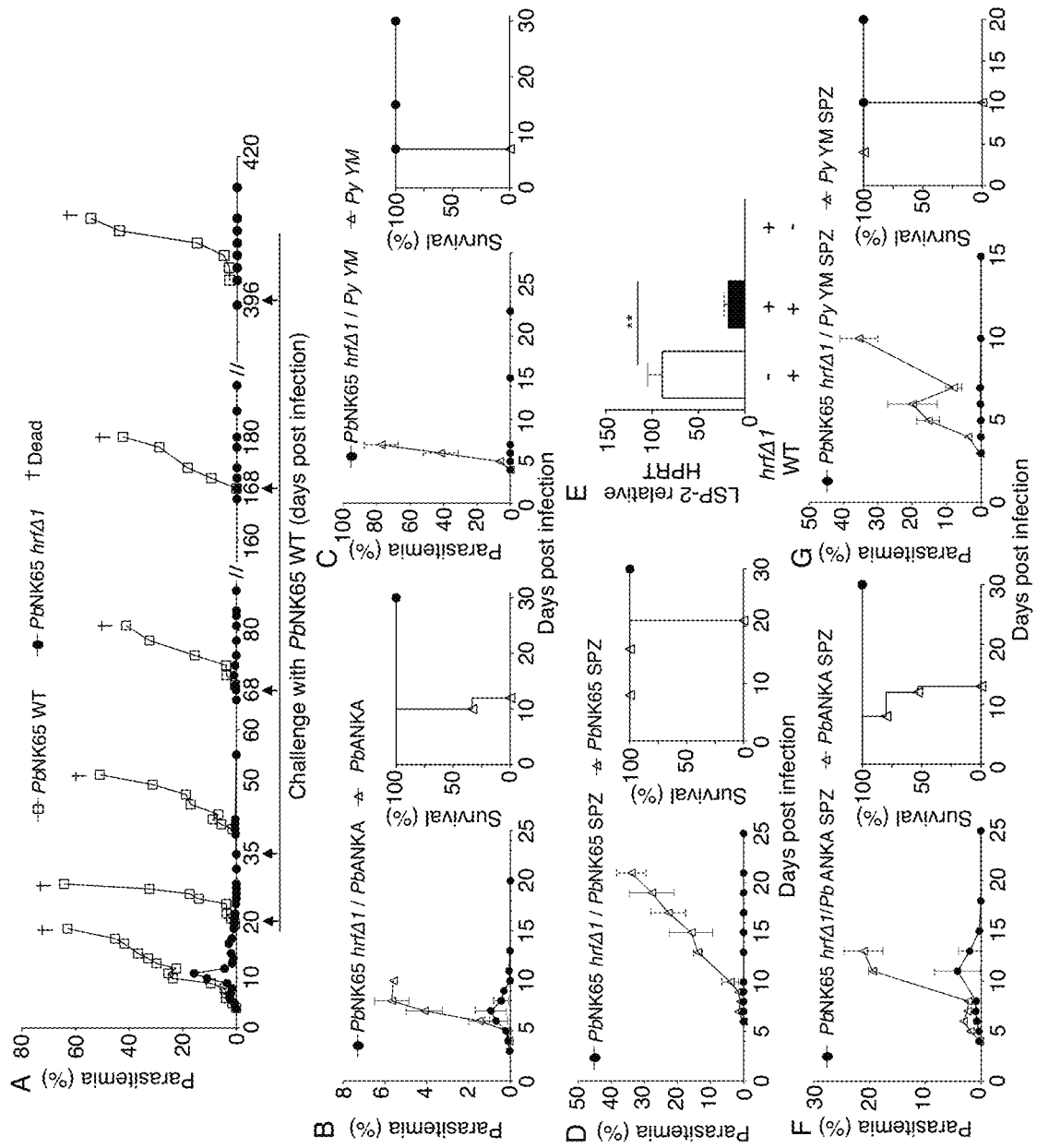
FIG. 3: Infection with HRF-deficient blood stage parasites ensures long-lasting cross-species and cross-stage protection. (A) PbNK65-hrfΔ1-protected mice were challenged with $10^5$ WT PbNK65 iRBCs at indicated time points where CTL naive mice were also infected with $10^5$ WT PbNK65 iRBCs. Parasitemia and survival were measured over time. Parasitemia and Kaplan-Meier survival plots of PbNK65-hrfΔ1-protected mice challenged with $10^5$ (B) PbANKA (log-rank test, P=0.0027) or (C) *P. yoelii* YM (log-rank test, P=0.0047) iRBCs at day 20 and day 23 p.i., respectively, or (D) with $10^4$ GFP-expressing WT PbNK65 sporozoites (log-rank test, P=0.0047) at day 36 p.i. (E) Intrahepatic parasite development in experimental and control mice from (D) was assessed by RT-qPCR analysis of the liver stage specific LSP-2 marker at 40 h p.i. of sporozoites. PbNK65-hrfΔ1-protected mice were challenged with $10^4$ PbANKA (F) or *P. yoelii* YM (G) sporozoites at day 25 p.i. and parasitaemia and survival (log-rank test, P=0.0082) determined over time. Naive mice infected on the same day with PbANKA (F) or with *P. yoelii* YM (G) sporozoites were used as controls. Error bars, SEM. Data are representative of two (A), and three (B-G) independent experiments with 4 to 8 mice per group. ** P=0.015, Mann-Whitney test.
Figure 4:
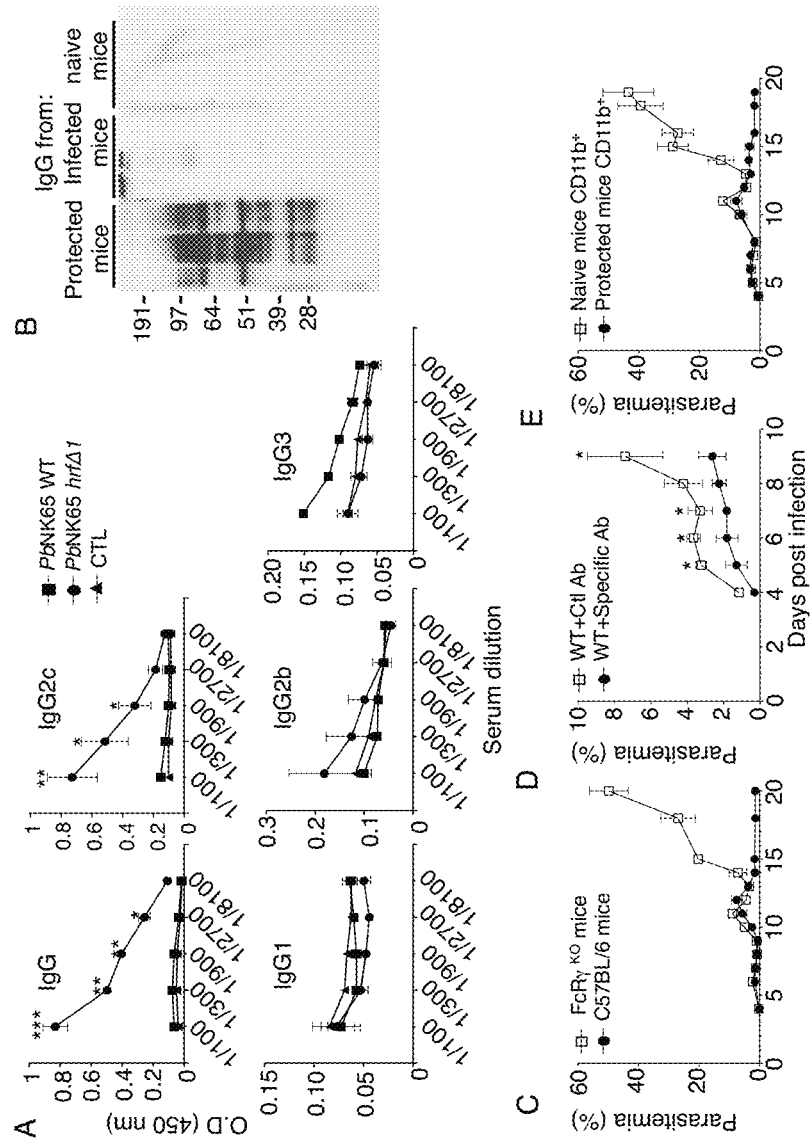
FIG. 4: PbNK65-hrfΔ1-induced immunity is T and B cell-dependent and involves the secretion of *Plasmodium*-specific IgG2c antibodies. (A) ELISA detection and quantification of anti-parasite specific antibodies of various isotypes in mouse sera at day 20 p.i with WT or PbNK65-hrfΔ1 parasites. CTL: sera from naive mice. (B) Separated total protein extracts from WT PbNK65 iRBCs were incubated with IgG fraction from three independent mice infected with either PbNK65-hrfΔ1, or WT parasites at day 20 p.i., or with normal mouse IgG. (C) C57BL/6 or FcRγ$^{KO}$ mice were infected i.p. with $10^5$ PbNK65-hrfΔ1 iRBCs and parasitaemia was followed over time. (D) Purified IgG antibodies from PbNK65-hrfΔ1-protected mice or from naive mice were injected i.p. one day prior and one day post infection with $10^5$ WT PbNK65 iRBCs, and parasitemia was recorded over time. (E) Sorted CD11b+ cells from naive or PbNK65- hrfΔ1-protected mice were transferred into wild-type C57BL/6 mice and immediately infected with $10^5$ WT PbNK65 iRBCs. Parasitemia was recorded over time. Error bars, SEM. Data are representative of three (A-D) and two (E) independent experiments with 5 to 7 mice per group. * $0.019<P<0.03$,  $0.0079<P<0.01$, * $P=0.0002$, Mann-Whitney test.
Figure 6:
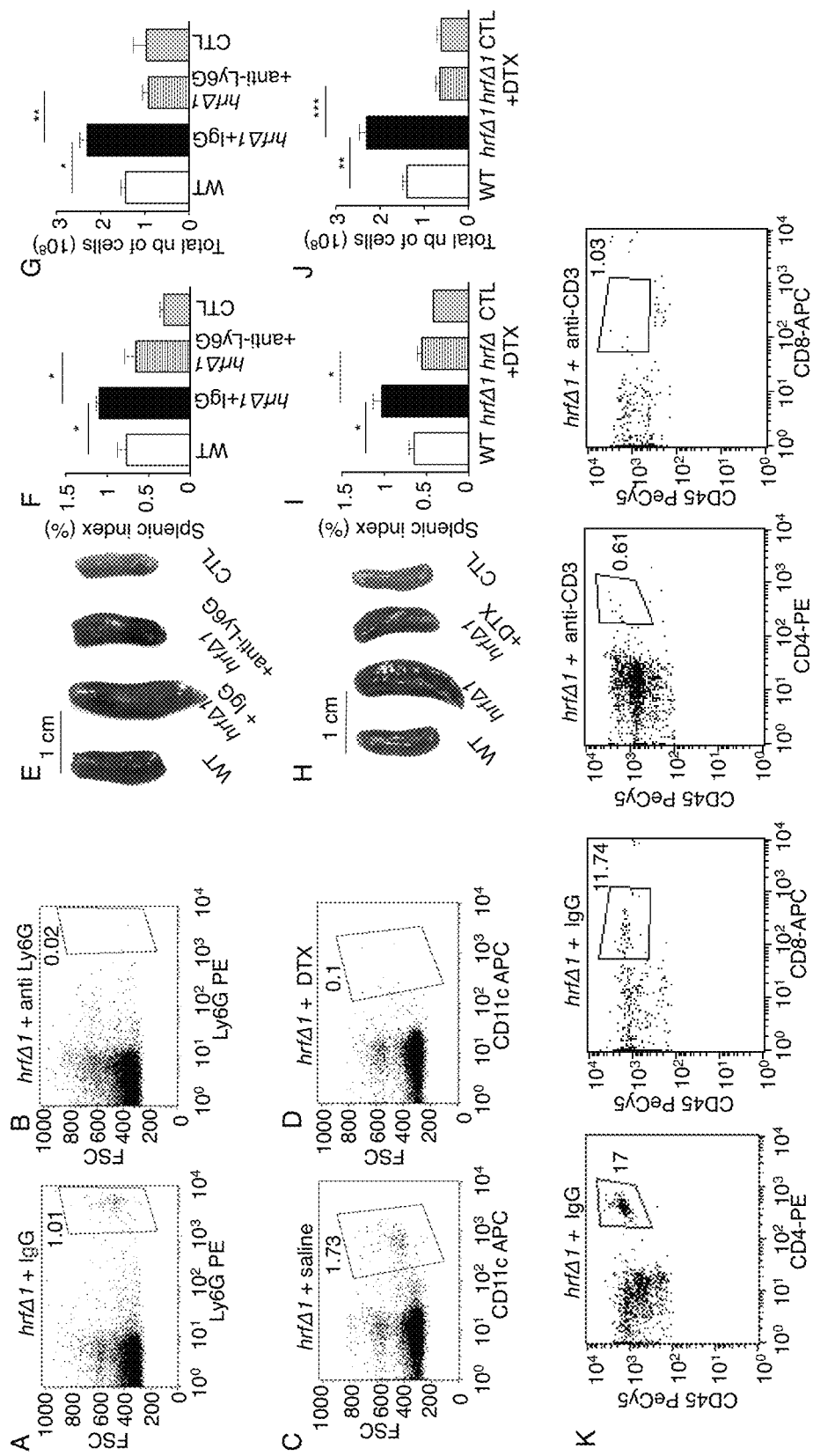

FIG. 6: Assessment of leukocyte depletion and role of neutrophils and dendritic cells in the occurrence of splenomegaly. In vivo depletion of neutrophils using anti-neutrophil antibody (B) or normal IgG (A) was assessed by measuring at days 6 p.i the percentage of residual Ly6G+ neutrophils in spleen by FACS analysis. Depletion of DCs was performed by injection of diphteria toxin (DTX) (D) or saline (C) into CD11c-DTR-GFP mice and at days 6 p.i percentage of CD11c+ cells was determined in spleens by FACS analysis in spleen. Comparison at day 6 p.i. of splenic indexes and total number of leukocytes in WT- and PbNK65-hrfΔ1 infected mice untreated or depleted of neutrophils (E-G) or DCs (H-J). (K) Control of T cell depletion (FIG. 2G): protected mice received anti-CD3 depleting antibody one day prior a challenge with WT parasites followed by two booster injections of anti-CD3 at day 1 and 3 post-challenge with PbNK65 WT parasites. T-cell depletion efficiency was assessed by FACS analysis using anti-CD4-PE or anti-CD8-APC in blood samples from protected mice that were challenged at day 15 p.i with PbNK 65 WT parasites. Analysis was performed 10 days post-challenge. Error bars, SEM. Data are representative of two independent experiments with 5 to 6 mice per group. * $P=0.028$,  $P=0.015$, * $P=0.009$, Mann-Whitney test.

Figure 7:
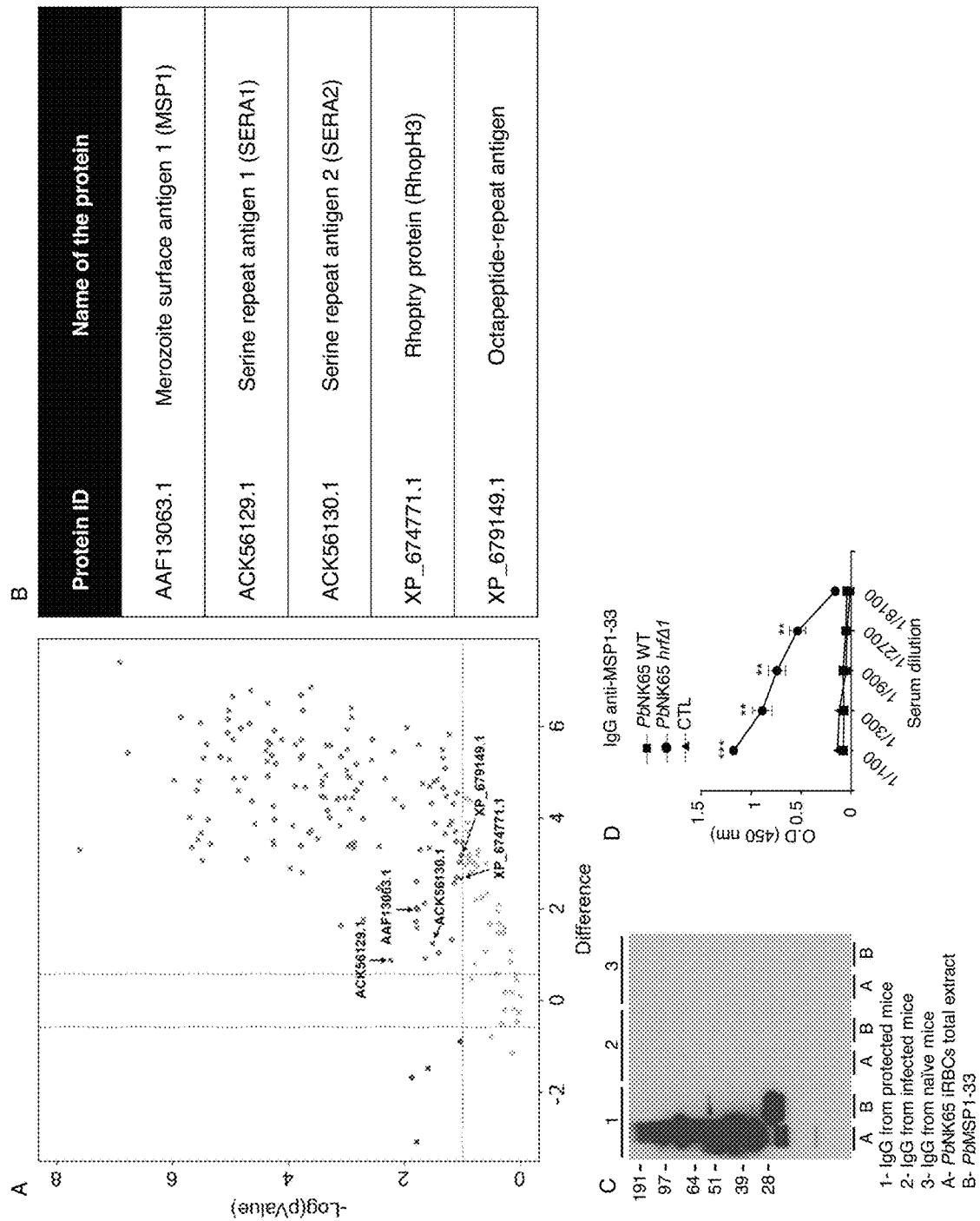

FIG. 7: Identification of immune sera-derived immunoprecipitated proteins. *P. berghei* antigens recognized specifically by IgGs from PbNK65-hrfΔ1-protected mice serum were identified by mass spectrometry. (A) Volcano plot representing results of the immunoprecipitated proteins of PbNK65 parasite extract. This plot is colored such that those points having a fold-change less than 1.5 are shown in gray (below the horizontal dashed line), points >1.5 are in red (above the horizontal dashed line in the right section); points <1.5 are in blue. (above the horizontal dashed line in the left section) Green and red dots display both large-magnitude fold-changes (x-axis) as well as high statistical significance (−log lO of p-value, y-axis). The dashed black-line shows where p=0.05 with points above the line having p<0.05 and points below the line having p>0.05. Statistical analysis was performed on triplicate samples. (B) Selected proteins for further validation are in green (indicated by an arrow) and they are reported in the table (B). Evidence that protected sera actually recognize the green dot, AAF13063. 1 identified as MSP1 protein, was assessed by using a recombinant PbMSP1-33 protein by immunoblot (C) and by ELISA (D). Experiments were replicated three times (6 mice per group).  $0.02<P<0.028$, * $P=0.0002$, Mann-Whitney test.

Figure 8:
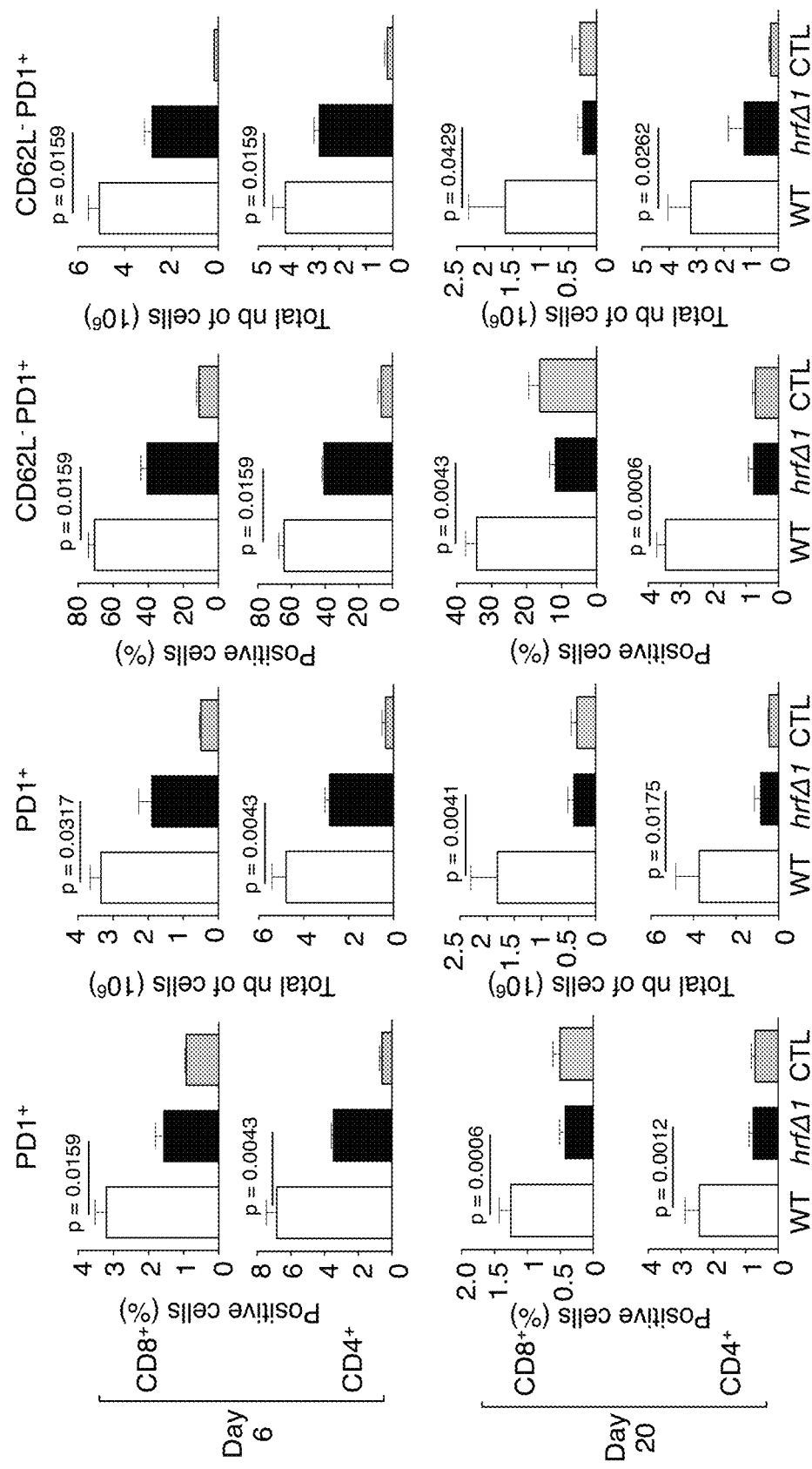

FIG. 8: Protection induced by hrfΔ1 PbNK65 parasites is associated with reduced induction of PD1+CD8+CD62L− and PD1+CD4+CD62L− cells in spleen. Representative frequency and absolute number of CD8+PD1+ and CD4+PD1+ splenic leukocytes at day 6 and day 20 p.i. with either $10^5$ GFP-WT or hrfΔ1 iRBCs. Representative frequency and absolute number of CD8+CD62L− and CD4+CD62L− splenic leukocytes expressing the PD1 receptor at day 6 and day 20 post infection with either $10^5$ GFP-WT or hrfΔ1 iRBCs. Data are presented as the means±SEM from two distinct experiments (n=5).

Figure 9:
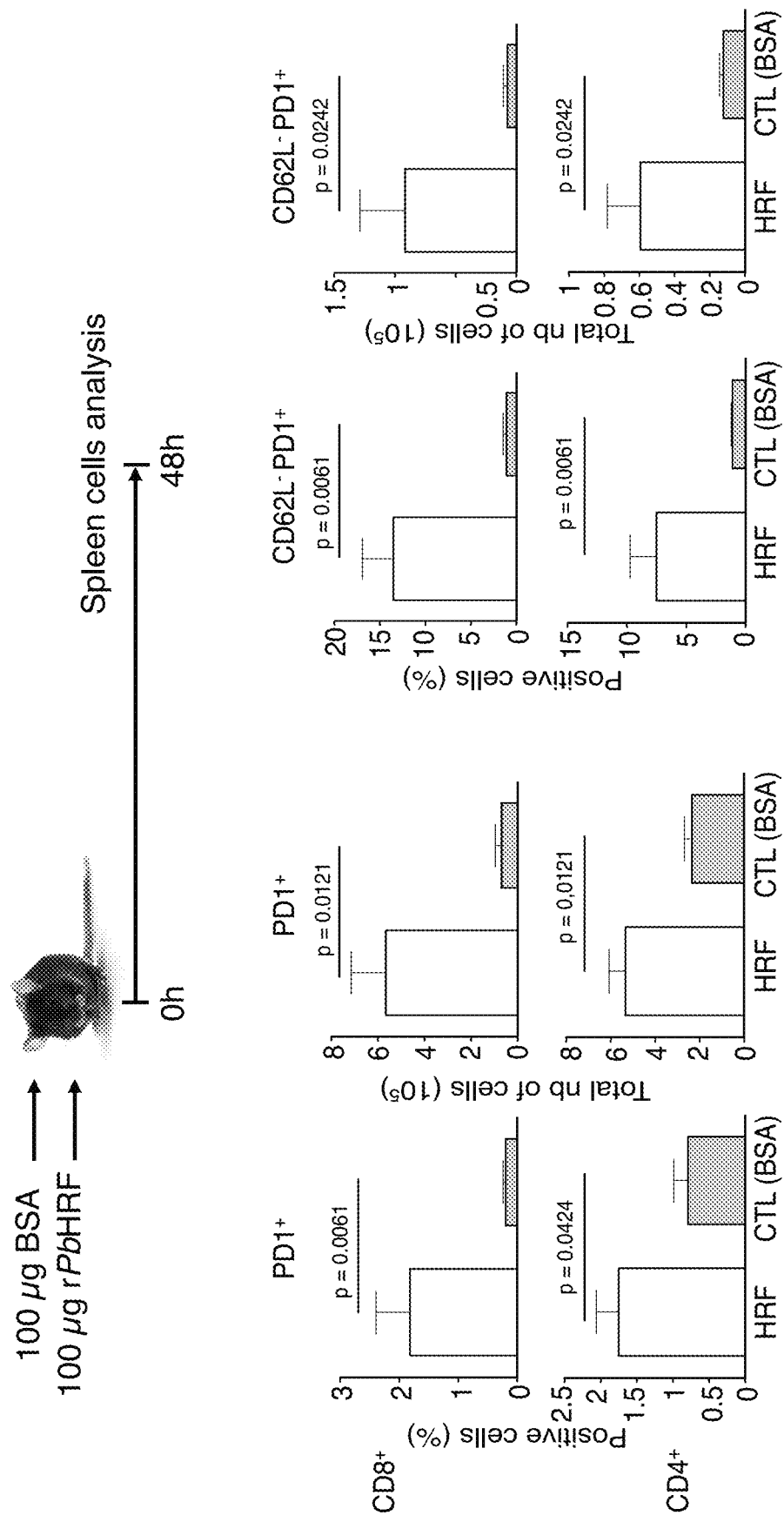

FIG. 9: Administration of *P. berghei* recombinant HRF protein to naive mice is associated with induction of PD1+CD8+CD62L− and PD1+CD4+CD62L− cells in spleen. Representative frequency and absolute number of CD8+PD1+ and CD4+PD1+ splenic leukocytes 48 h after PbHRF administration (IV). Representative frequency and absolute number of CD8+CD62L− and CD4+CD62L− splenic leukocytes expressing the PD1 receptor 48 h after PbHRF administration (IV). Data are presented as the means±SEM from two distinct experiments (n=8).

Figure 10:
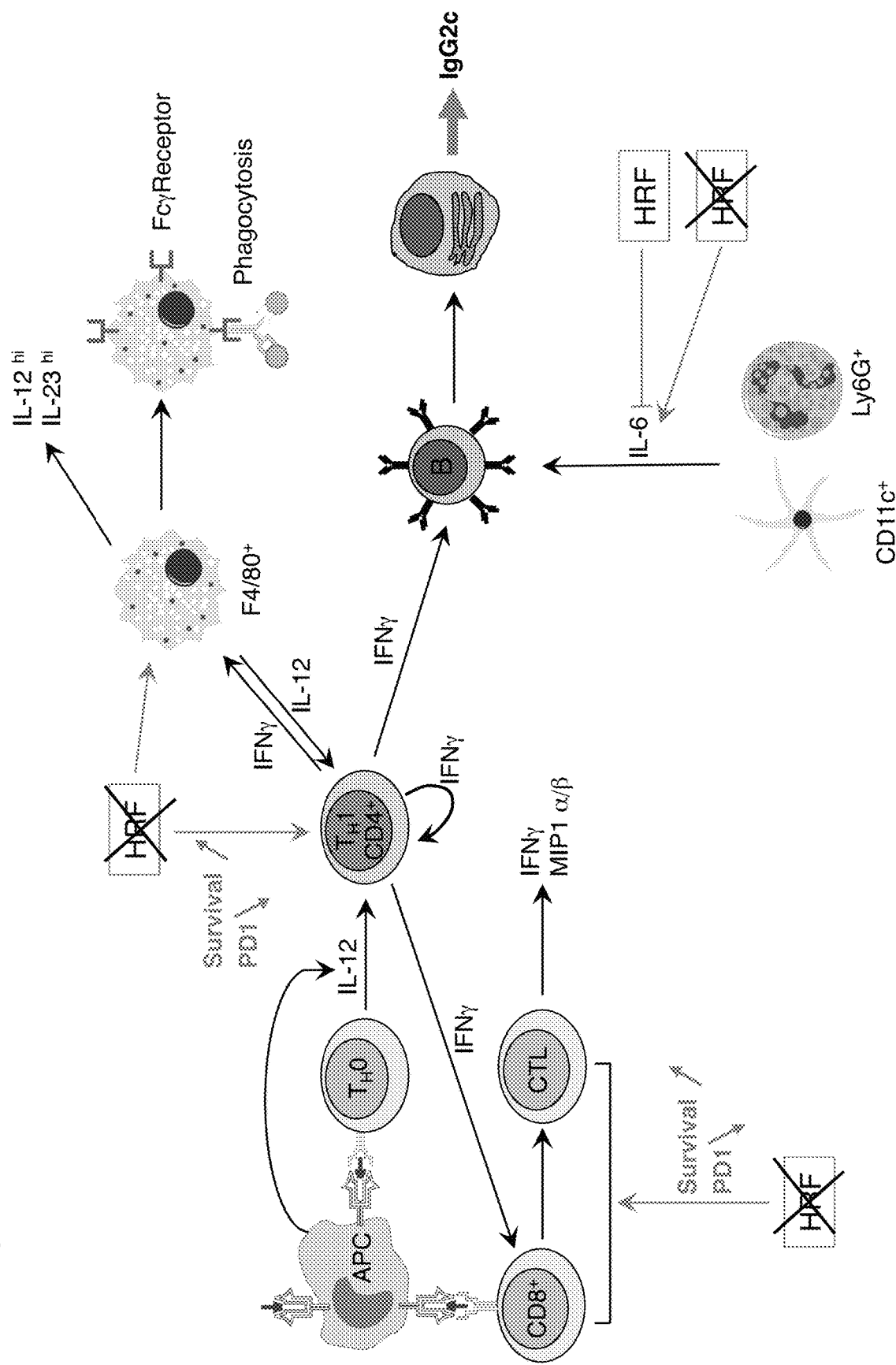

FIG. 10: Schematic representation of how HRF modulates varions pathways of the host immune response. The *Plasmodium* HRF protein acts at four different levels: 1) during parasite infection, antigen presenting cells (APC) produce IL-12 which causes the differentiation of naive T helper cells into IFN-γ producing TH1 CD4 cells. This response is abrogated by HRF; 2) HRF is responsible for the impairment of T cell functions by increasing PD-1 expression; 3) HRF impairs macrophage phagocytic activity; and 4) HRF inhibits IL6 expression which results in the inhibition of B cell differentiation and proliferation leading to the abrogation of anti-parasite antibody response.

Ther colours described in respect of FIGS. 1-10 may be explicitly seen in publication reference 23.

Figure 11:
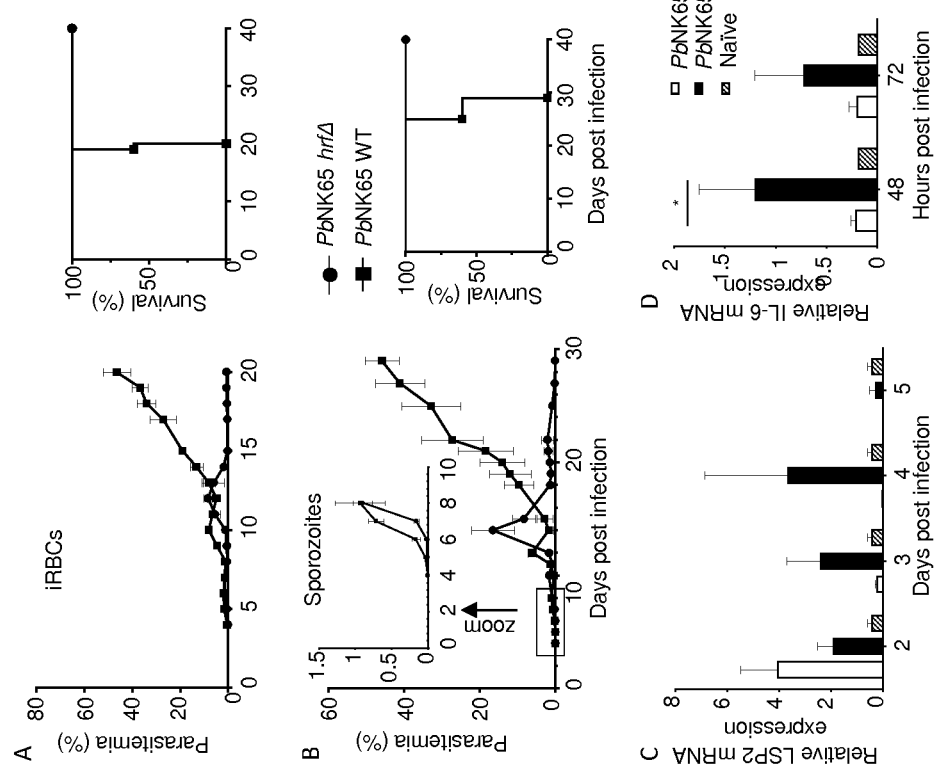

FIG. 11: Marked differences in parasitaemia between WT and PbNK65 hrfΔ-infected mice during blood stage development. Blood-stage parasitemia and survival (Kaplan-Meier survival plots) of C57BL/6 mice after (A) i.p. injection of $10^5$ iRBCs or (B) i.v. injection of $10^3$ isolated sporozoites of WT or PbNK65 hrfΔ parasites were measured at indicated time points. After infection with WT or PbNK65 hrfΔ sporozoites, livers were collected at indicated time points and RT-qPCR analysis were used to measure (C) the kinetics of parasite load using the liver stage specific LSP-2 marker expression relative to the parasite control gene HSP70 and (D) IL-6 expression using IL-6 mRNA expression relative to mouse HPRT mRNA levels. Error bars, SEM. Data are representative of two independent experiments with 5 mice per group. (* p<0.05; Mann Whitney test).

Figure 12:
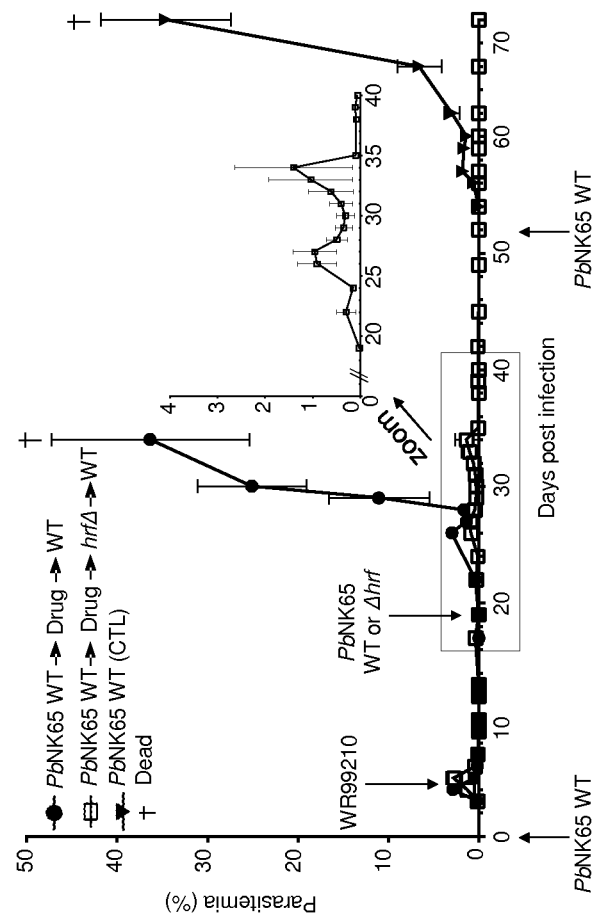

FIG. 12: Prior exposure to WT parasite followed by drug treatment does not hamper PbNK65-hrfΔ-induced parasite clearance and immune protection. Blood-stage parasitemia of C57BL/6 mice after i.p. injection of $10^5$ WT iRBCs and treated at day 4 p.i. with 6 mg/kg WR99210 by subcutaneous injections for three consecutive days. At day 19 p.i. mice that have eliminated the parasite from blood stream after drug treatment were infected with either with $10^5$ WT or PbNK65 hrfΔ iRBCs. Mice infected with PbNK65 hrfΔ parasites were subsequently, after parasite elimination from blood stream, challenged at day 52 p.i. with $10^5$ WT iRBCs. Parasite development was measured over several days by flow cytometry. Error bars, SEM. Data are representative of three independent experiments with 5 mice per group.

Figure 13:
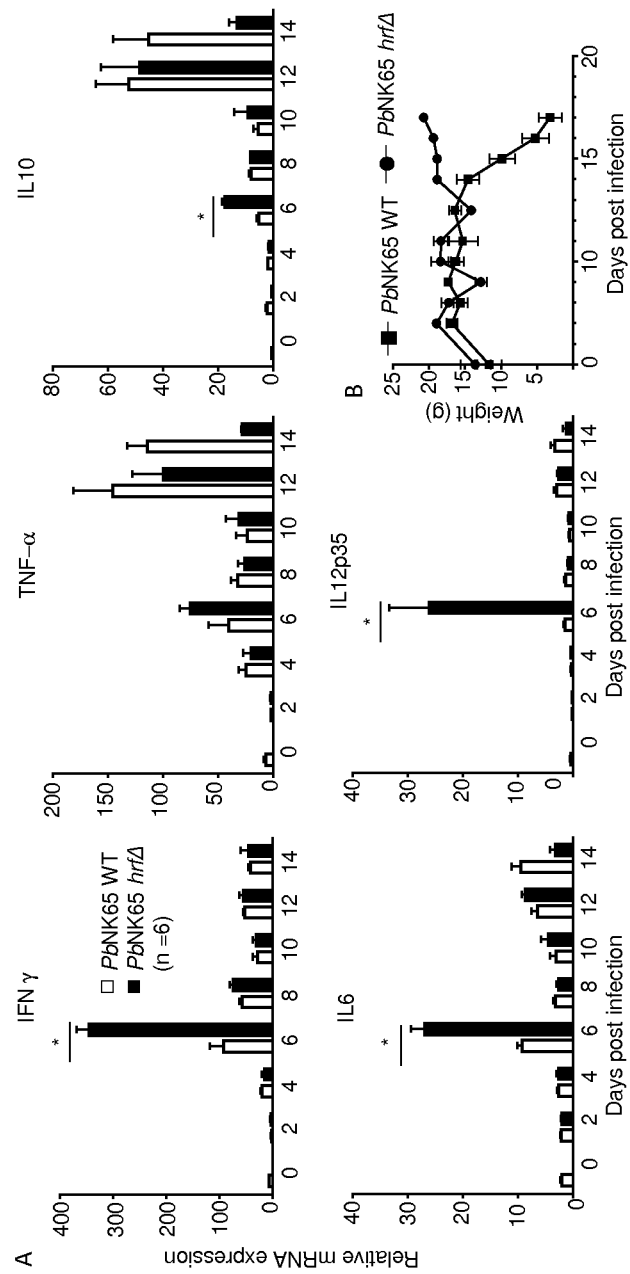

FIG. 13: Immune response genes are differentially regulated by WT and hrfΔ parasites. (A) mRNA levels (RT-qPCR) normalized to HPRT of cytokine production in spleen cells measured at different time points p.i., every other day from day 2 to day 14 p.i., from mice infected with $10^5$ WT or PbNK65 hrfΔ iRBCs. (B) Determination of body weight measured over time during C57BL/6 mice infection. Error bars, SEM. Data are representative of two independent experiments with 5 mice per group. (* $p<0.03$; Mann Whitney test).

Figure 14:
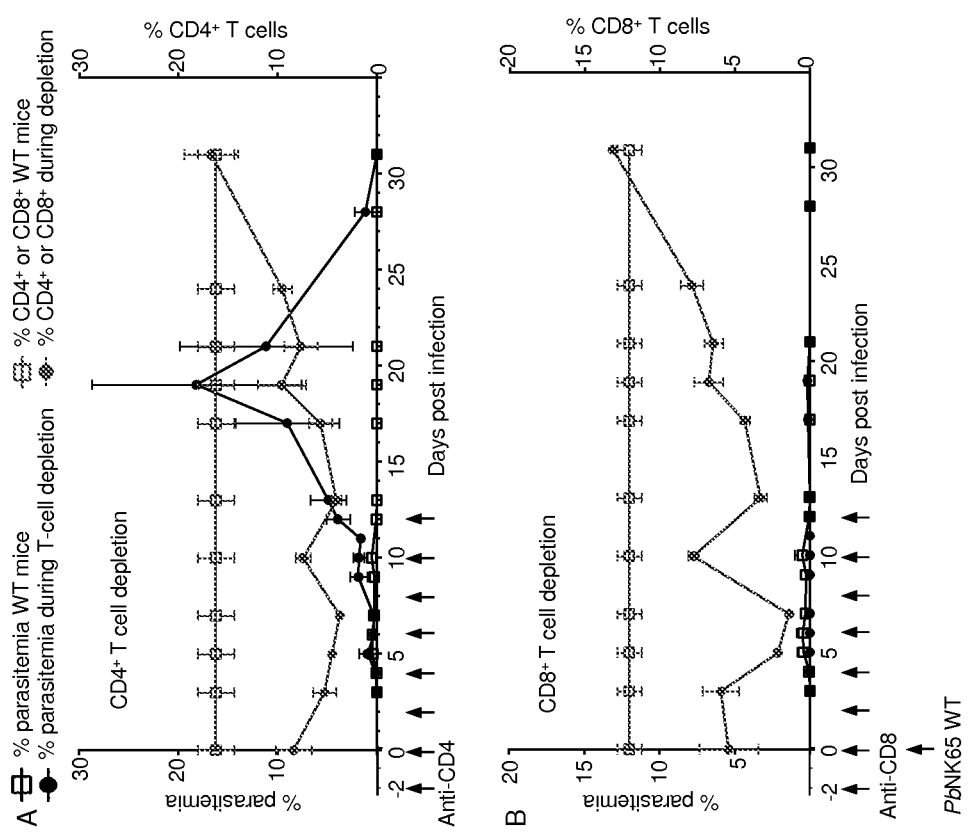

FIG. 14: Influence of CD4+ or CD8+ T cells depletion on parasite development in protected mice. PbNK65 hrfΔ iRBCs-protected mice were treated either with IgG or with anti-CD4- (A) or with anti-CD8-depleting Abs (B) 2 days prior to a challenge with $10^5$ iRBCs WT parasites followed by 6 injections of IgG, anti-CD4 or anti-CD8 Abs administered every other day after the infection. Anti-CD4 and CD8 treatment was discontinued at day 12 p.i. Parasitemia as well as determination of cell counts in the blood were recorded over time. Error bars, SEM. Data are representative of two independent experiments with 5 mice per group.

Figure 15:
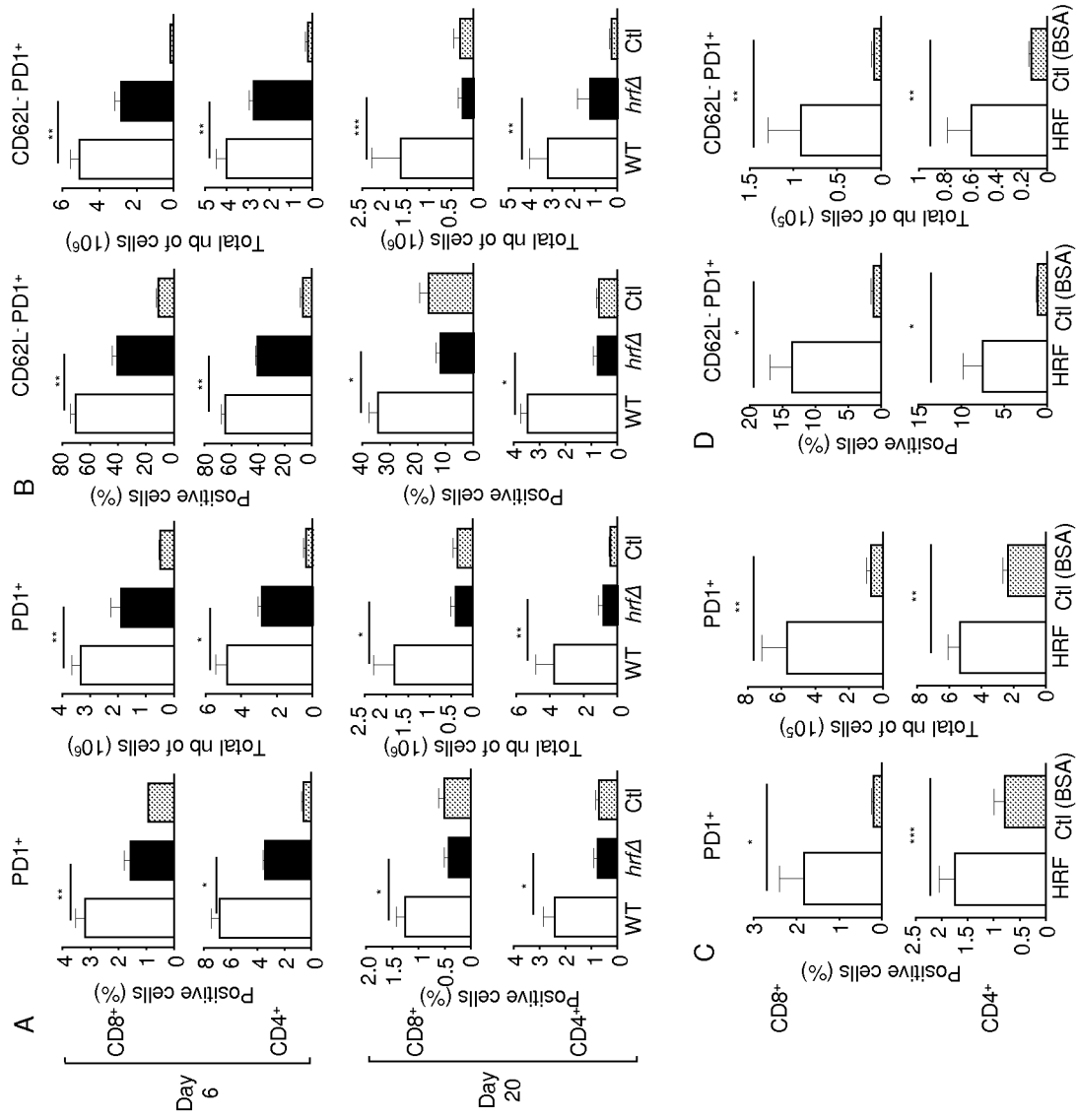

FIG. 15: Protection induced by PbNK65 hrfΔ parasites is associated with reduced induction of PD1+CD8+CD62L- and PD1+CD4+CD62L- cells in spleen. (A) Representative frequency and absolute number of CD8+CD62L- and CD4+CD62L- splenic leukocytes at day 6 and day 20 p.i. with either $10^5$ WT or hrfΔ iRBCs. (B) Representative frequency and absolute number of CD8+CD62L- and CD4+CD62L- splenic leukocytes expressing the PD1 receptor at day 6 and day 20 post infection with either $10^5$ WT or hrfΔ iRBCs. (C) Representative frequency and absolute number of CD8+PD1+ and CD4+PD1+ splenic leukocytes 48 h after recombinant PbHRF administration (i.v.). (D) Representative frequency and absolute number of CD8+CD62L- and CD4+CD62L- splenic leukocytes expressing the PD1 receptor 48 h after recombinant PbHRF administration (i.v.). Error bars, SEM. Data are representative of three (A, B) and two (C, D) independent experiments with 5 and 8 mice per group. (* $0.0006<p<0.0061$,  $0.0121<p<0.0317$, * $p<0.005$; Mann Whitney test).

Figure 16:
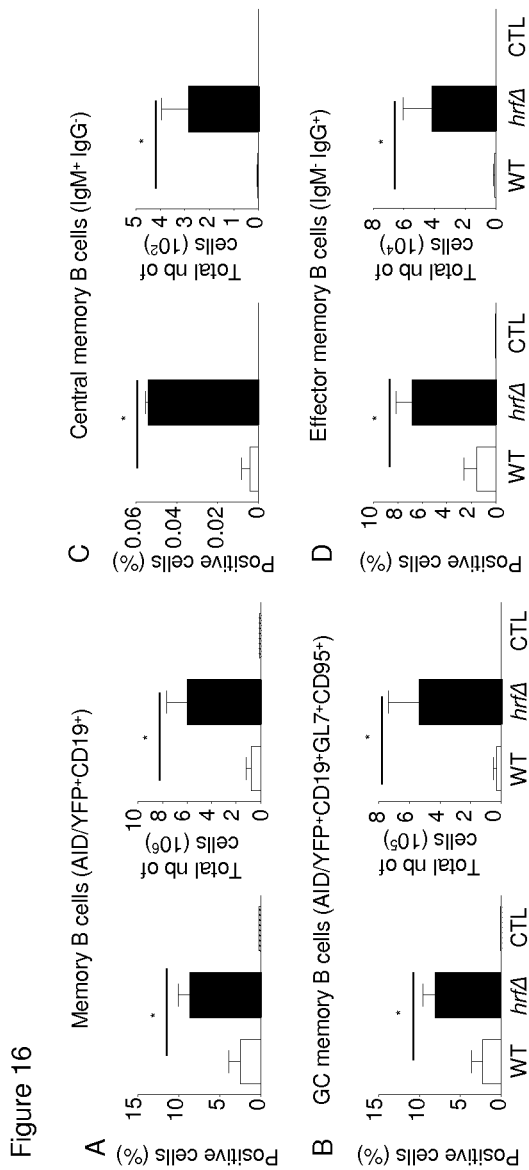

FIG. 16: Frequency of memory B cells in PbNK65-hrfΔ protected mice. Splenic B cells from naive mice or 15 days p.i. with either WT or hrfΔ iRBCs were analysed for their memory phenotype. Representative frequency and absolute number of AID/YFP+CD19+ (A), GC AID/YFP+CD19+ GL7+CD95+ (B) memory B cells. Representative frequency and absolute number, among GC B memory cell population, of IgM+IgG- central memory B cells (C) or IgM-IgG+ effector memory B cells (D). Error bars, SEM. Data are representative of two independent experiments with 4 mice per group. (* $p<0.05$; Mann Whitney test).

TABLE 3

List of oligonucleotides used for RT-qPCR analyses

| Primer | Fw/Rev | Sequence | SEQ ID No |
|---|---|---|---|
| Pb 18S | Fw | ATTAATCTTGAACGAGGAATGGCT | 1 |
|  | Rev | TCAATCGGTAGGAGCGACG | 2 |
| Pb LSP2 | Fw | GCCAAATGCTAAACCTAATG | 3 |
|  | Rev | TGGGTTTGTATTGTATGCAC | 4 |
| Pb HSP70 | Fw | TGCAGCTAATCAAACTC | 5 |
|  | Rev | ACTTCAATTTGTGGAACACC | 6 |
| mu IL-23 | Fw | CCACCAGGACTCAAGGACAACA | 7 |
|  | Rev | GCAGGCTCCCCTTTGAAGA | 8 |
| mu EBB | Fw | CAGAGTGCAATGCCATGCTCC | 9 |
|  | Rev | GCCACACCGAGCCTGTAAGT | 10 |
| mu IL-12p35 | Fw | TACTAGAGAGACTTCTTCCACAACAAGAG | 11 |
|  | Rev | GATTCTGAAGTGCTGCGTTGAT | 12 |
| mu IL-12p40 | Fw | GGAAGCACGGCAGCAGAATA | 13 |
|  | Rev | AACTTGAGGGAGAAGTAGGAATGG | 14 |
| mu IFN-γ | Fw | AAAGGATGCATTCATGAGTATTGC | 15 |
|  | Rev | CGCTTCCTGAGGCTGGATT | 16 |
| mu TNF-α | Fw | CAT CTT CTC AAA ATT CGA GTG ACA A | 23 |
|  | Rev | TGG GAG TAG ACA AGG TAC AAC CC | 24 |
| mu IL-6 | Fw | AAAGAAATGATGGATGCTACCAAAC | 17 |
|  | Rev | CTTGTTATCTTTTAAGTTGTTCTTCATGTACTC | 18 |
| mu IL-10 | Fw | GGCGCTGTCATCGATTTCTC | 19 |
|  | Rev | GACACCTTGGTCTTGGAGCTTATTAA | 20 |
| mu HPRT | Fw | CTGGTGAAAAGGACCTCTCG | 21 |
|  | Rev | TGAAGTACTCATTATAGTCAAGGGCA | 22 |

Figure 17:
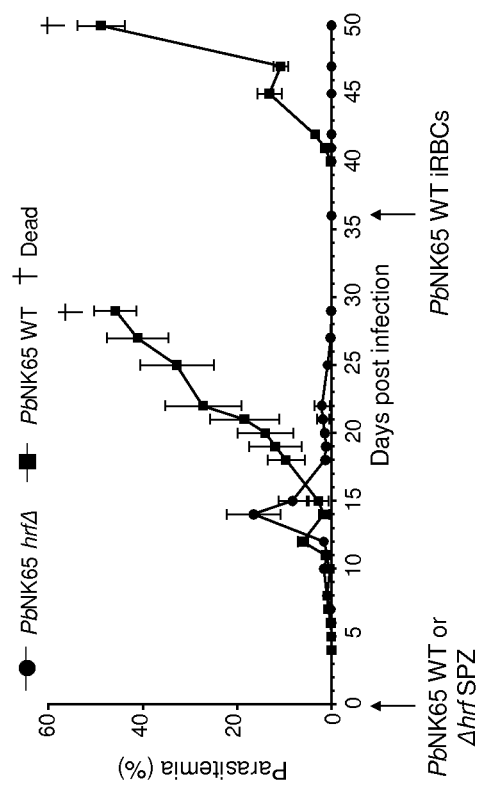

FIG. 17: Assessment of protection after parasite challenge in mice reinfected at day 36 with PbNK65 WT iRBCs. No blood stage parasite development is observed indicating that self-resolved parasites inoculated as PbNK65-hrfΔ sporozoites elicited similar protection as that generated by blood stage PbNK65-hrfΔ parasites.

Figure 18:
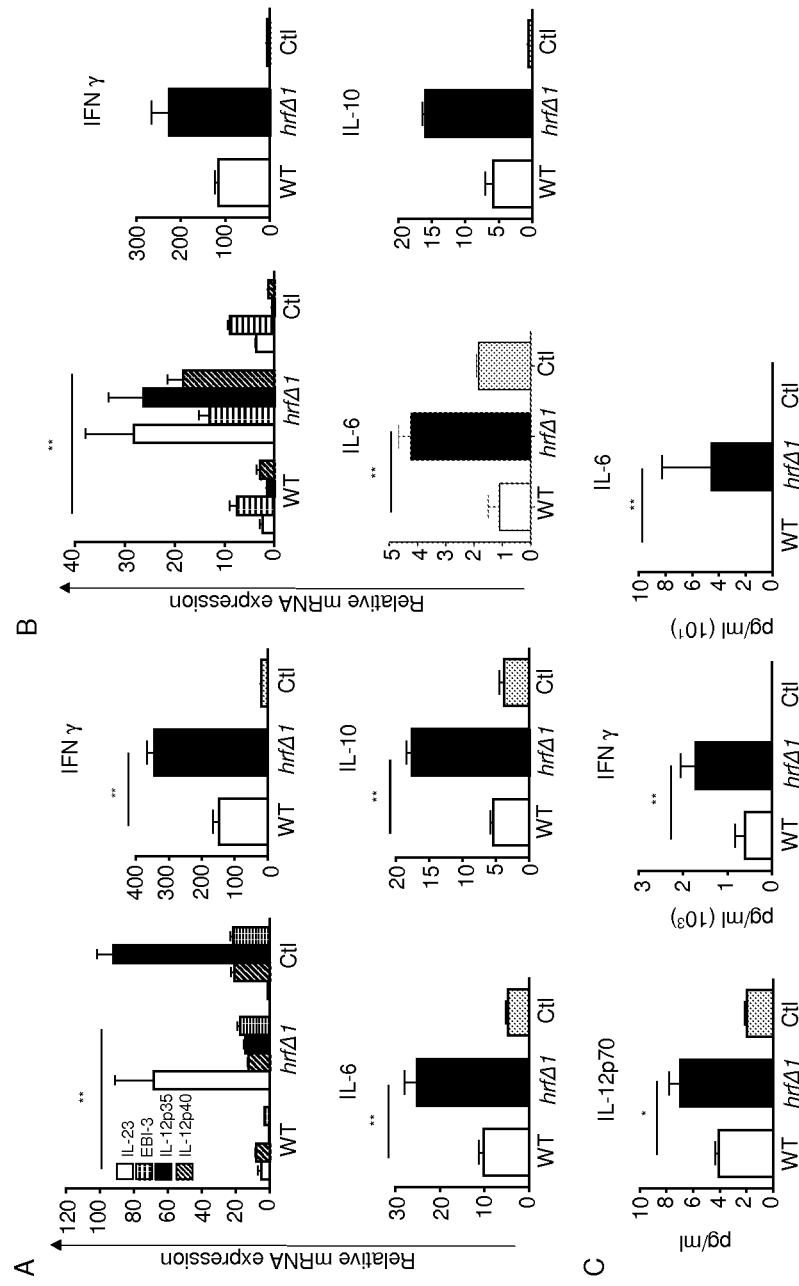

FIG. 18: Detailed analysis of cytokines was performed at day 6 p.i. in the liver and in the spleen of infected mice. Analyzed samples showed that IL-23, EBI-3 (IL-27 beta subunit), IL-12p40, IL-12p35, IFN-g, IL-6, and IL-10 mRNA expression were all higher both in the liver and in the spleen during PbNK65 hrfΔ parasites infection as compared to WT parasites infection (FIG. 18A,B). At the protein level, higher production of IFN-g, IL-12p70, and IL-6, as measured by ELISA, was confirmed in the plasma of PbNK65 hrfΔ infected mice as compared to WT parasite-infected mice (FIG. 18C).

Figure 19:
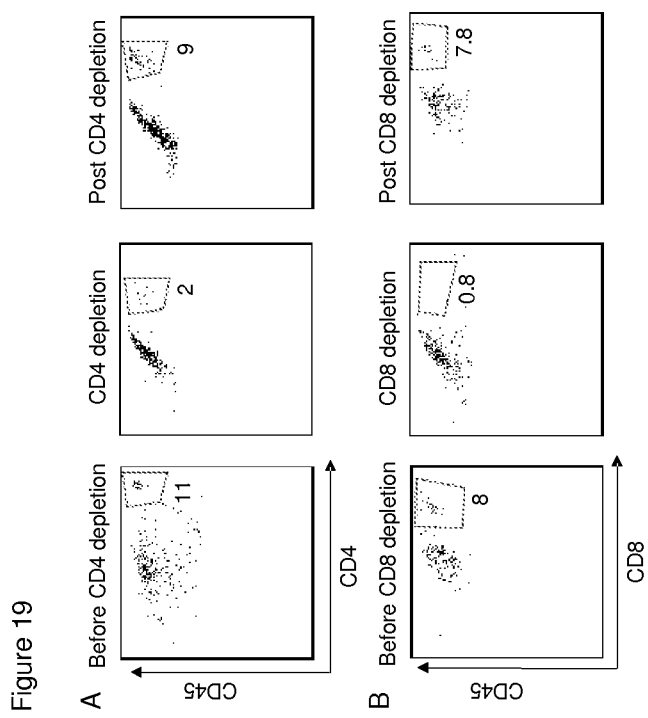

FIG. 19: Monitoring of continuous efficacy of CD4 and CD8 depletion during administration of T-cell depleting antibodies and after this treatment was discontinued.

Figure 20:
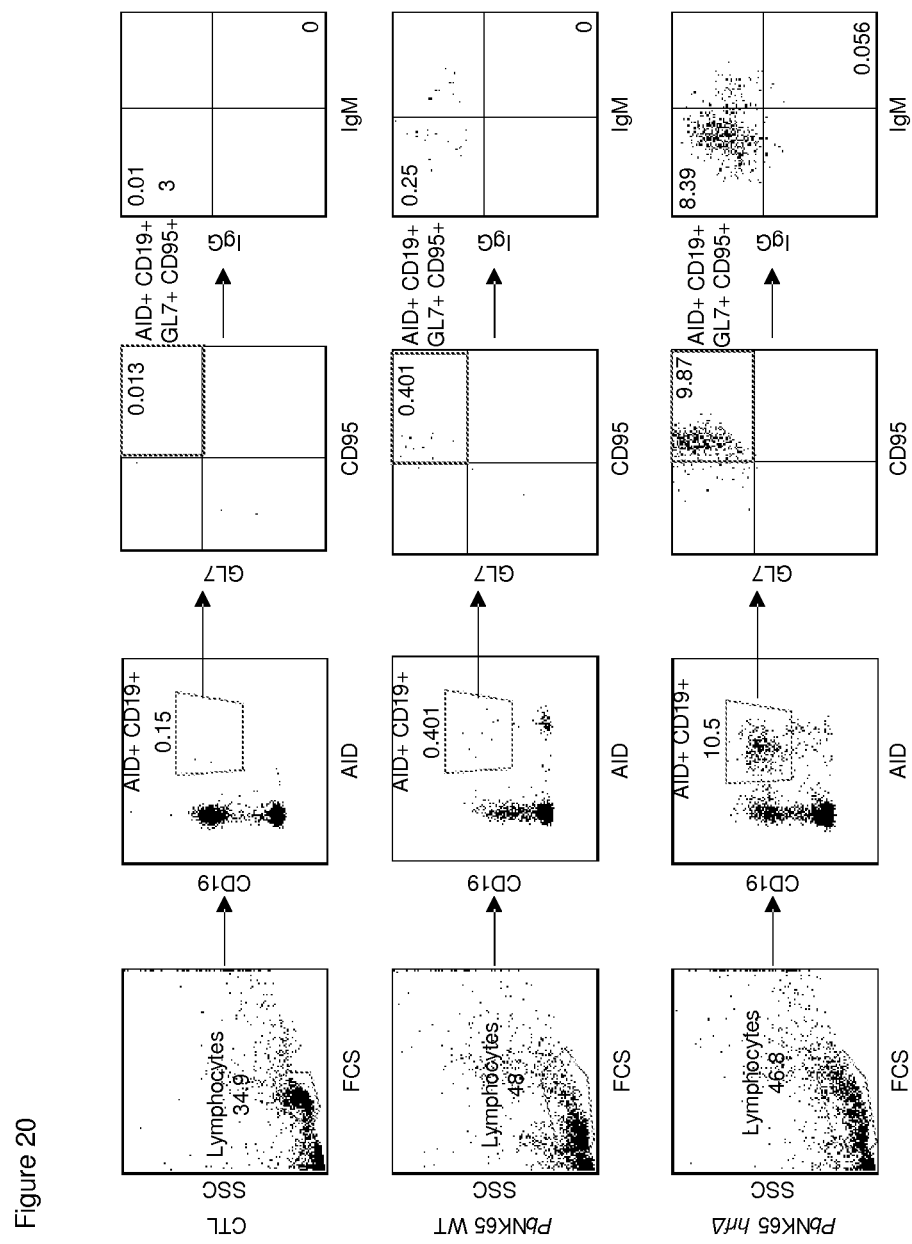

FIG. 20: Analysis of central and memory B cell populations based on a combination of cell surface markers using a first gating on CD19+ AID-YFP+ cells followed by another gate on GL7+ CD95+ cell population and finally gating on IgG+ or IgM+ cell populations.

Figure 21:
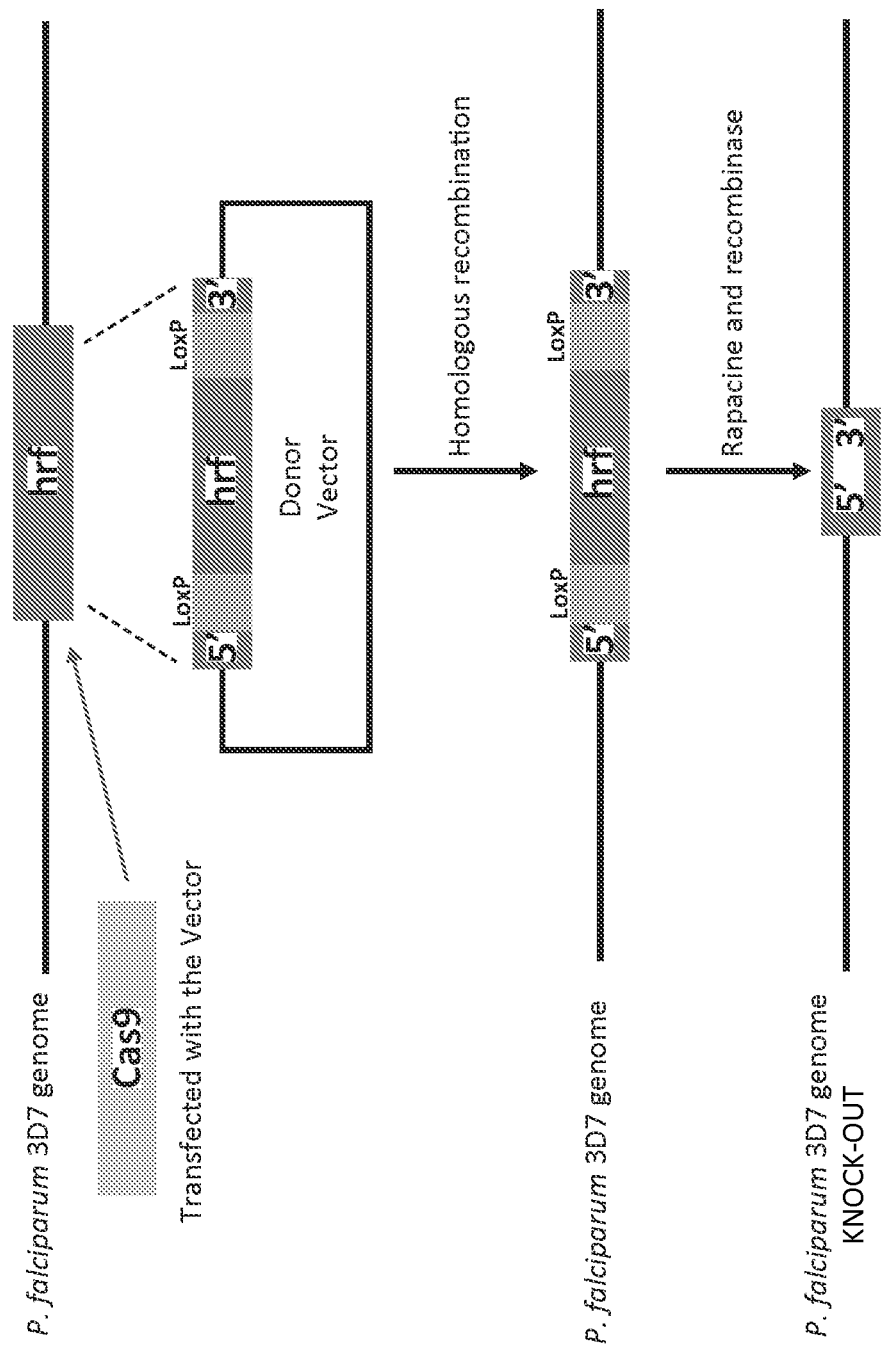

FIG. 21: design of a *F. falciparum* HRF-deficient (hrfΔ) parasite using the CRISP-Cas9 system. This system that enables to disrupt chromosomal loci is presently applied to generate marker-free locus with deletion of the hrf gene, using a protocol similar to to what was disclosed in reference 46.

DETAILED DESCRIPTION

A. Introduction

While most vaccines against blood-stage malaria in development today use subunit preparations, live attenuated parasites confer significantly broader and more lasting protection. In recent years *Plasmodium* genetically attenuated parasites (GAP) have been generated in rodent models that cause self-resolving blood-stage infections and induce strong protection. All such GAP generated so far bear mutations in house keeping genes important for parasite development in red blood cells.

In prior work the inventors used a *P. berghei* model based on strain *P. berghei* ANKA (PbANKA) in which function of HRF is eliminated. PbANKA causes cerebral malaria in susceptible mice, with lesions starting at day 5 post-infection (p.i.) and mice dying from day 7-8 p.i. Thus, use of this PbANKA precludes study of adaptive immunity. In the context of that model the data suggested that HRF is not important during the erythrocytic phase of infection, but is instead important during the pre-erythrocytic phase of infection, which mainly consists in the transformation in the liver of the mosquito-injected parasite form into the erythrocyte-infecting form. Development of *P. berghei* ANKA c115cyl liver stages lacking HRF is impaired and associated with an early rise in systemic IL-6, a cytokine that strongly suppresses development of *Plasmodium* liver stages.

The inventors generated the data reported in the examples using a different model. Specifically, the inventors have used, as an animal model of malaria, C57BL/6 mice infected with the *P. berghei* NK65 parasite (PbNK65). PbNK65 does not cause cerebral malaria but hyperparasitemia, leading to mouse death by sever anemia around day 25 p.i. This new model is, therefore, compatible with tracking anti-blood stage immune responses over time. Using this new model the inventors were unexpectedly able to demonstrate a novel blood-stage GAP that lacks a secreted factor related to histamine-releasing factor (HRF). Lack of HRF causes IL-6 increase, which boosts T and B cell responses to resolve infection in a cross-stage-, and cross-species-transcendant manner with a long-lasting immunity. Mutant-induced protection involves a combination of anti-parasite IgG2c antibodies and FcγR+ CD11b+ cells phagocytes, especially neutrophils, which are sufficient to confer protection. This immune-boosting GAP highlights an important role of opsonized parasite-mediated phagocytosis, which may be central to protection induced by all self-resolving, blood-stage GAP infections. In order to better understand the molecular basis of the PbNK65 Δhrf-induced protection, the inventors have furthermore analysed CD4+ and CD8+ T cells and memory B cells responses to PbNK65 in C57BL/6J mice in more details.

This disclosed data demonstrate that abortive blood-stage infection leading to lasting protection can be achieved not just by impairing parasite intracellular growth but also by enhancing protective immune responses. Indeed, lack of HRF leads to an increase in IL-6, which does not affect parasite growth per se since PbNK65-hrfΔ blood stages multiply normally in mice until day 10. Rather, IL-6, which is involved in B and T cell differentiation, boosts anti-parasite adaptive responses that clear parasites. Like with previously reported blood-stage GAPs that induce abortive infections, the protective response to PbNK65-hrfΔ parasites is both solid, conferring cross-stage and cross-species immunity, and durable. The inventors have found that the protective response relies on the combination of anti-parasite IgG2c antibodies and FcγR+ CD11b+ cells phagocytic cells, in particular neutrophils, which are sufficient for solid protection. Interestingly, the discovery of a B-helper neutrophil population in the spleen that can act as professional helper cells for marginal zone B-cells (Puga et al., 2012) highlights a neutrophil-B cell interplay that may be critical for B cell differentiation into antibody-producing plasma cells and may also contribute to inhibit the well-known *Plasmodium* capacity to induce short-lived B-cell memory (Wykes et al., 2005). Opsonic phagocytosis was also described as a protective mechanism induced by the plasmepsin-4-deficient mutant (Spaccapelo et al., 2010). Whether this represents the essential protective mechanism common to all self-resolving infections remains to be determined. In addition, by exploring the immunological mechanisms underlying the anti-parasite protective properties of the mutant PbNK65-hrfΔ the inventors have demonstrated that in addition to an up-regulation of IL-6 production, CD4+ but not CD8+ T effector lymphocytes are indispensable for the clearance of malaria infection. Maintenance of T cell-associated protection is associated with the reduction in CD4+PD1+ and CD8+PD1+ T cell numbers. A pivotal role in protection was also conferred by a higher number of central and effector memory B cells observed in mice infected with the mutant parasite. Importantly, the inventors also demonstrated that prior infection with WT parasites followed by a drug cure does not prevent the induction of PbNK65-hrfΔ-induced protection, suggesting that such protection may be efficient even in individuals that have been infected and who repeatedly received antimalarial drugs.

Thus, in a first aspect, the present invention relates to a method of generating an antibody and cellular immune response against a *Plasmodium* in a primate, comprising administering at least $10^3$ genetically modified live *Plasmodium* to the primate, and wherein the infectious genetically modified live *Plasmodium* does not produce functional histamine releasing factor (HRF) protein, to thereby induce an antibody and cellular immune response against the *Plasmodium* in the primate. The *Plasmodium* is preferably capable of developing in primates, and more particularly in humans. In some embodiments the *Plasmodium* belongs to the subgenus selected from the group consisting of *Plasmodium vinckeia*, *Plasmodium plasmodium* and *Plasmodium laverania*. In some embodiments the *Plasmodium* is a species selected from *Plasmodium falciparum*, *Plasmodium vivax*, *Plasmodium ovale*, *Plasmodium malariae*, *Plasmodium knowlesi*, *Plasmodium coatneyi*, *Plasmodium cynomolgi*, and *Plasmodium simium*. According to one embodiment, the *Plasmodium* is capable of developing in a human host and belongs to the subgenus *Plasmodium plasmodium* or *Plasmodium laverania*. Preferably, the *Plasmodium* belongs to a species responsible for malaria in humans, more particularly to a species selected from the group consisting of *Plasmodium falciparum*, *Plasmodium vivax*, *Plasmodium ovale*, *Plasmodium malariae* and *Plasmodium knowlesi*, *Plasmodium coatneyi*, *Plasmodium cynomolgi*, and *Plasmodium simium*. More preferably, the *Plasmodium* belongs to a species selected from *Plasmodium falciparum*, *Plasmodium vivax*, *Plasmodium ovale*, *Plasmodium malariae* and *Plasmodium knowlesi*. According to one particular embodiment, the *Plasmodium* belongs to a species selected from the group consisting of *Plasmodium falciparum*, *Plasmodium vivax* and *Plasmodium malariae*. According to one preferred embodiment, the *Plasmodium* belongs to the species *Plasmodium falciparum*.

According to another embodiment, the *Plasmodium* belongs to a species which is capable of inducing an immune reaction but is not capable of causing the symptoms of malaria in human beings. Preferably, this parasite is a rodent parasite belonging to the subgenus *Plasmodium vinckeia*. The use of rodent parasites in the context of vaccination in humans makes it possible to considerably reduce the risks associated with the administration of live parasites to the subject. The rodent parasite can be modified so as to express one or more proteins of a *Plasmodium* which infects humans, such as *P. falciparum*, which is or are required for the invasion of human red blood cells. Such proteins are, for example, described in the article by Triglia et al., 2000. Preferably, the parasite belongs to the species *Plasmodium berghei* or *Plasmodium yoelii*. More particularly preferably, the parasite belongs to the species *Plasmodium berghei*. According to one preferred embodiment, the parasite is the NK65 isolate of the species *Plasmodium* berghei.

According to another embodiment, the *Plasmodium* belongs to a species selected from the group consisting of *Plasmodium berghei, Plasmodium falciparum, Plasmodium vivax, Plasmodium ovale, Plasmodium malariae* and *Plasmodium knowlesi*. The *Plasmodium* may also belong to a species selected from the group consisting of *Plasmodium berghei, Plasmodium falciparum, Plasmodium vivax, Plasmodium ovale* and *Plasmodium malariae* or from the group consisting of *Plasmodium berghei, Plasmodium falciparum, Plasmodium vivax* and *Plasmodium malariae*, or else from the group consisting of *Plasmodium berghei* and *Plasmodium falciparum*.

In one embodiment, the *Plasmodium* strain doesn't cause cerebral malaria in primates and/or humans.

According to one preferred embodiment, the wild-type strain of the *Plasmodium*, i.e. the *Plasmodium* in which HRF function is not reduced or eliminated, does not cause cerebral malaria. This strain may, for example, be chosen from the group consisting of *Plasmodium berghei* NK65, *Plasmodium* vivax, *Plasmodium* ovale, *Plasmodium malariae* and *Plasmodium knowlesi*. This strain may also be a *Plasmodium falciparum*: strain which has lost its cytoadherence capacity or which has a reduced cytoadherence capacity. According to one embodiment, the wild-type strain of the *Plasmodium* is a non-cytoadherent *Plasmodium falciparum*: strain. According to another embodiment, the wild-type strain of the *Plasmodium* is a *Plasmodium falciparum* strain which has a reduced cytoadherence capacity. Cytoadherence is a property of *Plasmodium falciparum* which is directly linked to the development of cerebral malaria. Indeed, red blood cells infected with a cytoadherent *Plasmodium falciparum* strain have the capacity to bind to surface molecules of endothelial cells, such as CD36, ICAMI, VCAMI or PECAM1/CD31, and thus to cause avascular obstruction, inflammation and damage in various organs, in particular in the brain. The cytoadherence capacity of a strain can be evaluated by any technique known to those skilled in the art, such as, for example, that described in the article by Buffet et al., 1999 or that by Traore et al., 2000. The term "reduced cytoadherence capacity" refers to a cytoadherence capacity which is lower than that observed on a reference cytoadherent *Plasmodium* strain, for example the *Plasmodium falciparum:* 3D7 strain. The cytoadherence can be reduced by at least 40%, 50%, 60%, 70%, 80%, 90% or 95%, preferably by at least 80%, and more particularly preferably by at least 90%, relative to a reference cytoadherent *Plasmodium* strain, for example the *Plasmodium falciparum* 3D7 strain. It is possible to obtain *Plasmodium falciparum*: strains which have a reduced cytoadherence capacity, for example by multiplying the passages in culture ex vivo (Udeinya et al., 1983). Various *Plasmodium falciparum*: strains with a reduced cytoadherence capacity have been described, for example in the article by Trenholme et al., 2000 (*Plasmodium falciparum*: in which the clag9 gene is inactivated) and by Nacer et al., 2011 (*Plasmodium falciparum*: D10 and T9-96). Thus, according to one particular embodiment, the wild-type strain of the *Plasmodium* is a *Plasmodium falciparum* strain which is sparingly cytoadherent or non-cytoadherent. In particular, the wild-type strain of the *Plasmodium* may be a *Plasmodium falciparum*: strain with a reduced cytoadherence capacity, selected from the group consisting of a *Plasmodium falciparum* strain in which the clag9 gene is inactivated, of the *Plasmodium falciparum*: D10 strain and of the *Plasmodium falciparum*: T9-96 strain.

The infectious genetically modified live *Plasmodium* used in the invention does not produce functional histamine releasing factor (HRF) protein. For example, it is possible to block the function of the gene encoding HRF at the transcriptional or translational level or to block HRF function at the protein level, for example by blocking or decreasing the transcription or the translation of the HRF gene or by disrupting the correct folding of the protein or its activity. In a preferred embodiment HRF function is reduced or eliminated by mutating the HRF coding sequence in the genome of the *Plasmodium*.

The function of the HRF gene can in particular be inactivated by the total or partial deletion of this gene, or the insertion or the substitution of one or more nucleotides in order to make this gene inactive. According to one particular embodiment, the function of the HRF gene is inactivated by total or partial deletion of this gene, preferably by total deletion.

Preferably, the deletion of the HRF gene is obtained by homologous recombination. This method is well known to those skilled in the art and has been applied many times to the parasites of the *Plasmodium* genus (see, for example, Thathy and Ménard, 2002). According to one particular embodiment, the coding region of the HRF gene is replaced by homologous recombination with a marker which makes it possible to select the parasites in which the recombination has taken place. The selectable marker may be, for example, the human dihydrofolate reductase (dhfr) gene which confers pyrimethamine resistance on the *Plasmodium*. The obtaining of *Plasmodium* in which the HRF gene is deleted is exemplified in the Examples section. According to one particular embodiment of the invention, the *Plasmodium* used is a *Plasmodium* in which the HRF gene has been replaced with a selectable marker, preferably with the human dhfr gene. According to one very particular embodiment of the invention, the *Plasmodium* is a *Plasmodium berghei*, preferably the NK65 isolate, in which the *Plasmodium* gene has been replaced with a selectable marker, preferably with the human dhfr gene. According to another particular embodiment of the invention, the parasite used is a *Plasmodium falciparum*, which is preferably non-cytoadherent or sparingly cytoadherent, in which the *Plasmodium* gene has been replaced with a selectable marker, preferably with the human dhfr gene. As exemplary method of deleting the HRF gene is presented in the examples section of this application.

The function of the HRF gene can also be inactivated by blocking or decreasing the translation of the mRNA of this gene. RNA interference, which makes it possible to specifically inhibit the expression of the target gene, is a phenomenon well known to those skilled in the art that has already been used to inhibit the expression of *Plasmodium* genes (see, for example, McRobert and McConkey, 2002; Mohmmed et al., 2003; Gissot et al. 2004). According to one embodiment, a sequence encoding an interfering RNA, or its precursor, is introduced into the genome of the parasite and its expression is controlled by a strong promoter, preferably a constitutive promoter, such as, for example, the promoter of the eEF 1 a elongation factor, which is active in all stages of the development of the parasite, or the promoter of the HSP70 gene, which is active in the sporozoites and during the erythrocytic cycle. The sequence and the structure of the interfering RNA can be easily chosen by those skilled in the art. In particular, the interfering RNA used may be a small interfering RNA (siRNA).

It is also feasible to block the function of HRF by introducing mutations in the binding domain to calcium of the protein. Indeed a key function of HRF is its binding to calcium. Deletion constructs of rat TCTP determined that the calcium-binding region of TCTP is confined to residues 81-112 using a 45Ca$^{2+}$-overlay assay (Kim et al., 2000, Identification of the calcium binding sites in translationally controlled tumor protein. Arch Pharm Res 23, 633-6). However, in a recent report the calcium-binding site of human TCTP was determined by NMR, and was found to involve the residues N131, Q133, L149 and D150, with very low affinity (Feng et al., 2007, Feng Y., Liu D., Yao H. and Wang J. (2007) Solution structure and mapping of a very weak calcium-binding site of human translationally controlled tumor protein by NMR. Arch Biochem Biophys 467, 48-57). Mutations in codons of the HFR gene coding for these residues will alter the calcium binding function, which result in profound alterations of HRF biological activities.

One of the important features of mammalian HRF is the binding to immunoglobulins, including IgE. A major Ig-binding site was mapped to the N-terminal 19-residue peptide (N19). A synthetic N19 peptide also inhibited IgE binding to HRF and did not alter the growth or survival of various cells, but it blocked mast cell activation. (Jun-ichi Kashiwakura et al. Histamine-releasing factor has a proinflammatory role in mouse models of asthma and allergy J Clin Invest. 2012 Jan. 3; 122(1): 218-228). Since *Plasmodium* HRF is also endowed with histamine releasing activities from basophils, mutations in or deletion of the 19 N-terminal residues of *Plasmodium* HFR will abrogate this function and render HRF non functional.

In another preferred embodiment of the invention, the deletion of the HRF coding gene is obtained using the CRISPR-Cas9 system as illustrated in FIG. 21. It has indeed been shown in the art (Ghorbal M. et al ref 46 that this system can advantageously be used to disrupt chromosomal loci in *P. falciparum* and to thereby obtain marker-free, single nucleotide substitutions with high efficiency. The technique may be similarly applied to generate *Plasmodium*, in particular *P. falciparum* strain of the invention which encompass a deleted hrf gene or a non-functional version of the hrf gene, i.e. a gene that will display abrogated HRF expression or function. Accordingly in a particular embodiment of the invention, the genetically modified strain of *P. falciparum* suitable for administration to a primate, in particular a human being is a strain provided for administration according to the embodiments disclosed herein, wherein the hrf gene has been disrupted, in particular deleted using the CRISPR-Cas9 system The GenBank and PlasmoDB references of the sequences of HRF genes of various *Plasmodium* species that have been sequenced and also those of the corresponding protein sequences are given in the table below.

| *Plasmodium* Species | GenBank reference number | PlasmoDB reference number |
|---|---|---|
| *P. berghei* ANKA | XM_674443.1 | PBANKA_1110500 |
| *P. chabaudi chabaudi* | XM_737401.1 | PCHAS_1110200 |
| *P. yoelii yoelii* 17X | XM_720179.1 | PY17X_1111700 |
| *P. yoelii* YM | — | PYYM_11112700 |
| *P. falciparum* 3D7 | XM_001351631.1 | PF3D7_0511000 |
| *P. falciparum* IT | — | PFIT_0511100 |
| *P. knowlesi strain* H | XM_002259671.1 | PKNH_1022600 |
| *P. vivax* Sal-1 | XM_001613795.1 | PVX_080685 |
| *P. reichenowi* (strain CDC) | XM_012906171.1 | PRCDC_0510200 |
| *P. cynomolgi* strain B | XM_004222856.1 | — |
| *P. vinckei vinckei* | XM_008626260.1 | — |
| *P. inui* San Antonio 1 | XM_008816858.1 | — |

The HRF genes of the *Plasmodium* species that have not yet been sequenced can be easily identified by means of methods well known to those skilled in the art, in particular by hybridization or PCR.

In the *Plasmodium* according to the invention, the function of one or more genes other than HRF can also be inactivated so that the corresponding functional protein encoded by the gene is not produced. The additional protein/gene of which the function is inactivated can be a gene which participates in the survival of the parasite in a mammalian host, in particular in humans. Preferably, the inactivation of this additional gene makes it possible to attenuate the virulence of the parasite while at the same time preserving its immunogenic nature. This additional gene can be chosen from the group consisting of purine nucleoside phosphorylase (PNP; PFE0660c), nucleoside transporter 1 (NT 1; PF13_0252), UIS3 (PF13_0012), UIS4 (PF10_0164 early transcript), p52, (PFD0215c protein with 6-cysteine motif) and p36 (PFD021 Oc), hmgb2, and also combinations thereof (the references between parentheses are the PlasmoDB bank accession numbers of the *Plasmodium* falciparum: 3D7 sequences, given here by way of example). Preferably the additional gene(s) is or includes hmgb2. Methods of inactivating one or more of these genes are well known in the art and generally include the methods usefol to inactivate the HRF gene as discussed above. Suitable methods are also provided, for example in US 2014/015489 A1.

The methods for growing the *Plasmodium* according to the invention and also the methods of preservation, in particular of cryopreservation, of the *Plasmodium* have been described previously and are well known to those skilled in the art (see, for example, Leef et al., 1979; Orjih et al., 1980). This *Plasmodium* can be grown ex vivo using cell cultures or in vivo in an animal, for example a mouse.

According to one embodiment, the *Plasmodium* according to the invention is used in an erythrocytic form, more particularly in the form of non-intra-erythrocytic merozoites or in the form of intra-erythrocytic merozoites, trophozoites or schizonts.

According to one particular embodiment, the *Plasmodium* according to the invention is used in the form of intra-erythrocytic merozoites, trophozoites or schizonts, i.e. which are inside red blood cells.

According to another particular embodiment, the *Plasmodium* is used in the form of non-intra-erythrocytic merozoites, i.e. of merozoites which have been partially or totally purified after rupturing of parasitized red blood cells. The merozoites can be obtained according to any one of the methods known to those skilled in the art, such as that described in the article by Boyle et al., 2010.

The parasitized red blood cells can be obtained by introduction of the *Plasmodium* into a host, preferably a human-being, and recovery of the red blood cells of the infected host when the parasitaemia reaches a minimum 1%, preferably between 5% and 10%. According to one preferred embodiment, the parasitized red blood cells are recovered from a human host whose blood group is O and who is Rhesus negative.

According to another preferred embodiment, the parasitized red blood cells are obtained by ex vivo infection of human red blood cells, preferably red blood cells which are blood group O and Rhesus negative. Optionally, the parasitized red blood cell cultures can be synchronized so as to obtain predominantly intra-erythrocytic merozoites, trophozoites or schizonts. The methods for ex vivo culturing of *Plasmodium* parasites are well known to those skilled in the art (see, for example, Trager and Jensen, 1976).

Anticoagulants, such as heparin, can be added to the parasitized red blood cells thus obtained. The parasitized red blood cells can be preserved by freezing in the presence of one or more cryoprotective agents compatible with use in vivo, such as, for example, glycerol or dimethyl sulphoxide (DMSO). The parasitized red blood cells can also be preserved by refrigeration at 4° C. in an appropriate preserving medium, for example SAGM ("Saline Adenine Glucose Mannitol") medium or a CPD (Citrate Phosphate Dextrose) solution, but for a period not exceeding approximately 45 days.

According to another embodiment, the parasites according to the invention are used in the form of sporozoites. The sporozoites can be obtained by introduction of the parasite into a mosquito host where it will multiply. The sporozoites are then recovered from the salivary glands of the infected mosquitoes. The sporozoites thus obtained can be preserved by freezing, for example in liquid nitrogen, before being thawed in order to be injected live into a host. Alternatively, after recovery from the salivary glands of the mosquitoes, the sporozoites can be preserved by lyophilization or refrigeration before administration.

The administration of the *Plasmodium* according to the invention to a subject makes it possible, despite a rapid parasite clearance, to induce in the subject an immunity, lasting several months, with respect to an infection with a *Plasmodium*, in particular a *Plasmodium* chosen from *Plasmodium falciparum*, *Plasmodium vivax*, *Plasmodium ovale*, *Plasmodium malariae* and *Plasmodium knowlesi*, *Plasmodium coatneyi*, *Plasmodium cynomolgi*, and *Plasmodium simium*. In some embodiments the *Plasmodium* is chosen from the group consisting of *Plasmodium falciparum*, *Plasmodium vivax*, *Plasmodium malariae* and *Plasmodium knowlesi*, preferably *Plasmodium falciparum*. This immunity can in particular be a cross-immunity with respect to an infection with a *Plasmodium* strain other than that of the parasite used. In particular, the administration of a parasite according to the invention belonging to a strain which does not cause cerebral malaria can result in a cross-immunity with respect to an infection with a *Plasmodium* strain capable of causing this severe neurological complication. The parasite according to the invention can therefore be used for the prevention of malaria and/or of cerebral malaria. In particular, the administration of the parasite according to the invention to a subject makes it possible to induce an immunity, lasting several months, with respect to an infection with a *Plasmodium falciparum* capable of inducing cerebral malaria and thus to prevent malaria and/or cerebral malaria induced by this parasite.

The methods of the invention typically comprise administration of at least $10^3$ genetically modified live *Plasmodium* to a primate per dose. In some embodiments from $10^3$ to $10^8$ genetically modified live *Plasmodium* is administered to a primate per dose. In some embodiments from $10^4$ to $10^8$ genetically modified live *Plasmodium* is administered to a primate per dose. In some embodiments from $10^3$ to $10^5$ genetically modified live *Plasmodium* is administered to a primate per dose. In some embodiments from $10^4$ to $10^6$ genetically modified live *Plasmodium* is administered to a primate per dose. In some embodiments from $10^5$ to $10^7$ genetically modified live *Plasmodium* is administered to a primate per dose. In some embodiments from $10^4$ to $10^5$ genetically modified live *Plasmodium* is administered to a primate per dose. In some embodiments at least $10^3$ genetically modified live *Plasmodium* is administered to a primate per dose. In some embodiments at least $10^4$ genetically modified live *Plasmodium* is administered to a primate per dose. In some embodiments at least $10^5$ genetically modified live *Plasmodium* is administered to a primate per dose. In some embodiments at least $10^6$ genetically modified live *Plasmodium* is administered to a primate per dose.

In some embodiments the immunogenic composition is administered from one to five times, such as one time, two times, three times, four times, or five times. In some embodiments comprising a plurality of administrations the doses are administered over a period of 30 days, 60 days, 90 days, one year or more than one year. In some embodiments a dose is administered annually.

In a particular embodiment, the administered genetically modified live *Plasmodium* is *P. falciparum* and it is administered to a human being.

In some embodiments of the methods, the likelihood that the primate will develop *Plasmodium* parasitemia following challenge with a wild type live *Plasmodium* is reduced by at least 50% for a period of at least 68 days following administration of the genetically modified live *Plasmodium*. In some embodiments of the methods, the likelihood that the primate will develop *Plasmodium* parasitemia following challenge with a wild type live *Plasmodium* is reduced by at least 75% for a period of at least 68 days following administration of the genetically modified live *Plasmodium*. In some embodiments of the methods, the likelihood that the primate will develop *Plasmodium* parasitemia following challenge with a wild type live *Plasmodium* is reduced by at least 80% for a period of at least 68 days following administration of the genetically modified live *Plasmodium*. In some embodiments of the methods, the likelihood that the primate will develop *Plasmodium* parasitemia following challenge with a wild type live *Plasmodium* is reduced by at least 85% for a period of at least 68 days following administration of the genetically modified live *Plasmodium*. In some embodiments of the methods, the likelihood that the primate will develop *Plasmodium* parasitemia following challenge with a wild type live *Plasmodium* is reduced by at least 90% for a period of at least 68 days following administration of the genetically modified live *Plasmodium*. In some embodiments of the methods, the likelihood that the primate will develop *Plasmodium* parasitemia following challenge with a wild type live *Plasmodium* is reduced by at least 95% for a period of at least 68 days following administration of the genetically modified live *Plasmodium*.

In some embodiments of the methods, the likelihood that the primate will develop *Plasmodium* parasitemia following challenge with a wild type live *Plasmodium* is reduced by at least 50% for a period of at least 396 days following administration of the genetically modified live *Plasmodium*. In some embodiments of the methods, the likelihood that the primate will develop *Plasmodium* parasitemia following challenge with a wild type live *Plasmodium* is reduced by at least 75% for a period of at least 396 days following administration of the genetically modified live *Plasmodium*. In some embodiments of the methods, the likelihood that the primate will develop *Plasmodium* parasitemia following challenge with a wild type live *Plasmodium* is reduced by at least 80% for a period of at least 396 days following administration of the genetically modified live *Plasmodium*. In some embodiments of the methods, the likelihood that the primate will develop *Plasmodium* parasitemia following challenge with a wild type live *Plasmodium* is reduced by at least 85% for a period of at least 396 days following administration of the genetically modified live *Plasmodium*. In some embodiments of the methods, the likelihood that the primate will develop *Plasmodium* parasitemia following challenge with a wild type live *Plasmodium* is reduced by at least 90% for a period of at least 396 days following administration of the genetically modified live *Plasmodium*. In some embodiments of the methods, the likelihood that the primate will develop *Plasmodium* parasitemia following challenge with a wild type live *Plasmodium* is reduced by at least 95% for a period of at least 396 days following administration of the genetically modified live *Plasmodium*.

In some embodiments of the methods, the likelihood that the primate will develop a blood stage *Plasmodium* infection following challenge with a wild type live *Plasmodium* is reduced by at least 50% for a period of at least 25 days following administration of the genetically modified live *Plasmodium*. In some embodiments of the methods, the likelihood that the primate will develop a blood stage *Plasmodium* infection following challenge with a wild type live *Plasmodium* is reduced by at least 75% for a period of at least 25 days following administration of the genetically modified live *Plasmodium*. In some embodiments of the methods, the likelihood that the primate will develop a blood stage *Plasmodium* infection following challenge with a wild type live *Plasmodium* is reduced by at least 80% for a period of at least 25 days following administration of the genetically modified live *Plasmodium*. In some embodiments of the methods, the likelihood that the primate will develop a blood stage *Plasmodium* infection following challenge with a wild type live *Plasmodium* is reduced by at least 85% for a period of at least 25 days following administration of the genetically modified live *Plasmodium*. In some embodiments of the methods, the likelihood that the primate will develop a blood stage *Plasmodium* infection following challenge with a wild type live *Plasmodium* is reduced by at least 90% for a period of at least 25 days following administration of the genetically modified live *Plasmodium*. In some embodiments of the methods, the likelihood that the primate will develop a blood stage *Plasmodium* infection following challenge with a wild type live *Plasmodium* is reduced by at least 95% for a period of at least 25 days following administration of the genetically modified live *Plasmodium*.

In some embodiments of the methods, the antibody and cellular immune response generated by the administration of genetically modified live *Plasmodium* to the primate is a protective immune response of Th1 type.

In some embodiments of the methods administering the genetically modified live *Plasmodium* to the primate induces an increase of at least 50% in plasma IL-6. In some embodiments of the methods administering the genetically modified live *Plasmodium* to the primate induces an increase of at least 100% in plasma IL-6. In some embodiments of the methods administering the genetically modified live *Plasmodium* to the primate induces an increase of at least 150% in plasma IL-6. In some embodiments of the methods administering the genetically modified live *Plasmodium* to the primate induces an increase of at least 200% in plasma IL-6.

In some embodiments of the methods administering the genetically modified live *Plasmodium* to the primate induces a decrease of at least 50% in spleen PD1+ T cells, preferably in spleen PD1+ CD8+ CD62L− cells and spleen PD1+CD4+ CD62L− cells.

In some embodiments of the methods the antibody response generated by the administration of genetically modified live *Plasmodium* to the primate consists in antibodies against parasite proteins from wild type *Plasmodium*-infected red blood cells. Preferably, parasite proteins recognized by the produced antibodies are merozoite surface protein 1 (MSP1), serine repeat antigen 1 (SERA1) and 2 (SERA2), Rhoptry protein (RhopH3) and octopeptide-repeat antigen.

In some embodiments of the methods, the cellular immune response generated by the administration of genetically modified live *Plasmodium* to the primate comprises phagocytic cells, and preferably FcγR+ CD11b+ phagocytic cells, and more preferably neutrophils.

In some embodiments of the methods the antibody response is detectable by Western blot, for example by using the method disclosed in the examples.

In some embodiments of the methods the antibody response is detectable by ELISA, for example by using the method disclosed in the examples.

In another aspect, the present invention relates to an immunogenic composition for administration to a primate, comprising a at least $10^3$ genetically modified live *Plasmodium*, wherein the infectious genetically modified live *Plasmodium* does not produce functional histamine releasing factor (HRF) protein; and at least one pharmaceutically acceptable excipient and/or support. The *Plasmodium* included in the composition is as described above.

According to one embodiment, the composition comprises a *Plasmodium* according to the invention in an erythrocytic form, more particularly in the form of intra-erythrocytic merozoites, trophozoites or schizonts or of non-intra-erythrocytic merozoites, preferably in the form of intra-erythrocytic merozoites, trophozoites or schizonts.

In some embodiments the composition comprises red blood cells parasitized with the *Plasmodium* according to the invention and which can be obtained according to the method described above and in the experimental section.

In some embodiments the *Plasmodium* included in the composition is in the form of sporozoites as described above.

In some embodiments the immunogenic composition is capable of inducing, in the subject to whom it is administered, a response of the immune system against the *Plasmodium* that it contains. In a particular embodiment, the immunogenic composition is intended for administration to a human being and it comprises *P. falciparum* forms as described herein.

The immunogenic compositions of the invention typically comprise at least $10^3$ genetically modified live *Plasmodium* per dose. In some embodiments the immunogenic compositions of the invention comprise from $10^3$ to $10^8$ genetically modified live *Plasmodium* per dose. In some embodiments the immunogenic compositions of the invention comprise from $10^4$ to $10^8$ genetically modified live *Plasmodium* per dose. In some embodiments the immunogenic compositions of the invention comprise from $10^3$ to $10^5$ genetically modified live *Plasmodium* per dose. In some embodiments the immunogenic compositions of the invention comprise from $10^4$ to $10^6$ genetically modified live *Plasmodium* per dose. In some embodiments the immunogenic compositions of the invention comprise from $10^1$ to $10^7$ genetically modified live *Plasmodium* per dose. In some embodiments the immunogenic compositions of the invention comprise from $10^4$ to $10^5$ genetically modified live *Plasmodium* per dose. In some embodiments the immunogenic compositions of the invention comprise at least $10^3$ genetically modified live *Plasmodium* per dose. In some embodiments the immunogenic compositions of the invention comprise at least $10^4$ genetically modified live *Plasmodium* per dose. In some embodiments the immunogenic compositions of the invention comprise at least $10^5$ genetically modified live *Plasmodium* per dose. In some embodiments the immunogenic compositions of the invention comprise at least $10^6$ genetically modified live *Plasmodium* per dose.

In preferred embodiments the immunogenic composition is used according to a method of the invention and is active therein. For example, in some embodiments of the immunogenic composition, the likelihood that a primate will develop *Plasmodium* parasitemia following challenge with a wild type live *Plasmodium* is reduced by at least 50% for a period of at least 68 days following administration of the immunogenic composition to the primate. In some embodiments of the immunogenic compositions, the likelihood that a primate will develop *Plasmodium* parasitemia following challenge with a wild type live *Plasmodium* is reduced by at least 75% for a period of at least 68 days following administration of the immunogenic compositions. In some embodiments of the immunogenic compositions, the likelihood that a primate will develop *Plasmodium* parasitemia following challenge with a wild type live *Plasmodium* is reduced by at least 80% for a period of at least 68 days following administration of the immunogenic compositions. In some embodiments of the immunogenic compositions, the likelihood that a primate will develop *Plasmodium* parasitemia following challenge with a wild type live *Plasmodium* is reduced by at least 85% for a period of at least 68 days following administration of the immunogenic compositions. In some embodiments of the immunogenic compositions, the likelihood that a primate will develop *Plasmodium* parasitemia following challenge with a wild type live *Plasmodium* is reduced by at least 90% for a period of at least 68 days following administration of the immunogenic compositions. In some embodiments of the immunogenic compositions, the likelihood that a primate will develop *Plasmodium* parasitemia following challenge with a wild type live *Plasmodium* is reduced by at least 95% for a period of at least 68 days following administration of the immunogenic compositions.

In some embodiments of the immunogenic composition, the likelihood that a primate will develop *Plasmodium* parasitemia following challenge with a wild type live *Plasmodium* is reduced by at least 50% for a period of at least 396 days following administration of the immunogenic composition to the primate. In some embodiments of the immunogenic compositions, the likelihood that a primate will develop *Plasmodium* parasitemia following challenge with a wild type live *Plasmodium* is reduced by at least 75% for a period of at least 396 days following administration of the immunogenic compositions. In some embodiments of the immunogenic compositions, the likelihood that a primate will develop *Plasmodium* parasitemia following challenge with a wild type live *Plasmodium* is reduced by at least 80% for a period of at least 396 days following administration of the immunogenic compositions. In some embodiments of the immunogenic compositions, the likelihood that a primate will develop *Plasmodium* parasitemia following challenge with a wild type live *Plasmodium* is reduced by at least 85% for a period of at least 396 days following administration of the immunogenic compositions. In some embodiments of the immunogenic compositions, the likelihood that a primate will develop *Plasmodium* parasitemia following challenge with a wild type live *Plasmodium* is reduced by at least 90% for a period of at least 396 days following administration of the immunogenic compositions. In some embodiments of the immunogenic compositions, the likelihood that a primate will develop *Plasmodium* parasitemia following challenge with a wild type live *Plasmodium* is reduced by at least 95% for a period of at least 396 days following administration of the immunogenic compositions.

In some embodiments of the immunogenic compositions, the likelihood that a primate will develop a blood stage *Plasmodium* infection following challenge with a wild type live *Plasmodium* is reduced by at least 50% for a period of at least 25 days following administration of the immunogenic compositions. In some embodiments of the immunogenic compositions, the likelihood that a primate will develop a blood stage *Plasmodium* infection following challenge with a wild type live *Plasmodium* is reduced by at least 75% for a period of at least 25 days following administration of the immunogenic compositions. In some embodiments of the immunogenic compositions, the likelihood that a primate will develop a blood stage *Plasmodium* infection following challenge with a wild type live *Plasmodium* is reduced by at least 80% for a period of at least 25 days following administration of the immunogenic compositions. In some embodiments of the immunogenic compositions, the likelihood that a primate will develop a blood stage *Plasmodium* infection following challenge with a wild type live *Plasmodium* is reduced by at least 85% for a period of at least 25 days following administration of the immunogenic compositions. In some embodiments of the immunogenic compositions, the likelihood that a primate will develop a blood stage *Plasmodium* infection following challenge with a wild type live *Plasmodium* is reduced by at least 90% for a period of at least 25 days following administration of the immunogenic compositions. In some embodiments of the immunogenic compositions, the likelihood that a primate will develop a blood stage *Plasmodium* infection following challenge with a wild type live *Plasmodium* is reduced by at least 95% for a period of at least 25 days following administration of the immunogenic compositions.

In some embodiments of the immunogenic compositions, administering the immunogenic compositions to a primate induces an increase of at least 50% in plasma IL-6. In some embodiments of the immunogenic compositions administering the immunogenic compositions to a primate induces an increase of at least 100% in plasma IL-6. In some embodiments of the immunogenic compositions administering the immunogenic compositions to a primate induces an increase of at least 150% in plasma IL-6. In some embodiments of the immunogenic compositions administering the immunogenic compositions to a primate induces an increase of at least 200% in plasma IL-6.

In some embodiments of the immunogenic compositions, administering the immunogenic compositions to the primate induces a decrease of at least 50% in spleen PD1+ T cells, preferably in spleen PD1+CD8+ CD62L− cells and spleen PD1+CD4+CD62L− cells.

In some embodiments of the immunogenic compositions administering the immunogenic compositions to a primate induces an antibody response that is detectable by Western blot, for example by using the method disclosed in the examples.

In some embodiments of the immunogenic compositions administering the immunogenic compositions to a primate induces an antibody response that is detectable by ELISA, for example by using the method disclosed in the examples.

Preferably, the immunogenic composition is a malaria vaccine. In particular it is a malaria vaccine against *P. falciparum* for administration to a human being. In particular it is a malaria vaccine against *P. falciparum* that comprises *P. falciparum* forms as described herein.

According to some embodiments, the composition according to the invention is obtained by suspending parasitized red blood cells, merozoites or sporozoites, preferably parasitized red blood cells or sporozoites, as defined above, in one or more pharmaceutically acceptable excipients. The excipients can be easily chosen by those skilled in the art according to the form of the parasite, intra-erythrocytic, merozoites or sporozoites, and according to the route of administration envisaged. These excipients can in particular be chosen from the group consisting of sterile water, sterile physiological saline and phosphate buffer. Other excipients well known to those skilled in the art can also be used. Preferably, in the case where the composition comprises parasitized red blood cells, the excipient used is an isotonic solution which ensures the integrity of the red blood cells until administration of the composition to the subject. Preferably, the composition also comprises at least one anticoagulant such as heparin.

The composition can also be obtained by mixing *Plasmodium* sporozoites, as defined above, in particular *P. falciparum* sporozoites with a pharmaceutically acceptable support such as, for example, liposomes.

The excipients or supports used are chosen so as to ensure the integrity of the parasitized red blood cells and/or the survival of the sporozoites or of the merozoites. The excipients or supports used are chosen so as to ensure the survival of the parasites of the invention, whatever the form used (merozoites, sporozoites or intra-erythrocytic forms), until the administration of the composition to the subject to be immunized.

The composition according to the invention may be administered, for example, parenterally, cutaneously, mucosally, transmucosally or epidermally. Preferably, the composition is formulated so as to be administered parenterally, in particular subcutaneously, intramuscularly, intravenously or intradermally.

According to one particular embodiment, the *Plasmodium* is in an erythrocytic form, preferably included in red blood cells, and the composition is formulated so as to be administered parenterally, preferably subcutaneously, intramuscularly, intravenously or intradermally, and quite particularly preferably intravenously.

According to another particular embodiment, the *Plasmodium* is in the form of sporozoites and the composition is formulated so as to be administered parenterally, preferably subcutaneously, intramuscularly or intradermally, preferably intramuscularly or subcutaneously. The methods for administering compositions comprising live sporozoites are well known to those skilled in the art (see, for example, international patent application WO 2004/045559, Hoffman et al., 2010, Gueirard et al., 2010).

According to one embodiment, the *Plasmodium* is in erythrocytic form and included in red blood cells.

According to another embodiment, the *Plasmodium* is in the form of non-intra-erythrocytic merozoites.

According to yet another embodiment, the *Plasmodium* is in the form of sporozoites.

The dose to be administered can be easily determined by those skilled in the art by taking into account the physiological data of the subject to be immunized, such as the age or immune state thereof, the degree of immunity desired, the number of doses administered and the route of administration used. The dose to be administered can also vary according to the parasite preservation mode.

The composition according to the invention may comprise one or more strains of *Plasmodium* according to the invention. According to one embodiment, the composition comprises at least one *Plasmodium falciparum* strain and one *Plasmodium vivax* strain in which the function of the HRF gene is inactivated.

The composition according to the invention may also comprise one or more other genetically attenuated *Plasmodium*. These *Plasmodium* may, for example, exhibit a modification or an inactivation of the function of the purine nucleoside phosphorylase gene, nucleoside transporter 1, UIS3, UIS4, p52, p36, or hmgb2 gene, or be attenuated parasites obtained by irradiation. These *Plasmodium* preferably belong to a strain selected from the group consisting of *Plasmodium falciparum*, *Plasmodium vivax*, *Plasmodium ovale*, *Plasmodium malariae* and *Plasmodium knowlesi*, *Plasmodium coatneyi*, *Plasmodium cynomolgi*, and *Plasmodium simium*. In a particular embodiment the *Plasmodium* preferably belong to *P. falciparum*.

The composition according to the invention may also comprise one or more immunological adjuvants. These adjuvants stimulate the immune system and thus reinforce the immune response obtained with respect to the parasite according to the invention. These immunological adjuvants comprise, without being limited thereto, adjuvants of muramyl peptide type, such as N-acetylmuramyl-L-alanyl-D-isoglutamine (MDP) and derivatives thereof; trehalose dimycolate (TDM); lipopolysaccharide (LPS); monophosphoryl lipid A (MPL); carboxymethylcellulose; complete Freund's adjuvant; incomplete Freund's adjuvant; adjuvants of "oil-in-water" emulsion type optionally supplemented with squalene or squalane; mineral adjuvants such as alum, aluminium hydroxide, aluminium phosphate, potassium phosphate or calcium phosphate; bacterial toxins such as cholera toxin subunit B, the inactivated form of pertussis toxin or the thermolabile lymphotoxin from *Escherichia coli*; CpG oligodeoxynucleotides; saponins; synthetic copolymers such as copolymers of polyoxyethylene (POE) and polyoxypropylene (POP); cytokines; or imidazoquinolones. Combinations of adjuvants may be used. These various types of adjuvants are well known to those skilled in the art. In particular, the composition according to the invention may comprise one or more immunological adjuvants selected from the group consisting of CpG oligodeoxynucleotides and mineral adjuvants, in particular alum, and a combination thereof.

According to another aspect, the invention relates to the use of a live *Plasmodium* genus in which the function of the HRF gene is reduced or inactivated, for preparing a vaccine composition against malaria or cerebral malaria.

The invention also relates to a method for producing a vaccine composition against malaria or cerebral malaria according to the invention.

The invention also relates to an immunogenic composition as defined in any of the herein described embodiments, for use as an immunogenic protective composition in a primate, in particular in a human, against clinical malaria.

The immunogenic composition of the invention is in particular for use as an immunogenic protective composition in a primate, in particular in a human wherein said primate is naive for *Plasmodium* infection.

In a particular embodiment, the immunogenic composition of the invention is for use in a primate, in particular in a human, wherein the primate has been previously therapeutically treated against malaria, said composition being protective against subsequent infection by a *plasmodium* parasite.

In a particular embodiment, the immunogenic composition of the invention is for use in a primate, in particular in a human, as a cross-stage and cross-species protective composition against *Plasmodium* infection or against malaria.

The invention also relates to a process of preparing an immunogenic composition according to the invention wherein said composition is suitable for generating an immune response, in particular an antibody response against a *Plasmodium* in a primate, wherein the process comprises admixing at least $10^3$ genetically modified live *Plasmodium* wherein the genetically modified live *Plasmodium* is a species selected from *Plasmodium falciparum*, *Plasmodium vivax*, *Plasmodium ovale*, *Plasmodium malariae*, *Plasmodium knowlesi*, *Plasmodium coatneyi*, *Plasmodium cynomolgi*, and *Plasmodium simium*, and wherein the genetically modified live *Plasmodium* does not produce functional histamine releasing factor (HRF) protein; and at least one pharmaceutically acceptable excipient and/or support. In particular, the *Plasmodium* species is *P. falciparum*.

According to one embodiment, the method comprises mixing red blood cells infected with a live parasite according to the invention, with one or more pharmaceutically acceptable excipients or supports. Preferably, the red blood cells are human red blood cells obtained from a host whose blood group is O and who is Rhesus negative.

According to another embodiment, the method comprises mixing live non-intra-erythrocytic merozoites of a parasite according to the invention with one or more pharmaceutically acceptable excipients or supports.

According to another embodiment, the method comprises mixing live sporozoites of a parasite according to the invention with one or more pharmaceutically acceptable excipients or supports.

According to another embodiment, the *Plasmodium*, in the form of parasitized red blood cells, or of merozoites or in the form of sporozoites, is also mixed with one or more immunological adjuvants. These adjuvants may be as defined above.

The method may also comprise a prior step comprising the obtaining of said parasitized red blood cells, of said merozoites or of said sporozoites, for example using the methods described above.

The composition or the vaccine obtained can be preserved before administration, for example frozen or refrigerated if it contains parasitized red blood cells, or frozen, refrigerated or lyophilized if it contains sporozoites or merozoites. Preferably, the composition or the vaccine obtained is preserved frozen before administration. In the case of lyophilization, an appropriate diluent is added to the lyophilisate before administration, for instance sterile water or sterile physiological saline, preferably sterile physiological saline.

The various embodiments concerning the *Plasmodium* and the composition according to the invention are also envisaged in this aspect.

According to another aspect, the invention relates to a method for immunizing a subject against malaria, comprising the administration of an immunogenic composition or of a vaccine according to the invention to said subject. Preferably, the subject is a human being.

The immunity of the subject with respect to malaria or to cerebral malaria may be total or incomplete. In the case of incomplete immunity, the seriousness of the symptoms of the established disease in an immunized subject will be reduced by comparison with those observed in a non-immunized subject. In the case of total immunity, the immunized subject will show no symptom of the disease after a contact with the parasite.

According to one preferred embodiment, the immunity obtained by administering the composition according to the invention is a sterile immunity. This means that the development of the parasites administered is highly modified and that, approximately 2 to 4 weeks after the administration, the parasites are no longer detected in the subject's peripheral blood.

The invention also relates to a method for immunizing a subject against malaria, comprising the administration of a parasite according to the invention in the form of sporozoites to said subject by means of bites by mosquitoes infected with said parasite. In particular, the administered *Plasmodium* species is *P. falciparum*.

The examples which follow are given for illustrative and non-limiting purposes.

EXAMPLES

I. Protection Against Malaria in Mice is Induced by Blood Stage—Arresting HRF—Deficient Parasites

Example 1: Materials and Methods

Rodents. Five- to eight-week-old wild-type female C57BL/6J Rj and Swiss Webster (SW) mice were purchased from Janvier laboratory (Le Genest-Saint-Isle, France). Transgenic T cell-deficient (CD3K$^0$), B cell-deficient (secretory p chain [μsK$^0$]), Feγ receptor-deficient (FcγRK$^0$), and IL-6Ko mice strains were kindly provided by Dr B. Ryffel (Institut Pasteur, Paris, France), Dr. J M. Cavaillon (Institut Pasteur, Paris, France), Dr. P. Bruhns (Institut Pasteur, Paris, France), and Dr. Lionel Apetoh (INSERM U866, Dijon, France), respectively. CD11c-DTR-GFP mice (Jung et al., 2002) have been used to explore the role of DCs in controlling parasite development. Transgenic mice have all been back-crossed ten times on C57BL/6 mice from The Jackson Laboratory.

Parasites. Mice were inoculated with red blood cells infected (iRBCs) with either *Plasmodium berghei* (Pb) NK65 wild-type or mutant (hrfΔ1) GFP-transgenic parasites. In a few control experiments, mice were infected with *P. yoelii* YM or Pb ANKA-GFP iRBCs, or with PbNK65 or PbANKA GFP-transgenic sporozoites collected from salivary glands of infected *Anopheles stephensi*.

Mouse infections and immunization with blood stages. Cryopreserved *P. berghei* parasites were passaged once through SW mice before being used to infect experimental animals. Mice were infected with blood stages of either GFP-transgenic PbNK65 or PbNK65-hrfiJ1 or PbNK65-hrf12 parasites by injecting 105, 104 or 103 infected red blood cells (iRBCs) intraperitoneally (i.p.). After injection, blood samples were taken daily from the tail and parasitemia assessed by flow cytometry. If mice did not develop parasites after challenge, they were recorded as completely protected.

Splenic index. Spleens from uninfected and infected mice were harvested at day 6 post-infection with WT or PbNK65-hrfiJ1 parasites. The splenic index for each individual mouse was calculated as follows: spleen weight (mg)/body weight (mg)×100.

Sporozoite development in HepG2 cells. HepG2 cells (2-3.0×104/well) were plated in eight-well chamber slides (Lab-Tek® Chamber Slide™) and cultured overnight in DMEM+GlutaMAX-lmedia (Gibco) supplemented with 10% heat inactivated FBS (Fetal Bovine Serum, Gibco) at 37° C. in the presence of 5% C02. Wild type or mutant purified P. berghei salivary gland sporozoites were used for HepG2 infection at a ratio of 1:1 (parasite/cells) for 36 h at 37° C., 5% C02 in the presence of PSN (Penicillin-Streptomycin-Neomycin solution, Sigma-Aldrich; St. Louis, Mo.). PbH RF was detected by immunofluorescence staining as described below.

Immunofluorescence assays (IFAs) for the intracellular detection of HRF. Fixation and permeabilization of sporozoites, infected HepG2 cells, iRBCs and purified gametocytes was performed using 4% paraformaldehyde (PFA) and 0.1% Triton X-100, and blocked with 1-3% gelatin from porcine skin (Sigma-Aldrich; St. Louis, Mo.). Thereafter, cells were incubated with specific rabbit anti-HRF antibodies (diluted 1:500) (Mathieu et al., 2015), and then incubated with Alexa 568-conjugated secondary antibodies (Life technologies, diluted 1:500) and 0.02 mg/ml 4', 6-diamidino-2-phenylindole (DAPI) for nuclear staining. The expression of PbHRF was detected using the fluorescence microscope AxioVert 200 (Carl Zeiss).

Preparation of total RNA and reverse transcription-quantitative PCR (RT-qPCR) analysis of mRNA. The spleens and livers of C57BL/6J mice infected with WT or PbNK65-hrfil1 parasites were surgically removed 40 h p.i. or at day 2, 4, 6, 8, 10, 12, 14 and 20 p.i., respectively. Total RNAs were extracted from the spleen as well from the liver samples using the Guanidinium-thiocyanate-phenol-chloroform method (all Invitrogen, Waltham, Mass., USA). RNA was thereafter reverse transcribed by PCR (temperature profile: 65° C. for 5 min, 42° C. for 50 min, 70° C. for 15 min) using 100 U SuperScript™ II reverse transcriptase (RT) (Invitrogen, Waltham, Mass., USA), 40 U RNAse Inhibitor and 2 µM oligo(dT) 18S rRNA primer (Eurofins MWG Operon, Ebersberg, Germany) per sample. The expression levels of diverse transcripts were analyzed by real time RT-qPCR using Power SYBR® Green PCR Master Mix (Applied Biosystems Poster City, Calif., USA) and various primers sets (see table 1). All reactions were performed in the ABI PRISM 7000 Sequence Dectection System Real Time PCR machine (temperature profile: 50° C. for 2 min, 95° C. for 10 min, 40 cycles of 95° C. for 15 s and 60° C. for 1 min). The relative abundance of parasite and cytokines rRNA in the spleen was calculated using the $\Delta C_t$ method, and expressed as $2^{-\Delta C}$. The mouse hypoxanthine phosphoribosyltransferase (HPRT) gene was used as an internal control for the variation in input RNA amounts. No template control (NTC) was included to ensure that there was no cross-contamination during sample preparation.

TABLE 1

List of oligonucleotides used for RT-qPCR analyses (5'-3').

| Primer | Fw/Rev | Sequence | SEQ ID No |
|---|---|---|---|
| Pb 18S | Fw | ATTAATCTTGAACGAGGAATGGCT | 1 |
|  | Rev | TCAATCGGTAGGAGCGACG | 2 |
| PbLSP2 | Fw | GCCAAATGCTAAACCTAATG | 3 |
|  | Rev | TGGGTTTGTATTGTATGCAC | 4 |
| PbHSP70 | Fw | TGCAGCTAATCAAACTC | 5 |
|  | Rev | ACTTCAATTTGTGGAACACC | 6 |
| mu IL-23 | Fw | CCACCAGGACTCAAGGACAACA | 7 |
|  | Rev | GCAGGCTCCCCTTTGAAGA | 8 |
| mu EBB | Fw | CAGAGTGCAATGCCATGCTCC | 9 |
|  | Rev | GCCACACCGAGCCTGTAAGT | 10 |
| muIL-12p35 | Fw | TACTAGAGAGACTTCTTCCACAACAAGAG | 11 |
|  | Rev | GATTCTGAAGTGCTGCGTTGAT | 12 |
| mu IL-12p40 | Fw | GGAAGCACGGCAGCAGAATA | 13 |
|  | Rev | AACTTGAGGGAGAAGTAGGAATGG | 14 |
| mu IFN-y | Fw | AAAGGATGCATTCATGAGTATTGC | 15 |
|  | Rev | CGCTTCCTGAGGCTGGATT | 16 |
| mu IL-6 | Fw | AAAGAAATGATGGATGCTACCAAAC | 17 |
|  | Rev | CTTGTTATCTTTTAAGTTGTTCTTCATGTACTC | 18 |
| mu IL-10 | Fw | GGCGCTGTCATCGATTTCTC | 19 |
|  | Rev | GACACCTTGGTCTTGGAGCTTATTAA | 20 |
| mu HPRT | Fw | CTGGTGAAAAGGACCTCTCG | 21 |
|  | Rev | TGAAGTACTCATTATAGTCAAGGGCA | 22 |

Flow cytometry analysis of spleen leukocytes. Spleens were mechanically disrupted in 2 ml PBS and cells were filtered through a 70-mm strainer (BD Falcon). Erythrocytes were lysed using Gey's solution for 5 min on ice and washed twice in PBS. Single-cell suspensions were stained for FACS analysis according to standard protocols in cold PBS containing 2% FCS and 0.01% sodium azide (FACS buffer) with the following antibodies: phycoerythrin (PE)-labelled anti-CD4, phycoerythrin-Cy5 (PeCy5)-labelled anti-CD45, allo-phyco-cyanine (APC)-labelled anti-CD8, fluorescein isothiocyanate (FITC)-labelled anti-CD11b, APC-labelled anti-CD11c, APC-labelled anti-Ly6G, PeCy5-labelled anti-F4/80 and PE-labelled anti-IL-6 antibodies (all antibodies from BD Biosciences, Mountain View, Calif.). A total of 5×105 living cells were analyzed using a four-colour FACSCalibur flow cytometer (Becton Dickinson, Grenoble, France) and ProCellQuest software (BD Biosciences, Mountain View, Calif.).

In vivo cell depletion. For neutrophils depletion, C57BL/6 mice were injected with 500 µg of a rat anti-mouse neutrophils (clone NIMP-R14) provided by G. Milon (Institut Pasteur, Paris) at day 2 and day 4 post infection with PbNK65-hrfL41. For systemic DC depletion, CDIIc-DTR-GFP transgenic mice were injected i.p. with 5.2 ng/g body weight diphteria toxin (DTX) (Sigma Chemical Co., St. Louis, Mo., USA) in PBS at day 2 and 4 after infection with PbNK65-hrfL41. To determine if CD3 plays a role in the anti-parasitic memory response developed by protected mice, cell-specific depletion experiments were performed. C57BL/6J Rj protected mice were injected i.p. with 20 µg of anti-CD3 clone 145-2C11 Armenian hamster IgG (eBioscience, San Diego, Calif.) 24 h before the infection with PbNK65 WT and 48 h after the infection. The cell depletion was followed and confirmed by flow cytometry. Before the infection and every day p.i., 10 µl of blood were collected from the tip of the mouse tail and analyzed to confirm neutrophils, DCs, and CD3 cell depletion, by FACS analysis.

Detection of specific IgG antibodies and IL6 cytokine in the serum of infected mice. To detect parasite-specific antibodies, protein extracts from blood stages obtained by saponin lysis (0.1%) of parasite pellets were sonicated in lysis buffer (10 mM Tris pH 7.4, 150 mM NaCl, 0.02% NaN3, 20 mM $MgCl_2$, 1% Triton X-100, and complex protease inhibitors) and centrifuged (10,000 g for 30 min at 4° C.). The total amount of proteins in the supernatant was measured using a Bio-Rad protein assay. 96-well plates (Nunc-immuno plate; Thermo Scientific, Rockford, Ill.) were coated with PbNK 65 WT protein extracts (2 µg/ml) in carbonate buffer, pH 9.6, for 2 h at 37° C. and then saturated with 1% (w/v) BSA (Bovine Serum Albumin, Sigma-Aldrich; St. Louis, Mo.). Serum samples were assayed using serial dilutions and incubated for 2 h at 37° C. Specific binding was detected using HRP-conjugated goat anti-mouse secondary antibody (diluted 1:2000, Cell Signalling Technology®, Danvers, Mass.) followed by the addition of o-phenylenediamine dihydrochloride (OPD) substrate (Sigma-Aldrich; St. Louis, Mo.). Hydrogen chloride (HCl) 1N was used to block the reaction. The optical density (OD) was read at 490-630 nm. Each sample was tested against non-immune serum and PBS as background controls. Amounts of IL-6 in the serum were analysed following the instructions provided by the by ELISA kit supplier (BD Biosciences, Mountain View, Calif.).

Western blotting. 20 µg of PbNK65 WT protein extract from asexual blood stages were separated by SDS-PAGE (4-12% Bis-Tris gels, BOLT mini gel system, Life Technologies) and transferred onto a PVDF membrane (iBLOT® system, Life Technologies, Carlsbad, Calif.). Mice sera from uninfected, WT or PbNK65-hrfiΔ1 were added (1:1000 dilution) and incubated overnight at 4° C. After washing the membrane with PBS+Tween-20 (Sigma-Aldrich; St. Louis, Mo.), polyclonal anti-mouse IgGs (1:20000, P0260, DAKO; Carpinteria, Calif.) were added and specific bands visualized with the SuperSignal® West Pico Kit (Thermo Scientific, Rockford, Ill.), according to manufacturer's instructions.

Adoptive transfer of IgG specific antibodies and CD11b positive cells. C57BL/6J mice were infected with either WT or PbNK65-hrfiΔ1 parasites as described above. Specific IgGs and CD 11b+ cells were obtained from challenged protected mice at day 15 p.i. Immune sera were collected and IgG fraction was purified on an immunoabsorbent protein G-sepharose column (BioVision, Milpitas, Calif., USA). 100 µg of IgGs were transferred i.p. into naive mice 24 h before WT PbNK65 iRBC infection. Mice were then given 100 µg of antibody on day 3 and 6 p.i. Single-cell suspension of CD 11b+ cells was obtained from naive or PbNK65-hrfiJ 1-infected mice by FACs sorting of spleen and bone marrow cells stained with FITC-labelled anti-CD 1 lb. Each mouse received intravenous injections of $2.5×10^6$ $CD11b^+$ cells 1 h after WT PbNK65 iRBC infection.

Statistical analysis. All data were analyzed using GraphPad Prism 5.0 software. Unpaired data between two groups at a specific time point were analysed by Mann-Whitney test for nonparametric analysis when data did not fit a Gaussian distribution. A p-value of <0.05 was considered to be statistically significant. All experiments were replicated several times as indicated in the figure legends.

Generation and cloning of PbNK65-hrfΔ parasites. For construction of targeting vector for pbhrf disruption, DNA fragments corresponding to the 5' untranslated (UTR) and 3'UTR regions of the pbhrf gene were amplified by PCR using *P. berghei* NK65 genomic DNA (gDNA) as template. These primers (see table 2) were tailed with restriction sites for ApaI, PstI, KpnI and EcoRI respectively, to facilitate cloning into either side of the human dihydrofolate reductase (hDHFR) cassette (de Koning-Ward et al., 2000) in pUC18 backbone. The targeting construct was integrated into the pbhrf gene locus by double crossover recombination, resulting in the disruption of pbhrf and conferring WR992 1 0 or pyrimethamine resistance. Transfection into a GFP-PbNK65 parasite strain and selection of recombinant parasite clones were performed as previously described (Janse et al., 2006). Briefly, after overnight culture (37° C., 10% O2, 5% CO2, 90 rpm) of the blood of infected animals, mature schizonts were purified using a Nycodenz gradient and collected at room temperature. The electroporation mix was composed of $10^7$ to $10^8$ merozoites resuspended in 50 µl, 100 µl of Human T cell Nucleofector solution (Amaxa) and 5 µl of DNA (containing 5 µg of digested DNA in water). Parasites were electroporated using the U33 program of the Nucleofector electroporator (Amaxa) and immediately resuspended in PBS and injected intravenously into 3-week-old female Swiss mice. Recipient mice were treated with pyrimethamine (0.07 mg/ml) in drinking water or with WR99210 (6 mg/kg) by subcutaneous injections, starting 24 h post-electroporation. At day 6 after electroporation, the emerging parasite population was collected, gDNA extracted and genomic integration of the hDHFR cassette within the pbhrf locus of GFP-PbNK65 transfectants confirmed using specific PCR primers: (i) Apa-5'UTR PbHRF-F and EcoRI-3' UTR PbHRF-R, (ii) HRF5'-F and hDHFR5'-R, and (iii) HRF3'-R and hDHFR3'-F. The first pair of primers (Apa-5'UTR PbHRF-F and EcoRI-3' UTR PbHRF-R) amplified gDNA encompassed by the ApaI and EcoRI restriction sites and inclusive of the pbhrf5' and 3'UTRs. A PCR product of 2681 bp was indicative of hrfΔ, whilst a PCR product of 1760 bp denoted a WT genotype. The second pair of primers (HRF-5'-F and hDHFR 5'-R) amplified DNA outside the hDHFR insert (inclusive of the 5'UTR PbHRF) and within the 5' region of the hDHFR cassette, respectively. A PCR product of 700 bp indicated a hrfΔ clone, whilst absence of a band denoted a WT genotype. The third pair of primers (hDHFR 3'-F and HRF 3'-R) amplified gDNA within the 3' region of the hDHFR cassette and outside the hDHFR insert (inclusive of the 3'UTR pbhrf), respectively. A PCR product of 1100 bp indicated a hrfΔ clone, whilst absence of a band indicated a WT genotype.

TABLE 2

List of oligonucleotides used for PCR of wild-type and recombinant parasites.

| Primer | Sequence | SEQ ID No |
|---|---|---|
| ApaI-5'UTR-PbHRF-F (a) | 5'-cgcgggcccgcgcattattaccgttgtca-3' | 25 |
| PstI-5'UTR-PbHRF-R | 5'-cgcctgcagggcttatgcaagtatcgaacaa-3' | 26 |
| KpnI-3'UTR-PbHRF-F | 5'-cgcggtaccttgctacatgacgcataaacc-3' | 27 |
| EcoRI-3'UTR-PbHRF-R (a') | 5'-cgcgaattctgtgaaatcgacaatgttttgg-3' | 28 |
| HRF5'-F (b) | 5'-gcgatacaaacaaatttattcagc-3' | 29 |
| HRF3'-R (c') | 5'-cgcaagatatcagagcttttca-3' | 30 |
| hDHFR 3'-F(c) | 5'-tgttgtctcttcaatgattcataaatagttgg-3' | 31 |
| hDHFR 5'-R (b') | 5'-tgctttgaggggtgagcatttaaagc-3' | 32 |
| PbHRF-5' orf-F | 5'-ccatttggaaatgcggaat-3' | 33 |
| PbHRF-3'orf-R | 5'-tttttcttcaaataaaccatctg -3' | 34 |

Bold letters refer to the oligonucleotides position in FIGS. 5A, 5B.

Southern blotting. Genomic DNA was obtained as follows: parasite pellets obtained by saponin lysis of iRBCs were resuspended in PBS and treated with 150 µg/ml proteinase K and 2% SDS at 55° C. for 20 min. The DNA was isolated from the parasite pellet using the DNeasy Blood and Tissue® kit (QIAGEN, Hilden, Germany). The DNA was digested with EcoRV and probed with an hrf probe.

Mass spectrometry analysis, database search, protein identification and statistical analysis. After the immunoprecipitation, proteins were solubilized in denaturation buffer (2-amino-2-hydroxymethyl-1,3-propanediol (Tris) 10 mM pH8.0, 8M urea). Proteins were reduced and alkylated and digested with trypsin. Tryptic peptides were analyzed by nano LC-MS/MS using an EASY-nLC 1000 (Thermo Fisher Scientific) coupled to a Q Exactive Orbitrap mass spectrometer. About 1 µg of each sample (dissolved in 0.10% FA) were loaded 250 nl·min−1 on a home-made C18 50 cm capillary column picotip silica emitter tip (75 µm diameter filled with 1.9 µm Reprosil-Pur Basic C 18-HD resin, (Dr. Maisch GmbH, Ammerbuch-Entringen, Germany)) equilibrated in solvent A (0.1% FA). The peptides were eluted using a two slopes gradient of solvent B (0.1% FA in ACN) from 2% to 30% in 90 min and to 30% to 80% in 60 min at 250 nL/min flow rate (total length of the chromatographie run was 180 min). The Q Exactive (Thermo Fisher Scientific, Bremen) was operated in data-dependent acquisition mode with the XCalibur software 2.2 (Thermo Fisher Scientific, Bremen). Survey scan MS were acquired in the Orbitrap on the 300-1800 m/z range with the resolution set to a value of 70 000 at m/z=400 in profile mode (AGC target at 1E6). The 20 most intense ions per survey scan were selected for HCD fragmentation (NCE 28), and the resulting fragments were analyzed in the Orbitrap at 17500 of resolution (m/z 400). Isolation of parent ion was fixed at 2.5 m/z and underfill ratio at 0.1%. Dynamic exclusion was employed within 20s. Each sample was prepared in triplicate.

Data were searched using MaxQuant (1.4.1.2 version) (with the Andromeda search engine) against the *Plasmodium berghei* database (22006 entries). The following search parameters were applied: Carbamidomethylation of cysteines was set as a fixed modification. Oxidation of methionine and protein N-terminal acetylation were set as variable modifications. The mass tolerances in MS and MS/MS were set to 10 ppm for each, respectively. Two peptides were required for protein identification and quantitation. Peptides and proteins identified with an FDR lower than 0.010% were considered as valid identification. Statistical analysis of the data was performed using Perseus (http:/1141.61.102.17/perseus_doku/), R package, MSstat (http://msstats.org/) and internal tools. Two sample t-test was used to identify significantly regulated proteins between two groups. Results were visualized on volcano plots.

Immunoprecipitation. Immunoprecipitation of Pb proteins from parasites extracts was performed using the Pierce™ Direct IP Kit (Thermo Scientific, Rockford, Ill.). Before immunoprecipitation, 10 µg of purified IgG antibodies from the serum of protected, infected and naïve mice were directly immobilized onto an agarose support (AminoLink™ Plus Resin) using a short coupling protocol. Parasites extracts (500-700 µg) were incubated with the immobilized antibody to form the immune complex with gentle end-over-end mixing overnight at 4° C. To remove non-bound material, beads were washed 3 times with wash buffer, and a low pH elution buffer is used to dissociate the bound antigen from the antibody. Immunoprecipitated proteins were then used for mass spectrometry analysis.

Example 2: Deletion of the Hrf Gene in PbNK65 Parasites Causes Abortive Blood-Stage Development We generated hrf knock-out PbNK65 parasites (PbNK65 hrfΔ) by replacing the coding sequence of pbhrf (PBANKA_111050) with the human dihydrofolate reductase selectable marker (hDHFR) in a GFP-expressing PbNK65 strain (FIG. 5A). Two clones, PbNK65-hrfΔ1-2, were selected from independent transfection experiments and verified to harbour the mutant locus by PCR (FIGS. 5B-D) and Southern blot analysis (FIG. 5E). Using specific rabbit antibodies against recombinant PbHRF (Mathieu et al., 2015), the protein was found to be expressed at all *Plasmodium* stages tested and to localize to the cytoplasm (FIG. 1A-D), consistent with previous reports in human cells and PbANKA parasites (Bhisutthibhan et al., 1999; Mathieu et al., 2015). HRF was not detected in PbNK65-hrfΔ1 parasites (FIG. 1A-D), confirming both antibody specificity and successful gene knockout.

To assess the effect of pbhrf deletion on parasite blood-stage development, C57BL/6 mice were infected intraperitoneally with $10^5$, $10^4$ or $10^3$ WT or PbNK65-hrfΔ1 infected iRBCs and parasite growth was monitored by flow cytometry. In mice infected with WT parasites, parasitemia increased steadily, resulting in severe malaria and death at day ~20 p.i. When using $10^5$ or $10^4$ infectious doses, PbNK65-hrfΔ1 parasites multiplied like WT until day 10 p.i., reaching parasitemia of ~20%, and were cleared from mice at day 13 or 14 p.i., respectively. Mouse survival rate after injection of $10^4$ or $10^5$ PbNK65-hrfΔ1 parasites was ~90% and ~70%, respectively. Notably, injection of $10^3$ PbNK65-hrfΔ1 parasites did not lead to parasite clearance or mouse survival. Infection with PbNK65-hrfΔ2, a second clone, gave similar results (FIG. 5F, G). We conclude that infection with parasites lacking HRF can self-resolve, and that parasite clearance depends on the initial parasite load and/or time to threshold parasitemia. Further experiments were performed following injection of $10^5$ PbNK65-hrfΔ1 parasites.

To determine whether clearance of mutant parasites from the circulation could be due to parasite retention in the spleen, the parasite load in this organ was measured by real-time PCR (RT-qPCR). After a dramatic retention of PbNK65-hrfΔ1 parasites at day 6, parasites were no longer detected in the spleen at day 14 (FIG. 1F), indicating that parasite clearance was not due to retention in the spleen (FIG. 1G). Moreover, macroscopic examination showed a more important splenomegaly at day 6 in PbNK65-hrfΔ1-infected mice than in WT-infected mice, suggesting leukocyte infiltration in the mutant-infected spleen (FIG. 1H-J).

Example 3: IL-6, B Cells and T Cells are Critical for Inhibition of PbNK65-HrfΔ Blood-Stage Growth Since HRF-deficient PbANKA sporozoites induce IL-6 production in the liver during pre-erythrocytic infection (Mathieu et al., 2015), we compared IL-6 levels in mouse spleens 6 days p.i with WT or PbNK65-hrfΔ1 iRBCs. Levels of IL-6 mRNA and plasmatic IL-6 protein were higher in PbNK65-hrfΔ1-infected mice than in WT-infected mice (FIG. 2A, B). Given that recombinant PbHRF protein is sufficient to down-regulate IL-6 expression in vivo (Mathieu et al., 2015), we tested whether clearance of mutant parasites was the consequence of elevated IL-6 by infecting IL-6$^{Ko}$ mice with mutant parasites. Mutant parasites developed normally in, and eventually killed IL-6$^{Ko}$ mice (FIG. 2C), phenocopying WT parasite behavior in WT mice (FIG. 1E). We conclude that increased IL-6 accounts for mutant parasite clearance.

Immunostaining with leukocyte surface markers and anti-IL-6 antibodies of cells collected from the spleen at days 6 and 20 p.i. identified IL-6 producing cells as Ly6G+ neutrophils at day 6 and both Ly6G$^+$ neutrophils and CD 11c$^+$ dendritic cells (DCs) at day 20 (FIG. 2D). Depletion of neutrophils (FIG. 6A, B) or DCs (FIG. 6C, D) in mutant-infected mice reduced splenomegaly (FIG. 6E,F,H,I) and cell counts (FIG. 6G,J) compared to non-depleted mice, confirming the contribution of neutrophils and DCs in the splenomegaly caused by mutant infection.

IL-6 is known to regulate the acute phase of the immune response and major B and T cell functions (Barton, 1997; Kishimoto et al., 1992). To test whether B or T cells were involved in self-resolution of mutant infection, we infected mice lacking B cells (μs$^{KO}$ or T cells CD3$^{KO}$ with WT or PbNK65-hrfΔ1 parasites and monitored parasite development. B cell- or T cell-deficient mice were unable to control PbNK65-hrfΔ1 blood-stage multiplication and died with similar kinetics than WT mice infected by WT parasites (FIG. 2E,F). The importance of T cells was confirmed by the normal multiplication of the mutant parasite upon mouse treatment of previously protected mice with anti-CD3 antibody (FIG. 2G, 6K). This indicated that B and T lymphocytes contributed to the clearance of mutant parasite.

Example 4: PbNK65-HrfΔ1 Infection Confers Lasting Protection in a Species- and Stage-Transcendent Manner To determine whether resolved PbNK65-hrfΔ1 parasite infection might confer protection against challenge, mutant-infected mice were challenged with $10^5$ WT PbNK65 iRBCs at days 20, 35, 68, 168 and 396 p.i. Mice were protected in all cases, displaying no detectable parasitemia at any timepoint, and survived for more than a year (FIG. 3A). Mice challenged at days 20 and 23 p.i. with $10^5$ RBCs infected with virulent *P. berghei* ANKA (FIG. 3B) or *P. yoelii* YM (FIG. 3C), respectively, were also protected and did not develop parasitemia. Next, the inventors asked if mutant-infected mice were also protected against a challenge with WT PbNK65 sporozoites, the mosquito-transmitted parasite stage. Sporozoite challenge did not result in detectable blood-stage infection (FIG. 3D) and parasite genes were not detected in blood by PCR (not shown). To ascertain that protection indeed targeted pre-erythrocytic stages, and not just emerging blood-stage development, the livers of mice challenged with sporozoites were analyzed by RT-qPCR 40 h post-sporozoite inoculation. As shown in FIG. 3E, the parasite load was significantly lower in the liver of PbNK65-hrfΔ1-protected mice compared to control mice. A similar protection was observed against heterologous *P. berghei* ANKA (FIG. 3F) and *P. yoelii* YM (FIG. 3G) sporozoite challenge. Therefore, infection with HRF-deficient blood-stage PbNK65 parasites induces long-lasting protection against malaria in a species- and stage-transcendent manner.

Example 5: Mutant-Induced Immunity Involves *Plasmodium*-Specific IgG2c Antibodies To assess whether antibodies were involved in the anti-PbNK65-hrfΔ1 response, anti-parasite specific antibodies of various isotypes were quantified by ELISA in sera of mice 15 days p.i. with WT or PbNK65-hrfΔ1 parasites. As shown in FIG. 4A, mice infected with PbNK65-hrfΔ1 produced higher levels of IgG antibodies than mice infected with WT parasites, essentially belonging to the IgG2c subclass and to a lesser extent to the IgG3 subclass (FIG. 4A). Next, as shown by western blot analysis of extracts from WT blood stages (FIG. 4B), these antibodies recognized multiple *P. berghei* antigens in contrast to sera from WT PbNK65-infected mice or from naïve mice (FIG. 4B). Interestingly, the IgG2c isotype, expressed in C57BL/6 mice in which the IgG2a heavy chain is deleted, is known to be the predominant isotype generated in antiviral antibody responses (Coutelier et al., 1987) and the most efficient IgG subclass for anti-pathogen FcR-mediated effector functions (Nimmerjahn and Ravetch, 2005). In most experimental mouse malaria models, parasite-specific antibodies have been shown to be predominantlyskewed toward the IgG2c isotype (Ndungu et al., 2009).

Immunoprecipitation of *P. berghei* blood stage proteins with the IgG antibodies from mutant-infected mice and mass spectrometry of the immunoprecipitate revealed five *P. berghei* proteins targeted by the protective IgG response (FIG. 7A,B). These included the vaccine candidates merozoite surface protein 1 (MSP1), serine repeat antigen 1 (SERA1), and SERA2 (Alaro et al., 2013; Bodescot et al., 2004; Putrianti et al., 2010). A shown by immunoblot (FIG. 7C) and ELISA (FIG. 7D), only sera from protected mice recognized the recombinant MSP1-33 antigen.

Next, to test if IgG antibodies may mediate parasite clearance via FcRγ-expressing cells, WT or FcRγ$^{KO}$ C57BL/6 mice were infected with PbNK65-hrfΔ1 parasites. As shown in FIG. 4C, in contrast to WT mice, FcRγ$^{KO}$ mice were unable to eliminate PbNK65-hrfΔ1 parasites and phenocopied WT mice infected with WT parasites.

Example 6: Antibodies and CD11b Cells from Mutant-Infected Mice Mediate Protective Immunity Finally, to assess what immune effectors are important for protection, we performed passive transfer experiments. First, antibodies purified from protected mice were transferred to naïve mice before challenge with WT PbNK65 parasites. As shown in FIG. 4D, parasitemia was lower in mice treated with IgG from protected mice than in normal IgG-treated mice, suggesting that antibodies alone provide partial, but significant, protective activity FIG. 4D.

Last, we asked if CD11b' cells such as phagocytic leukocytes from PbNK65-hrfΔ1-protected mice might be sufficient to protect naive mice from WT infection. WT C57BL/6 mice with adoptively transferred CD11b$^+$ cells from naive or PbNK65-hrfΔ1-infected mice at day 15 p.i. were challenged with $10^5$ WT parasites. As shown in FIG. 4E, transfer of CD11b$^+$ cells from mutant-infected, but not naive mice, efficiently protected against infection. Taken together, these data suggest that parasite antigen-specific antibodies and FcγR$^+$CD11b$^+$ cells play an important part in mutant-induced protection.

Discussion

These data reported in the examples show that abortive blood-stage infection leading to lasting protection can be achieved not just by impairing parasite intracellular growth but also by enhancing protective immune responses. Indeed lack of HRF, and the increase in IL-6, do not affect parasite growth per se since PbNK65-hrfΔ blood stages multiply normally in mice until day 10. Rather, IL-6, which is involved in B and T cell differentiation, boosts anti-parasite adaptive responses that clear parasites. Like with previously reported blood-stage GAPs that induce abortive infections, the protective response to PbNK65-hrfΔ parasites is both solid, conferring cross-stage and cross-species immunity, and durable. the inventors found that the protective response relies on the combination of anti-parasite IgG2c antibodies and FcγR+CD11b+ cells phagocytic cells, in particular neutrophils, which are sufficient for solid protection. Interestingly, the discovery of a B-helper neutrophil population in the spleen that can act as professional helper cells for marginal zone B-cells (Puga et al., 2012) highlights a neutrophil-B cell interplay that may be critical for B cell differentiation into antibody-producing plasma cells and may also contribute to inhibit the well-known *Plasmodium* capacity to induce short-lived B-cell memory (Wykes et al., 2005). Opsonic phagocytosis was also described as a protective mechanism induced by the plasmepsin-4-deficient mutant (Spaccapelo et al., 2010). Whether this represents the essential protective mechanism common to all self-resolving infections remains to be determined. Finally, although not formally demonstrated in these data, the contribution of parasite-specific CD8$^+$ cells to self-resolution cannot be precluded and awaits further investigation.

II. Impaired Immunological Memory Against Blood Stage Malaria in Mice is Restored by the Histamine Releasing Factor (HRF) Deficient Murine Parasite Example 7. Methods and Materials Ethics statements. All animal care and experiments described in the present study involving mice were conducted at the Institut Pasteur, approved by the 'Direction Départementale des Services Vétérinaires' de Paris, France (Permit Number No 75-066 issued on Sep. 14, 2009) and performed in compliance with institutional guidelines and European regulations (http://ec.europa.eu/environment/chemical?s/lab_animals/home_en.htm). A statement of compliance with the French Government's ethical and animal experiment regulations was issued by the Ministère de l'Enseignement Supérieur et de la Recherche under the number 00218.01.

Rodents. Five- to eight-week-old wild-type female C57BL/6J Rj and Swiss Webster (SW) mice were purchased from Janvier laboratory (Le Genest-Saint-Isle, France). Transgenic AID/YFP 45 were kindly provided by Dr. Antonio A. Freitas (Institut Pasteur, Paris, France).

Parasites. Mice were inoculated with red blood cells infected (iRBCs) or sporozoites collected from salivary glands of infected *Anopheles stephensi* with either GFP-transgenic *Plasmodium berghei* (Pb) NK65 wild-type or mutant (hrfΔ) GFP-transgenic clones.

Mouse infections. Mice were infected with blood stages of either GFP-transgenic *P. berghei* NK65 or PbNK65 hrfΔ parasites by injecting $10^5$ infected red blood cells (iRBCs) intraperitoneally (i.p) or $10^3$ sporozoites intravenous (i.v.). After the infection, blood samples were taken daily from the tail and the parasitemia was assessed by flow cytometry and the results expressed in percentage of iRBC. Infected mice were monitored for clinical symptoms of the disease: weight loss, anemia, fever and death.

Drug treatment. Once mice infected with PbNK65 WT iRBCs reach 2% of parasitemia were treated with for three consecutive days with 6 mg/kg of WR99210 (Sigma-Aldrich, Saint Louis, USA) by subcutaneous (s.c.) injections. Once the parasites were completely eliminated from blood stream mice were infected either with $10^5$ PbNK65 WT or hrfΔ iRBCs. The group of mice who received the PbNK65 hrfΔ and eliminated it from the blood stream were additionally challenged with $10^5$ PbNK65 WT iRBCs.

Preparation of total RNA and reverse transcription-quantitative PCR (RT-qPCR) analysis of mRNA. The livers and spleens of C57BL/6J mice infected with WT or PbNK65 hrfΔ1 parasites were surgically removed 48 h, 72 h, 96 h and 120 h p.i. or at day 2, 4, 6, 8, 10, 12, 14 and 20 p.i., respectively. Total RNAs were extracted from the spleen as well from the liver samples using the guanidinium-thiocyanate-phenol-chloroform method (all Invitrogen, Waltham, Mass., USA). RNA was thereafter reverse transcribed by PCR (temperature profile: 65° C. for 5 min, 42° C. for 50 min, 70° C. for 15 min) using 100 U SuperScript™ II reverse transcriptase (RT) (Invitrogen, Waltham, Mass., USA), 40 U RNAse Inhibitor and 2 □M oligo(dT) 18S rRNA primer (Eurofins MWG Operon, Ebersberg, Germany) per sample. The expression levels of diverse transcripts were analyzed by real time RT-qPCR using Power SYBR® Green PCR Master Mix (Applied Biosystems Foster City, Calif., USA) and various primers sets (table S1). All reactions were performed in the ABI PRISM 7000 Sequence Dectection System Real Time PCR machine (temperature profile: 50° C. for 2 min, 95° C. for 10 min, 40 cycles of 95° C. for 15 s and 60° C. for 1 min). The relative abundance of parasite and cytokines rRNA in the spleen was calculated using the $\Delta C_t$ method, and expressed as $2^{-\Delta c_t}$. The mouse hypoxanthine phosphoribosyltransferase (HPRT) gene was used as an internal control for the variation in input RNA amounts. No template control (NTC) was included to ensure that there was no cross-contamination during sample preparation.

Detection of specific antibodies, cytokines, and chemokines in the serum of infected mice. To detect parasite-specific antibodies, 96-well plates (Nunc-immuno plate; Thermo Scientific, Rockford, Ill.) were coated with parasite protein extract from asexual blood stages in carbonate buffer, pH 9.6, for 2 h at 37° C. After the plates were saturated with 10% (w/v) pork gelatine, each serum was assayed at serial dilutions and incubated overnight for 2 h at 37° C. Specific binding was detected using HRP-conjugated goat anti-mouse secondary antibody (Cell Signalling Technology®, Danvers, Mass.) followed by the addition of o-phenylene-diamine dihydrochloride (OPD) substrate (Sigma-Aldrich; St. Louis, Mo.). Hydrogen chloride (HCl) 1N was used to block the reaction. The optical density (OD) was read at 490-655 nm. Each sample was tested against non-immune serum and PBS as background controls. Amounts of IL-12p70, IFN-γ and IL-6 in the serum were analysed by cytokine-specific ELISA kits (BD Biosciences, Mountain View, Calif.).

Flow cytometry analysis of spleen leukocytes. Spleens were mechanically disrupted in 2 ml PBS and cells were filtered through a 70-mm strainer (BD Falcon). Erythrocytes on the cell suspension were lysed using Gey's solution for 5 min of incubation on ice and after washed two times in PBS. Single-cell suspension were stained for FACS analysis according to standard protocols in cold PBS containing 2% FCS and 0.01% sodium azide (FACS buffer) with the following monoclonal antibodies conjugated to fluorescein isothiocyanate (FITC), phycoerythrin (PE), phycoerythrin-cyanine 5 (PeCy5), phycoerythrin-cyanine 7 (PeCy7), peridinin chlorophyll protein-cyanine 5.5 (PerCp-cy5.5), allophycocyanine (APC) and Qdot-605: anti-CD4 (FITC), anti-CD8a (PE), anti-GL7 (PE), anti-CD62L (PeCy5), anti-CD95 (PeCy7), anti-IgM (PerCp-cy5.5), anti-PD1 (APC), anti-IgG (APC) and CD19 (Qdot-605)(all antibodies from BD Bioscience, Mountain View, Calif.). Before staining, a total of 5×10^5 living cells, were treated with Fc-Block (clone 2.4G2, BD Bioscience, Mountain View, Calif.). Dead cells were excluded during analysis according to their light-scattering characteristics. All data and analyses were performed with LSRFortessa (Becton Dickinson, Grenoble, France) using FlowJo software (Tree Star, Ashland, Oreg., USA).

In vivo cell depletion. To determine if the protection induced by PbNK65 hrfΔ is dependent on effector CD4+ or CD8+ T cells, cell-specific depletion experiments were performed. C57BL/6J Rj protected mice were injected i.p. with 20 μg of anti-CD8 clone 53-6.7 Armenian hamster IgG (eBioscience, San Diego, Calif.) or 100 μg of rat anti mouse CD4 clone GK1.5 (ATCC® TIB207™) 48 h before the infection with PbNK65 WT followed by 6 injections administered every other day after the infection. The cell depletion was followed and confirmed every day by taking 10 μl of blood from the tip of the mouse tail and analysed by flow cytometry.

Statistical analysis. All data were analyzed using Graph-Pad Prism 5.0 software. Unparied data between two groups at a specific time point were analysed by Mann-Whitney test for nonparametric analysis when data did not fit a Gaussian distribution. A p-value of <0.05 was considered to be statistically significant. All experiments were replicated several times as indicated in the figure legends.

Example 8: HRF Plays a Critical Role in Parasite Development Both at the Pre-Erythrocytic and Erythrocytic Stages As demonstrated above, inoculation of mice with PbNK65-hrfΔ iRBCs resulted, after an initial phase of parasite development, in self-resolved infection with a long lasting protection and mouse survival (FIG. 11A) against secondary infections with WT parasites. We then tested whether HRF might play a role during sporozoite progression in vivo. Infection with PbNK65-hrfΔ sporozoites resulted in an initial delayed development of the parasite followed by a complete clearance during blood stage at around day 17 p.i. (FIG. 11B), in a similar way as the parasite was inoculated with iRBCs (FIG. 11A). To assess whether clearance of the parasites in this setting resulted in protection against a parasite challenge, mice were reinfected at day 36 with PbNK65 WT iRBCs. As shown in FIG. 17, there was no blood stage parasite development, indicating that self-resolved parasites inoculated as PbNK65-hrfΔ sporozoites elicited similar protection as that generated by blood stage PbNK65-hrfΔ parasites. Inoculation of naïve mice with PbNK65 WT iRBCs at day 36 used as controls resulted in development of parasitemia and death of mice around day 15 p.i. (day 50 p.i. in the figure). To analyse liver-stage development in vivo, mice were injected with sporozoites IV and liver samples collected at 48, 72, 96 or 120 h p.i. were subjected to qRT-PCR analysis of parasite LSP2 RNA (FIG. 11C). At 48 h p.i., the PbNK65-hrfΔ parasite load was ~ 2 times lower than that of the WT. At 72 h p.i., WT parasites were undetectable while the amounts of PbNK65-hrfΔ parasites had risen and reached at 96 hpi to levels similar to those of the WT at 48 h p.i. At 120 h p.i., both WT andPbNK65-hrfΔ parasites were undetectable in the liver. Therefore, RT-PCR analysis in the liver indicated a >48 h delay in the completion of the pre-erythrocytic phase. This phenotype is similar to another HRF mutant made previously in a distinct Plasmodium berghei strain, PbANKA (PbANKA-hrfΔ)[24]. One of the immunological features observed previously with PbANKA-hrfΔ model, in contrast to the WT parasite, was an early rise of IL-6 in the liver[24]. Since HRF is important for liver-stage development, here we assessed the levels of IL-6 expression and found that at 48 hpi, the transcripts for IL-6 were the sole among those tested that were differentially expressed between infections with WT and PbNK65-hrfΔ parasites, being increased six-fold in PbNK65-hrfΔ-infected liver samples (FIG. 11D). We conclude that the increase in IL-6 production accounts for mutant parasite clearance for both PbANKA and PbNK65. Since similar phenotypes were obtained with both sporozoites and iRBCs, the follow-up investigation was carried out using iRBCs to explore the mechanisms by which HRF modulates the T cell and B cell immune responses.

Example 9: Prior Exposure to WT Parasite Followed by Drug Treatment does not Hamper PbNK65-HrfΔ-Induced Parasite Clearance and Immune Protection Results reported above, obtained from mice infected firstly with PbNK65-hrfΔ parasites and, upon the complete clearance of PbNK65-hrfΔ parasites, challenged with either PbNK65, PbANKA or PyYM WT lethal parasites demonstrated that the sterile protection conferred by this GAP is long-lasting in a species- and stage-transcendent manner. In endemic areas pre-exposure to WT parasites followed by antimalarial chemotherapy could induce epigenetic marks that may negatively influence anti-parasite immunity. In this situation the protective effect induced by the PbNK65-hrfΔ mutant will not be effective. The question is to assess whether these individuals who had been exposed to WT parasites and drug cured will be equally efficiently protected following PbNK65-hrfΔ infection as in naïve mice. To address this issue, mice were first infected with $10^5$ PbNK65 WT iRBCs, and when parasitemia reached around 2%, were treated for three consecutive days with 6 mg/kg WR99210 by subcutaneous injections. Once the parasites were completely eliminated from the blood stream, at day 19 p.i., mice were infected either with $10^5$ WT or with PbNK65-hrfΔ iRBCs (FIG. 12). We observed that in the group of mice which have received WT parasites, parasites develop normally and the mice died around day 16 p.i. In contrast, mice which received PbNK65-hrfΔ parasites, show a slow development of parasites which were ultimately eliminated around day 15 p.i. from peripheral blood circulation as highlighted by the zoomed inset in the figure (FIG. 12). To assess whether one single infection with the mutant parasite was enough to develop a long-lasting immune response, as we previously reported without the use of drugs, mice which received WT parasites followed by drug treatment and PbNK65-hrfΔ parasites were infected again with $10^5$ WT iRBCs 4 weeks after the elimination of the mutant parasite from the blood circulation (FIG. 12). A control group, which has been neither infected nor treated by antimalarial drugs, was infected at the same time with $10^5$ WT iRBCs. As obtained with WT parasite challenges in protected mice without drug treatment, infection with PbNK65-hrfΔ parasites allows the development of a long-lasting immune protection despite a prior drug treatment. This result shows that a primary infection with WT parasites followed by a drug cure does not hamper the efficacy of PbNK65-hrfΔ-induced protection.

Example 10: Pattern of Cytokines Associated with PbNK65-HrfΔ Induced Protection It is known from previous studies that both CD4+ and CD8+ T cells play a central role in the elimination of blood-stage malaria parasites through the release of cytokines that activate other effector cells such as NK cells, macrophages and dendritic cells. In addition, Th1 cytokines IL-12, IFN-γ, and TNF-α, were shown to confer immunity against blood-stage *Plasmodium* infection[25]. To examine whether the infection of C57BL/6 mice with either the WT or PbNK65 hrfΔ parasite induces a particular set of cytokines, we first examined the mRNA expression of a variety of cytokines by RT-PCR in the spleen of infected mice at various time intervals after infection, starting from day 2 until day 14, p.i. (FIG. 13). A higher expression of IFN-γ, IL-10, IL-6 and TL-12p35 cytokines was noticed at day-6 p.i. in mice infected with PbNK65 hrfΔ as compared to WT parasites (FIG. 13). A more detailed analysis of this group of cytokines was performed at day 6 p.i. in the liver and in the spleen of infected mice. Analyzed samples showed that IL-23, EBI-3 (IL-27 beta subunit), IL-12p40, IL-12p35, IFN-γ, IL-6, and IL-10 mRNA expression were all higher both in the liver and in the spleen during PbNK65 hrfΔ parasites infection as compared to WT parasites infection (FIG. 18A,B). At the protein level, higher production of IFN-γ, IL-12p70, and IL-6, as measured by ELISA, was confirmed in the plasma of PbNK65 hrfΔ infected mice as compared to WT parasite-infected mice (FIG. 18C). This burst of pro-inflammatory cytokines induced by PbNK65 hrfΔ parasites was followed by a significant loss of weight at day 8 p.i. (FIG. 19B), which resulted first in the decrease of the parasitemia followed by the normalization of the weight a few days later (day 10 p.i.). The loss of weight from day 4 to day 8 represented 10% of the weight of control mice at the same age. In contrast, mice infected with WT parasites did not show any loss of weight until day 8 where this was continuously decreasing until the death of the mice (FIG. 13B). Mice that were infected with WT parasites displayed a delayed peak of TNF-α, IL-10 and IL-6 at day 12-14 post infection which in addition to high parasitemia may be associated to a drastic loss of body weight in these mice starting from day 14 (FIG. 13B).

Example 11: Protection Conferred by Mutant Parasites is Dependent on Effector CD4+ T Cells The inventors have shown in the results reported above the critical role of T cells in the development of an amnestic response in mice previously infected with PbNK65 hrfΔ1 parasites. Indeed, when CD3+ T cells were depleted, this group of mice were not able to control further infections with WT parasites. In order to show that the protection induced by PbNK65 hrfΔ parasites is dependent on effector CD8+ or CD4+ T cells, protected mice were treated with normal mouse IgG, or with anti-CD8 or with anti-CD4 depleting antibodies. Efficacy of CD4 and CD8 depletion was continuously monitored during administration of T-cell depleting antibodies and after this treatment was discontinued (FIG. 19). Mice were then challenged with $10^5$ iRBCs of WT PbNK65 parasites (FIG. 14) and both parasite growth and cell depletion efficacy were monitored daily by flow cytometry in blood samples. Interestingly, the measurement of parasitemia indicated a loss of parasite control upon treatment of protected mice with anti-CD4 antibody (FIG. 14A) but not with anti-CD8 antibody (FIG. 14B). WT parasite-challenged mice treated with control IgG remained parasite free. This suggests that the activation of CD4+ T effector lymphocytes but not CD8+ is indispensable for clearance of malaria infection in long term immune protection. These results are further supported by previous studies in animal models where depletion or adoptive transfer of different T cell populations highlighted the important role of CD4+ T cells in the development of protective immunity against blood stages[26, 27].

Example 12: Protection Induced by PbNK65-HrfΔ Parasites is Associated with Down-Regulation of PD-1 on T Cells As previously observed, mice lacking T cells were unable to control the parasitemia of PbNK65 hrfΔ parasites suggesting that the activation of T lymphocytes may be indispensable for immune memory against malaria infection. In order to better characterize the molecular signatures of the T cell response and given that chronic malaria infection results in an increased frequency of T cells expressing surface markers of exhaustion such as programmed cell death-1 (PD-1)[13], we asked whether the self-resolving nature of PbNK65 hrfΔ infection could be correlated to a change in PD-1 expression on the surface of effector T cells. Analysis of PD-1 expression by flow cytometry at day 6 and day 20 p.i. (FIG. 15A) indicated that WT parasites induced a high proportion of PD1$^+$CD4$^+$ and PD1$^+$CD8$^+$ T cells in the spleen hinting at T cell exhaustion. In contrast, PbNK65 hrfΔ parasites induced two-fold fewer PD1$^+$ CD4$^+$ and PD1$^+$ CD8$^+$ T cells at day 6 p.i. as compared to WT parasites, with this number decreasing to basal levels found in uninfected mice at day 20 p.i. (FIG. 15A). We further correlated PD-1 expression to the activation status of T cells using the cell surface marker CD62L: low or undetectable levels of surface CD62L are indicative of T cell activation and effector function[28]. At day 6 p.i. we observed in WT parasite-infected mice, 65% and 70% of activated CD4$^+$CD62L$^-$ and CD8$^+$CD62L$^-$ T cells, respectively, were PD-li whereas only 40% of activated CD4$^+$CD62L$^-$ and CD8$^+$CD62L$^-$ T cells were positive for PD-1$^+$ in mice infected with PbNK65 hrfΔ parasites (FIG. 15B). The number of PD-1$^+$ activated T cells further decreased at day 20 p.i. in PbNK65 hrfΔ-infected mice, resetting to the basal levels found in uninfected mice (FIG. 15B). To investigate whether rPbHRF can directly modulate the expression of PD-1 on the surface of T cells, naïve mice were injected with 100 μg of rPbHRF or BSA as a negative control and 48 h later, PD-1 surface expression examined. We observed an upregulation of PD-1 on CD4$^+$ and CD8$^+$ T cells surface (FIG. 15C) and on activated CD4$^+$ CD62L$^-$ and CD8$^+$ CD62L$^-$ T cells (FIG. 15D) induced by the rPbHRF. Taken together, these data demonstrate that infection with PbNK65 parasites expressing PbHRF is associated with an increased proportion of PD-1$^+$ T cells in mice, indicative of T cell exhaustion.

Example 13: Infection with PbNK65 HrfΔ Parasites is Associated with a Marked Increase in the Number of Effector Memory B Cells In above reported data, in contrast to mice infected with the WT parasite, we found that mice infected with the mutant parasite developed a strong and long lasting antibody response associated with the opsonisation and the priming of CD11b cells that were essential for infection resolution. Here we went further in a detailed analysis of the generation of memory B cells upon infection with the mutant parasite. The germinal centers (GCs) are the main site where somatic hypermutations and class switch recombination occur. During the immune response, B cells express the activation-induced cytidine deaminase (AID) enzyme, which induces the two major alterations in Ig gene loci to enhance antibody and B cell function. These B cells that have activated AID transcription, which we can visualize using AID/YFP transgenic mice, are defined as memory B cells containing populations of "central" memory (AID/YFP+CD19+IgM+ IgG-) and "effector" memory (AID/YFP+CD19+IgM- IgG+) B cells. Analysis of central and memory B cell populations is based on a combination of cell surface markers using a first gating on CD19+ AID-YFP+ cells followed by another gate on GL7+ CD95+ cell population and finally gating on IgG+ or IgM+ cell populations (FIG. 20). In order to investigate the generation of the immunological memory during *Plasmodium* infections, AID/YFP mice were infected i.p with 105 of either WT or PbNK65 hrfΔ iRBCs. At day 15 post-infection mice were killed and spleen B cell populations analysed by flow cytometry. As shown in FIG. 16, significantly higher total memory and GC memory B cells, central and effector memory B cells were observed in mice infected with the mutant parasite as compared to the WT parasite (FIGS. 16 A, B, C, and D, respectively). These results reinforce the hypothesis that B cells are important effectors in the immune response developed in C57BL/6 mice against PbNK65 hrfΔ parasites which act in tandem with CD4+ T cells.

Discussion

In recent years, in addition to subunit vaccines and RASs, researchers have used rodent models to test the efficacy of GAPs as vaccines against pre-erythrocytic and blood stage infections of malaria parasites. Indeed, some of the pre-erythrocytic GAP studies have been extended to human malaria parasites: for example, *P. falciparum* Δp32Δp36Δsap1 GAPs that arrest in pre-erythrocytic stages, when tested in human adult volunteers, they conferred safety and immunogenicity[29]. Similar mutations in rodent malaria parasites engendered complete, protracted immunity against infectious sporozoite challenge in mice[29]. However, few candidates for blood stage GAP vaccines have been explored. To address this, we genetically depleted the immunomodulatory secreted molecule HRF from the severe malaria-causing mouse parasite strain *P. berghei* NK65 and found that this resulted in a developmental arrest at the pre erythrocytic stage, with infections self-resolving at day 12 p.i. This self-resolution was characterized by an immune signature that comprised elevated IL-6 levels, activation of T cells and B cells, and antigen-specific IgG2c production. Importantly, the PbNK65 hrfΔ genetically modified parasites induced strong, long-lasting cross-stage and cross-species protection against subsequent malaria infections suggesting that the immune effector mechanisms were directed against antigens shared by different stages and parasite species. Therefore, we present this novel GAP as a putative blood stage malaria vaccine.

The reasons for the abortive infection and subsequent protection by PbNK65 hrfΔ parasites are likely multifactorial. But, induction of IL-6 upon infection with the PbNK65 hrfΔ parasite appears to be a key mechanism which is commonly encountered at both pre-erythrocytic and erythrocytic stages and regardless of the parasite genetic background, i.e. PbNK65 hrfΔ or PbANKA hrfΔ[24]. Indeed, similar to infection with PbANKA hrfΔ sporozoites 24, a delayed development of PbNK65 hrfΔ sporozoites in the liver was associated with a sharp peak of IL-6 up-regulation in this tissue at 48 h p.i (FIG. 11D), indicating that up-regulation of IL-6 following infection with mutant parasites regardless of the strain of the parasite used is a hallmark of the HRF gene product which was shown to directly control IL-6 production. This later property is key in the understanding of the protective mechanisms elicited by PbNK65 hrfΔ parasites. Indeed, concomitantly with and dependent on IL-6 production, we detected a higher production of IL-12 cytokine family including IL-12p35, IL-12p40, IL-23, and Ebi3. During malaria infection, early non-specific immune responses can be augmented by the release of IL-12 from splenic macrophages[30, 31] and the activation of these macrophages by the production of IFN-γ results in increased phagocytic activity and killing of malaria parasites. A parallel can be made in the human situation since during *P. falciparum* infection, children with mild malaria infection have higher levels of plasma IL-12 when compared to children with severe malaria infection, and the levels of IL-12 are inversely correlated with parasitemia and numbers of malaria pigment-containing neutrophils[32, 33]. This interplay between IL-6 and Th1-mediated protective immune response has been recently documented by the prominent role of IL-6 in the induction of Th1 cell response in vivo which enables T cell activation by making CD4 T-cells less sensitive to the suppressive activity of Tregs, in promoting the generation of functional memory CD4$^+$ T cells, and in providing help to B cells[34]. Two key findings were presented in the present work: first, a significant proportion of CD4 and CD8 T cells have their surface programmed death-1 (PD-1) expression upregulated during infection with WT parasites in contrast to hrfΔ parasites. PbNK65 hrfΔ infections correlated with a reduction of CD4$^+$PD1$^+$CD62L$^-$ and CD8$^+$PD1$^+$CD62L$^-$ cells, which are memory effector T cells. The PD-1 marker was found early during infection, as early as day 6, and lasted throughout infection, suggesting a possible influence of lack of PD-1 on both clearance of primary infection and induction of lasting protection. Signalling through the PD-1 receptor is thought to "exhaust" CD4$^+$ and CD8$^+$ T cells, leading to poor effector functions and expression of inhibitory receptors[35, 36, 37]. Interestingly, an involvement of PD-1 in the control of malaria blood stage has already been reported: in *P. falciparum* infections, higher expression of PD-1 was associated with T cell dysfunction, and therapeutic blockade of PD-1 ligand in a murine model of infection rapidly cleared blood-stage malaria in a B- and T-cell dependent manner[13]. In the *P. chabaudii* rodent model of chronic blood stage infection[38], parasite-specific CD8$^+$ T cells undergo significant PD-1-dependent exhaustion (up to 95% reduction), which exacerbates acute blood stage infection and drives chronic disease. Interestingly, HRF was found to directly up-regulate the expression of PD-1 on CD4$^+$ and CD8$^+$ T-cells (FIG. 15C, D). Because HRF down-regulates IL-6 production[23], a relationship may exist between IL-6 and PD-1 expression. A parallel can be made with a recent finding where IL-6 modulates CD4$^+$ T cell reactivity to PD-L1 by inducing the release of a soluble form of PD-1[39]. The apparent down-regulation of PD-1 expression on T cells in mice infected with PbNK65 hrfΔ parasites could therefore be interpreted as a shedding of PD-1 from the T cell surface. The second important finding in this work is that anti-parasite antibodies could not be detected at any time of the infection course with the WT parasite during which the B cell compartment seems to be completely non-functional. Recently, it was demonstrated that severe blood infection with PbANKA strain inhibited T helper cell differentiation and germinal center formation[40]. In accordance with our work, the aberrant B cell memory and the lack of maintenance of specific antibody response upon infection with WT PbNK65 parasite was completely restored in mice infected with the PbNK65 hrfΔ parasite. It is generally recognized that a response to a T cell-dependent antigen results in B cell memory taking place in germinal centers. At this particular site, affinity maturation and class switching of antibody receptors are initiated by the germinal center-specific enzyme activation-induced cytidine deaminase (AID)[41]. Using AID/YFP reporter mice, we could determine the fate of germinal center memory B cells (AID/YFP$^+$CD19$^+$ GL7$^+$CD95$^+$) in mice infected with WT PbNK65 as compared with PbNK65 hrfΔ parasites. Consistent with reported in examples 1 to 7 data, a significantly higher proportion and number of memory B cells were observed in mice infected with mutant parasites. A thorough analysis of memory B cell sub-populations revealed a higher proportion and number of both central (IgM$^+$IgG$^-$) and effector memory (IgM$^-$ IgG$^+$) B cells in mice protected following infection with PbNK65 hrfΔ parasites. The role of CD4$^+$ and CD8$^+$ T-cell and antibody responses, particularly against blood stage, remains elusive mostly due to the diversity of experimental protocols, the biology of the *Plasmodium* strains used, and host genetics. As an example, the variety of protective immune mechanisms is reflected by the predominance of T cells in *P. chabaudi* infections[42] and antibodies play a prominent role in *P. yoelii* infectionsv[43]. Among T cells, CD4$^+$ T-cells are known to modulate the function of several effector cells including CD8$^+$ T-cells, macrophages and help B cells for antibody production and altogether participate to the generation of protective responses against *Plasmodium* infection. In the present work, it was striking to observe that mostly CD4$^+$ T-cells and not CD8$^+$ T-cells are key players in the acquisition of protective immunity induced by PbNK65 hrfΔ parasites, with the depletion of CD4$^+$ T-cells but not CD8$^+$ T-cells resulting in a loss of protection. Additional evidence indicates a prominent role of CD4$^+$ T-cells over CD8$^+$ T-cells in protection against blood stage infection. Investigations into the cellular immune responses induced by vaccination with chemically attenuated *P. yoelii* 17× demonstrated the crucial role of CD4$^+$ T-cells after blood-stage parasite challenge, with the depletion of CD4$^+$ T-cells but not CD8$^+$ T-cells resulting in a loss of protection 44. The same group has demonstrated earlier that CD4$^+$ T cell-depleted mice, previously vaccinated with *P. chabaudi* RBCs attenuated with centanamycin, all succumbed, whereas no change in their level of immunity was observed when CD8$^+$ T-cells were depleted from immune mice[38]. From all these studies, it remains unclear why CD4$^+$ but not CD8$^+$ T-cells are selectively associated with protection, although both CD4$^+$ and CD8$^+$ T-cells were equally affected in terms of down-regulation of PD-1 expression by PbNK65 hrfΔ parasites (FIG. 15). It seems that in our system, protective mechanisms are highly dominated by two concerted effector mechanisms, effector CD4 T-cells and antibody producing B cells which ultimately promote CD11b phagocytic activity. Our work is unique in that protective mechanisms elicited by the PbNK65 hrfΔ parasite were examined in detail, exploring all compartments of innate and adaptive immune responses. Since such detailed analysis of effector immune mechanisms are not available for mutants reported by other groups, it cannot be conclusively established whether or not common protective mechanisms are shared among all these mutants. This question remains open until a systematic analysis of various mutants will be examined side by side in one single experimental setting will be performed. It can be anticipated that therapeutic or vaccine interventions in naïve and in individuals with an infection history may implicate distinct physiological states of the host immune system, and therefore different outcomes could occur in terms of resistance or susceptibility to the pathogen or response to vaccination. In the present work, the vaccine efficacy of the PbNK65 hrfΔ parasite was initially demonstrated in naïve mice with no history of infection and may not be the case in mice that have experienced malaria episodes before. To assess whether the mutant parasite was equally effective regardless of infection history, mice were infected with the WT parasite and after the blood stage was established, mice were cured via drug chemoprophylaxis. Once the infection was resolved, mice were then infected with PbNK65 hrfΔ parasites. The pattern of infection followed by the infection resolution was exactly similar between naïve mice and mice that have experienced previous infections, suggesting that previous exposure to WT parasites does not alter fundamental immunological mechanisms associated with protection that are promoted by the mutant parasite. This would suggest that the approach may be efficient even in individuals that have already been infected in natural conditions and who repeatedly received antimalarial drugs.

REFERENCES

1. WHO. World Malaria Report (2015).
2. Gardner, M. J. et al. Genome sequence of the human malaria parasite *Plasmodium falciparum*. Nature 419, 498-511 (2002).
3. Scherf, A., Lopez-Rubio, J. J. & Riviere, L. Antigenic variation in *Plasmodium falciparum*. Annu. Rev. Microbiol. 62, 445-470 (2008).
4. Langhorne, J., Ndungu, F. M., Sponaas, A. M. & Marsh, K. Immunity to malaria: more questions than answers. Nature Immunol. 9, 725-732 (2008).
5. van der Heyde, H. C., Huszar, D., Woodhouse, C., Manning, D. D. & Weidanz, W. P. The resolution of acute malaria in a definitive model of B cell deficiency, the JHD mouse. J. Immunol. 152, 4557-4562 (1994).
6. Janssen, E. M. et al. CD4+ T cells are required for secondary expansion and memory in CD8+ T lymphocytes. Nature 421, 852-856 (2003).
7. Su, Z. & Stevenson, M. M. Central role of endogenous gamma interferon in protective immunity against blood-stage *Plasmodium chabaudi* AS infection. Infect. Immun. 68, 4399-4406 (2000).
8. Xu, W. & Zhang, J. J. Stat1-dependent synergistic activation of T-bet for IgG2a production during early stage of B cell activation. J. Immunol. 175, 7419-7424 (2005).
9. Sponaas, A. M. et al. Migrating monocytes recruited to the spleen play an important role in control of blood stage malaria. Blood 114, 5522-5531 (2009).
10. Waddell, S. J. et al. Dissecting interferon-induced transcriptional programs in human peripheral blood cells. PloS one 5, e9753, doi:10.1371/journal.pone.0009753 (2010).
11. Del Portillo, H. A. et al. The role of the spleen in malaria. Cell Microbiol. 14, 343-355 (2012).
12. Chandele, A., Mukerjee, P., Das, G., Ahmed, R. & Chauhan, V. S. Phenotypic and functional profiling of malaria-induced CD8 and CD4 T cells during blood-stage infection with *Plasmodium yoelii*. Immunology 132, 273-286 (2011).
13. Butler, N. S. et al. Therapeutic blockade of PD-L1 and LAG-3 rapidly clears established blood-stage *Plasmodium* infection. Nature Immunol. 13, 188-195 (2012).
14. Illingworth, J. et al. Chronic exposure to *Plasmodium falciparum* is associated with phenotypic evidence of B and T cell exhaustion. J. Immunol. 190, 1038-1047 (2013).
15. Wykes, M. N., Horne-Debets, J. M., Leow, C. Y. & Karunarathne, D. S. Malaria drives T cells to exhaustion. Front. Microbiol. 5, 249 (2014).
16. Butler, N. S. et al. Superior antimalarial immunity after vaccination with late liver stage-arresting genetically attenuated parasites. Cell host & microbe 9, 451-462 (2011).
17. van Dijk, M. R. et al. Genetically attenuated, P36p-deficient malarial sporozoites induce protective immunity and apoptosis of infected liver cells. Proc. Natl. Acad. Sci. USA 102, 12194-12199 (2005).
18. Mueller, A. K., Labaied, M., Kappe, S. H. & Matuschewski, K. Genetically modified *Plasmodium* parasites as a protective experimental malaria vaccine. Nature 433, 164-167 (2005).
19. Mueller, A. K. et al. *Plasmodium* liver stage developmental arrest by depletion of a protein at the parasite-host interface. Proc. Natl. Acad. Sci. USA 102, 3022-3027 (2005).
20. Ting, L. M., Gissot, M., Coppi, A., Sinnis, P. & Kim, K. Attenuated *Plasmodium yoelii* lacking purine nucleoside phosphorylase confer protective immunity. Nature Med. 14, 954-958 (2008).
21. Aly, A. S., Downie, M. J., Mamoun, C. B. & Kappe, S. H. Subpatent infection with nucleoside transporter 1-deficient *Plasmodium* blood stage parasites confers sterile protection against lethal malaria in mice. Cell. Microbiol. 12, 930-938 (2010).
22. Spaccapelo, R. et al. Plasmepsin 4-deficient *Plasmodium berghei* are virulence attenuated and induce protective immunity against experimental malaria. Am. J. Pathol. 176, 205-217 (2010).
23. Demarta-Gatsi, C. et al. Protection against malaria in mice is induced by blood stage-arresting histamine-releasing factor (HRF)-deficient parasites. J. Exp. Med. 213, 1419-1428 (2016)24. Mathieu, C. et al. *Plasmodium berghei* histamine-releasing factor favours liver-stage development via inhibition of IL-6 production and associates with a severe outcome of disease. Cell. Microbiol. 17, 542-558 (2015).
25. Perlmann, P. & Troye-Blomberg, M. Malaria and the immune system in humans. Chem. Immunol. 80, 229-242 (2002).
26. van der Heyde, H. C., Pepper, B., Batchelder, J., Cigel, F. & Weidanz, W. P. The time course of selected malarial infections in cytokine-deficient mice. Exp. Parasitol. 85, 206-213 (1997).
27. Taylor-Robinson, A. W. A model of development of acquired immunity to malaria in humans living under endemic conditions. Med. Hypotheses 58, 148-156 (2002).
28. Oehen, S. & Brduscha-Riem, K. Differentiation of naive CTL to effector and memory CTL: correlation of effector function with phenotype and cell division. J. Immunol. 161, 5338-5346 (1998).
29. Spring, M. et al. First-in-human evaluation of genetically attenuated *Plasmodium falciparum* sporozoites administered by bite of *Anopheles* mosquitoes to adult volunteers. Vaccine 31, 4975-4983 (2013).
30. Sam, H. & Stevenson, M. M. In vivo IL-12 production and IL-12 receptors beta1 and beta2 mRNA expression in the spleen are differentially up-regulated in resistant B6 and susceptible A/J mice during early blood-stage *Plasmodium* chabaudi AS malaria. J. Immunol. 162, 1582-1589 (1999).
31. Sam, H. & Stevenson, M. M. Early IL-12 p70, but not p40, production by splenic macrophages correlates with host resistance to blood-stage *Plasmodium* chabaudi AS malaria. Clin. Exp. Immunol. 117, 343-349 (1999).
32. Luty, A. J. et al. Low interleukin-12 activity in severe *Plasmodium falciparum* malaria. Infect. Immunol. 68, 3909-3915 (2000).
33. Perkins, D. J., Weinberg, J. B. & Kremsner, P. G. Reduced interleukin-12 and transforming growth factor-beta1 in severe childhood malaria: relationship of cytokine balance with disease severity. J. Infect. Dis. 182, 988-992 (2000).
34. Nish, S. A. et al. T cell-intrinsic role of IL-6 signaling in primary and memory responses. eLife 3, e01949 (2014).
35. Day, C. L. et al. PD-1 expression on HIV-specific T cells is associated with T-cell exhaustion and disease progression. Nature 443, 350-354 (2006).

36. Hofmeyer, K. A., Jeon, H. & Zang, X. The PD-1/PD-L1 (B7-H1) pathway in chronic infection-induced cytotoxic T lymphocyte exhaustion. J. Biomed. Biotechnol. 2011, 451694 (2011).
37. Wherry, E. J. T cell exhaustion. Nature Immunol. 12, 492-499 (2011).
38. Good, M. F. et al. Cross-species malaria immunity induced by chemically attenuated parasites. J. Clin. Invest. 123, 3353-3362 (2013).
39. Bommarito, D., Hall, C., Taams, L. S. & Corrigall, V. M. A2.03 The PD-1/PD-L1 axis is modulated by pro-inflammatory cytokines. Annals Rheum. Dis. 75 (2016).
40. Ryg-Cornejo, V. et al. Severe Malaria Infections Impair Germinal Center Responses by Inhibiting T Follicular Helper Cell Differentiation. Cell Rep. 14, 68-81 (2016).
41. Muramatsu, M. et al. Class switch recombination and hypermutation require activation-induced cytidine deaminase (AID), a potential RNA editing enzyme. Cell 102, 553-563 (2000).
42. Brake, D. A., Weidanz, W. P. & Long, C. A. Antigen-specific, interleukin 2-propagated T lymphocytes confer resistance to a murine malarial parasite, *Plasmodium chabaudi* adami. J. Immunol. 137, 347-352 (1986).
43. Langhorne, J., Gillard, S., Simon, B., Slade, S. & Eichmann, K. Frequencies of CD4+ T cells reactive with *Plasmodium chabaudi* chabaudi: distinct response kinetics for cells with Th1 and Th2 characteristics during infection. Int. Immunol. 1, 416-424 (1989).
44. Raja, A. I. et al. Chemically Attenuated Blood-Stage *Plasmodium yoelii* Parasites Induce Long-Lived and Strain-Transcending Protection. Infect. Immun. 84, 2274-2288 (2016).
45. Crouch, E. E. et al. Regulation of AID expression in the immune response. J. Exp. Med. 204, 1145-1156 (2007).
46. Ghorbal M. et al Genome editing in the human malaria parasite *Plasmodium falciparum* using CRISPR-Cas9 system. Nat Biotechnol. 2014 August; 32 (8):819-21
47 Alaro, J. R., A Partridge, K. Miura, A Diouf, A M. Lopez, E. Angov, C. A. Long, and J. M. Burns, Jr. 2013. A chimeric *Plasmodium falciparum* merozoite surface protein vaccine induces high titers of parasite growth inhibitory antibodies. Infection and immunity 81:3843-3854.
48 Aly, A S., M. J. Downie, C. B. Mamoun, and S. H. Kappe. 2010. Subpatent infection with nucleoside transporter 1-deficient *Plasmodium* blood stage parasites confers sterile protection against lethal malaria in mice. *Cellular microbiology* 12:930-938.
Barton, B. E. 1997. IL-6: insights into novel biological activities. *Clinicat immunology and immunopathology* 85: 16-20.
49 Beghdadi, W., A Porcherie, B. S. Schneider, D. Dubayle, R. Peronet, M. Huerre, T. Watanabe, H. Ohtsu, J. Louis, and S. Mecheri. 2008. Inhibition of histamine-mediated signaling confers significant protection against severe malaria in mouse models of disease. *The Journal of experimental medicine* 205:395-408.
50 Bhisutthibhan, J., M. A. Philbert, H. Fujioka, M. Aikawa, and S. R. Meshnick. 1999. The *Plasmodium falciparum* translationally controlled tumor protein: subcellular localization and calcium binding. *European journal of cell biology* 78:665-670.
51 Bodescot, M., O. Silvie, A Siau, P. Refour, P. Pino, J. F. Franetich, L. Hannoun, R. Sauerwein, and D. Mazier. 2004. Transcription status of vaccine candidate genes of *Plasmodium falciparum* during the hepatic phase of its life cycle. *Parasitology research* 92:449-452.

52 Coutelier, J. P., J. T. van der Logt, F. W. Heessen, G. Warnier, and J. Van Snick. 1987. IgG2a restriction of murine antibodies elicited by viral infections. *The Journal of experimental medicine* 165:64-69.
53 de Koning-Ward, T. F., D. A. Fidock, V. Thathy, R. Menard, R. M. van Spaendonk, A. P. Waters, and C. J. Janse. 2000. The selectable marker human dihydrofolate reductase enables sequential genetic manipulation of the *Plasmodium berghei* genome. *Molecular and biochemical parasitology* 106:199-212.
54 Janse, C. J., J. Ramesar, and A. P. Waters. 2006. High-efficiency transfection and drug selection of genetically transformed blood stages of the rodent malaria parasite *Plasmodium berghei*. *Nature protocols* 1:346-356.
55 Jung, S., D. Unutmaz, P. Wong, G. Sano, K. De los Santos, T. Sparwasser, S. Wu, S. Vuthoori, K. Ko, F. Zavala, E. G. Pamer, D. R. Littman, and R A Lang. 2002. In vivo depletion of CDI le+ dendritic cells abrogates priming of CD8+ T cells by exogenous cell-associated antigens. *Immunity* 17:211-220.
56 Kishimoto, T., S. Akira, and T. Taga. 1992. Interleukin-6 and its receptor: a paradigm for cytokines. *Science* (New York, N Y) 258:593-597.
57 Mathieu, C., C. Demarta-Gatsi, A Porcherie, S. Brega, S. Thiberge, K. Ronce, L. Smith, R. Peronet, R. Amino, R. Menard, and S. Mecheri. 2015. *Plasmodium berghei* histamine-releasing factor favours liver-stage development via inhibition of IL-6 production and associates with a severe outcome of disease. *Cellular microbiology* 17:542-558.
58 Miyagami, T., 1. Igarshi, and M. Suzuki. 1987. *Plasmodium berghei*: long lasting immunity induced by a permanent attenuated mutant. Zentralblatt fur Bakteriologie, Mikrobiologie, und Hygiene. Series A, Medical microbiology, infectious diseases, virology, parasitology 264: 502-512.
59 Ndungu, F. M., E. T. Cadman, J. Coulcher, E. Nduati, E. Couper, D. W. Macdonald, D. Ng, and J. Langhorne. 2009. Functional memory B cells and long-lived plasma cells are generated after a single *Plasmodium* chabaudi infection in mice. *PLoS pathogens* 5:el 000690.
60 Nimmerjahn, F., and J. V. Ravetch. 2005. Divergent immunoglobulin g subclass activity through selective Fc receptor binding. *Science* (New York, N Y) 310: 1510-1512.
61 Pied, S., L. Renia, A Nussler, F. Miltgen, and D. Mazier. 1991. Inhibitory activity of IL-6 on malaria hepatic stages. *Parasite immunology* 13:211-217.
62 Pombo, D. J., G. Lawrence, C. Hirunpetcharat, C. Rzepczyk, M. Bryden, N. Cloonan, K. Anderson, Y. Mahakunkijcharoen, L. B. Martin, D. Wilson, S. Elliott, S. Elliott, D. P. Eisen, J. B. Weinberg, A. Saul, and M. F. Good. 2002. Immunity to malaria after administration of ultra-low doses of red cells infected with *Plasmodium falciparum*. *The Lancet* 360:610-617.
63 Puga, 1., M. Cols, C. M. Barra, B. He, L. Cassis, M. Gentile, L. Comerma, A. Chorny, M. Shan, W. Xu, G. Magri, D. M. Knowles, W. Tarn, A. Chiu, J. B. Bussel, S. Serrano, J. A. Lorente, B. Bellosillo, J. Lloreta, N. Juanpere, F. Alameda, T. Barn, C. D. de Heredia, N. Toran, A. Catala, M. Torrebadell, C. Fortuny, V. Cusi, C. Carreras, G. A. Diaz, J. M. Blander, C. M. Farber, G. Silvestri, C. Cunningham-Rundles, M. Calvillo, C. Dufour, L. D. Notarangelo, V. Lougaris, A. Plebani, J. L. Casanova, S. C. Ganal, A. Diefenbach, J. I. Arostegui, M. Juan, J. Yague, N. Mahlaoui, J. Donadieu, K. Chen, and A. Cerutti. 2012. B cell-helper neutrophils stimulate the diversification and production of immunoglobulin in the marginal zone of the spleen. *Nature immunology* 13:170-180.
64 Putrianti, E. D., A. Schmidt-Christensen, 1. Arnold, V. T. Heussler, K. Matuschewski, and O. Silvie. 2010. The *Plasmodium* serine-type SERA proteases display distinct expression patterns and non-essential in vivo roles during life cycle progression of the malaria parasite. *Cellular microbiology* 12:725-739.
65 Spaccapelo, R., E. Aime, S. Caterbi, P. Arcidiacono, B. Capuccini, M. Di Cristina, T. Dottorini, M. Rende, F. Bistoni, and A. Crisanti. 2011. Disruption of plasmepsin-4 and merozoites surface protein-7 genes in *Plasmodium berghei* induces combined virulence-attenuated phenotype. *Scientific reports* 1:39.
66 Spaccapelo, R., C. J. Janse, S. Caterbi, B. Franke-Fayard, J. A. Bonilla, L. M. Syphard, M. Di Cristina, T. Dottorini, A. Savarino, A. Cassone, F. Bistoni, A. P. Waters, J. B. Dame, and A. Crisanti. 2010. Plasmepsin 4-deficient *Plasmodium berghei* are virulence attenuated and induce protective immunity against experimental malaria. *The American journal of pathology* 176:205-217.
67 Ting, L. M., M. Gissot, A Coppi, P. Sinnis, and K. Kim. 2008. Attenuated *Plasmodium yoelii* lacking purine nucleoside phosphorylase confer protective immunity. Nature medicine 14:954-958.
68 Waki, S., J. Tamura, M. Imanaka, S. Ishikawa, and M. Suzuki. 1982. *Plasmodium berghei*: isolation and maintenance of an irradiation attenuated strain in the nude mouse. *Experimental parasitology* 53:335-340.
69 Wykes, M. N., Y. H. Zhou, X. Q. Liu, and M. F. Good. 2005. *Plasmodium yoelii* can ablate vaccine-induced long-term protection in mice. *Journal of immunology* (Baltimore, Md.: 1950) 175:2510-2516.
70. Thathy and Ménard, Gene targeting in *Plasmodium berghei Methods Mol Med* 2002; 72:317-31.
71. McRobert and McConkey, 2002 RNA interference (RNAi) inhibits growth of *Plasmodium falciparum Mol Biochem Parasitol*, 2002 February; 119(2):273-8
72. Mohmmed et al. RNA interference: biology, mechanism, and applications *Microbiol Mol Biol Rev.* 2003 December; 67(4):657-85.
73. Gissot et al., PfMybl, a *Plasmodium falciparum* Transcription Factor, Is Required for Intra-Erythrocytic Growth and Controls Key Genes for Cell Cycle Regulation *J Mol Biol* 346 (1), 29-42. 2004 Dec. 21.
74. Leef et al. BULL WORLD HEALTH ORGAN vol. 57, no. 1, 1979, pages 87-91
75. Orjih et al. J TROP MED HYG. vol. 29, no. 3, Mai 1980, pages 343-7
76. Trager; Jensen SCIENCE vol. 193, 1976, pages 673-5

The invention claimed is:

1. An immunogenic composition, comprising at least $10^3$ genetically modified live *Plasmodium falciparum*, wherein the histamine releasing factor (HRF) protein coding sequence is deleted in the genome of the genetically modified live *Plasmodium*, and a pharmaceutically acceptable excipient and/or support;
wherein when administered to a primate the genetically modified live *Plasmodium* develop in the primate and do not produce functional histamine releasing factor (HRF) protein, thereby inducing an antibody and cellular immune response against the *Plasmodium falciparum* in the primate.

2. The immunogenic composition of claim 1, wherein the genetically modified live *Plasmodium* does not produce a functional form of one or more of purine nucleoside phosphorylase, nucleoside transporter 1, UIS3, UIS4, p52, p36, and HMGB2.

3. The immunogenic composition of claim 1, wherein the HMGB2 coding sequence is deleted in the genome of the genetically modified live *Plasmodium*.

4. The immunogenic composition of claim 1, wherein the genetically modified live *Plasmodium* is in the form of intra-erythrocytic trophozoites, merozoites or schizonts.

5. The immunogenic composition of claim 1, wherein the genetically modified live *Plasmodium* is in the form of sporozoites.

6. The immunogenic composition of claim 1, wherein the composition is formulated for administration of a dose of at least $10^4$ of the genetically modified live *Plasmodium* to a primate.

7. The immunogenic composition of claim 1, wherein the composition is formulated for administration of a dose of at least $10^5$ of the genetically modified live *Plasmodium* to a primate.

8. The immunogenic composition of claim 1, wherein when administered to a primate the composition does not cause cerebral malaria.

9. The immunogenic composition of claim 1, wherein the antibody response comprises an IgG3 and IgG1 antibody response.

10. The immunogenic composition of claim 1, wherein the cellular immune response comprises an FcγR+CD 11b+ phagocytic cellular immune response.

11. The immunogenic composition of claim 1, wherein when administered to a primate the composition induces an increase of at least 50% in plasma IL-6 in the primate.

12. The immunogenic composition of claim 1, herein when administered to a primate the composition induces a decrease of at least 50% in spleen PD 1+ T cells.

13. The immunogenic composition of claim 1, wherein the primate is a human.

14. The immunogenic composition of claim 1, wherein the composition comprises an immunological adjuvant selected from muramyl peptide type adjuvants, trehalose dimycolate (TDM), lipopolysaccharide (LPS), monophosphoryl lipid A (MPL), carboxymethylcellulose, complete Freund's adjuvant, incomplete Freund's adjuvant, adjuvants of "oil-in-water" emulsion type optionally supplemented with squalene or squalane, mineral adjuvants, bacterial toxins, CpG oligodeoxynucleotides, saponins, synthetic copolymers, cytokines, imidazoquinolones, and combinations thereof.

15. A process of preparing the immunogenic composition according to claim 1, comprising admixing the genetically modified live *Plasmodium* with the at least one pharmaceutically acceptable excipient and/or support.

\* \* \* \* \*

SEQUENCE LISTING

```
<160> NUMBER OF SEQ ID NOS: 34

<210> SEQ ID NO 1
<211> LENGTH: 24
<212> TYPE: DNA
<213> ORGANISM: Artificial Sequence
<220> FEATURE:
<223> OTHER INFORMATION: Pb 18S

<400> SEQUENCE: 1
attaatcttg aacgaggaat ggct                                            24

<210> SEQ ID NO 2
<211> LENGTH: 19
<212> TYPE: DNA
<213> ORGANISM: Artificial Sequence
<220> FEATURE:
<223> OTHER INFORMATION: Pb 18S

<400> SEQUENCE: 2
tcaatcggta ggagcgacg                                                  19

<210> SEQ ID NO 3
<211> LENGTH: 20
<212> TYPE: DNA
<213> ORGANISM: Artificial Sequence
<220> FEATURE:
<223> OTHER INFORMATION: Pb LSP2

<400> SEQUENCE: 3
gccaaatgct aaacctaatg                                                 20

<210> SEQ ID NO 4
<211> LENGTH: 20
<212> TYPE: DNA
<213> ORGANISM: Artificial Sequence
<220> FEATURE:
<223> OTHER INFORMATION: Pb LSP2
```

```
<400> SEQUENCE: 4
tgggtttgta ttgtatgcac                                              20

<210> SEQ ID NO 5
<211> LENGTH: 17
<212> TYPE: DNA
<213> ORGANISM: Artificial Sequence
<220> FEATURE:
<223> OTHER INFORMATION: Pb HSP70

<400> SEQUENCE: 5
tgcagctaat caaactc                                                 17

<210> SEQ ID NO 6
<211> LENGTH: 20
<212> TYPE: DNA
<213> ORGANISM: Artificial Sequence
<220> FEATURE:
<223> OTHER INFORMATION: Pb HSP70

<400> SEQUENCE: 6
acttcaattt gtggaacacc                                              20

<210> SEQ ID NO 7
<211> LENGTH: 22
<212> TYPE: DNA
<213> ORGANISM: Artificial Sequence
<220> FEATURE:
<223> OTHER INFORMATION: mu IL-23

<400> SEQUENCE: 7
ccaccaggac tcaaggacaa ca                                           22

<210> SEQ ID NO 8
<211> LENGTH: 19
<212> TYPE: DNA
<213> ORGANISM: Artificial Sequence
<220> FEATURE:
<223> OTHER INFORMATION: mu IL-23

<400> SEQUENCE: 8
gcaggctccc ctttgaaga                                               19

<210> SEQ ID NO 9
<211> LENGTH: 21
<212> TYPE: DNA
<213> ORGANISM: Artificial Sequence
<220> FEATURE:
<223> OTHER INFORMATION: mu EBI3

<400> SEQUENCE: 9
cagagtgcaa tgccatgctc c                                            21

<210> SEQ ID NO 10
<211> LENGTH: 20
<212> TYPE: DNA
<213> ORGANISM: Artificial Sequence
<220> FEATURE:
<223> OTHER INFORMATION: mu EBI3

<400> SEQUENCE: 10
gccacaccga gcctgtaagt                                              20

<210> SEQ ID NO 11
<211> LENGTH: 29
```

```
<212> TYPE: DNA
<213> ORGANISM: Artificial Sequence
<220> FEATURE:
<223> OTHER INFORMATION: mu IL-12p35

<400> SEQUENCE: 11
tactagagag acttcttcca caacaagag                                           29

<210> SEQ ID NO 12
<211> LENGTH: 22
<212> TYPE: DNA
<213> ORGANISM: Artificial Sequence
<220> FEATURE:
<223> OTHER INFORMATION: mu IL-12p35

<400> SEQUENCE: 12
gattctgaag tgctgcgttg at                                                  22

<210> SEQ ID NO 13
<211> LENGTH: 20
<212> TYPE: DNA
<213> ORGANISM: Artificial Sequence
<220> FEATURE:
<223> OTHER INFORMATION: mu IL-12p40

<400> SEQUENCE: 13
ggaagcacgg cagcagaata                                                     20

<210> SEQ ID NO 14
<211> LENGTH: 24
<212> TYPE: DNA
<213> ORGANISM: Artificial Sequence
<220> FEATURE:
<223> OTHER INFORMATION: mu IL-12p40

<400> SEQUENCE: 14
aacttgaggg agaagtagga atgg                                                24

<210> SEQ ID NO 15
<211> LENGTH: 24
<212> TYPE: DNA
<213> ORGANISM: Artificial Sequence
<220> FEATURE:
<223> OTHER INFORMATION: mu IFN-gamma

<400> SEQUENCE: 15
aaaggatgca ttcatgagta ttgc                                                24

<210> SEQ ID NO 16
<211> LENGTH: 19
<212> TYPE: DNA
<213> ORGANISM: Artificial Sequence
<220> FEATURE:
<223> OTHER INFORMATION: mu IFN-gamma

<400> SEQUENCE: 16
cgcttcctga ggctggatt                                                      19

<210> SEQ ID NO 17
<211> LENGTH: 25
<212> TYPE: DNA
<213> ORGANISM: Artificial Sequence
<220> FEATURE:
<223> OTHER INFORMATION: mu IL-6

<400> SEQUENCE: 17
```
aaagaaatga tggatgctac caaac                                          25

<210> SEQ ID NO 18
<211> LENGTH: 33
<212> TYPE: DNA
<213> ORGANISM: Artificial Sequence
<220> FEATURE:
<223> OTHER INFORMATION: mu IL-6

<400> SEQUENCE: 18
cttgttatct tttaagttgt tcttcatgta ctc                                 33

<210> SEQ ID NO 19
<211> LENGTH: 20
<212> TYPE: DNA
<213> ORGANISM: Artificial Sequence
<220> FEATURE:
<223> OTHER INFORMATION: mu IL-10

<400> SEQUENCE: 19
ggcgctgtca tcgatttctc                                                20

<210> SEQ ID NO 20
<211> LENGTH: 26
<212> TYPE: DNA
<213> ORGANISM: Artificial Sequence
<220> FEATURE:
<223> OTHER INFORMATION: mu IL-10

<400> SEQUENCE: 20
gacaccttgg tcttggagct tattaa                                         26

<210> SEQ ID NO 21
<211> LENGTH: 20
<212> TYPE: DNA
<213> ORGANISM: Artificial Sequence
<220> FEATURE:
<223> OTHER INFORMATION: mu HPRT

<400> SEQUENCE: 21
ctggtgaaaa ggacctctcg                                                20

<210> SEQ ID NO 22
<211> LENGTH: 26
<212> TYPE: DNA
<213> ORGANISM: Artificial Sequence
<220> FEATURE:
<223> OTHER INFORMATION: mu HPRT

<400> SEQUENCE: 22
tgaagtactc attatagtca agggca                                         26

<210> SEQ ID NO 23
<211> LENGTH: 25
<212> TYPE: DNA
<213> ORGANISM: Artificial Sequence
<220> FEATURE:
<223> OTHER INFORMATION: mu TNF-alpha

<400> SEQUENCE: 23
catcttctca aaattcgagt gacaa                                          25

<210> SEQ ID NO 24
<211> LENGTH: 23
<212> TYPE: DNA
<213> ORGANISM: Artificial Sequence
<220> FEATURE:
<223> OTHER INFORMATION: mu TNF-alpha

<400> SEQUENCE: 24
tgggagtaga caaggtacaa ccc                                                 23

<210> SEQ ID NO 25
<211> LENGTH: 29
<212> TYPE: DNA
<213> ORGANISM: Artificial Sequence
<220> FEATURE:
<223> OTHER INFORMATION: ApaI-5'UTR-PbHRF-F (a)

<400> SEQUENCE: 25
cgcgggcccg cgcattatta ccgttgtca                                           29

<210> SEQ ID NO 26
<211> LENGTH: 31
<212> TYPE: DNA
<213> ORGANISM: Artificial Sequence
<220> FEATURE:
<223> OTHER INFORMATION: PstI-5'UTR-PbHRF-R

<400> SEQUENCE: 26
cgcctgcagg gcttatgcaa gtatcgaaca a                                        31

<210> SEQ ID NO 27
<211> LENGTH: 30
<212> TYPE: DNA
<213> ORGANISM: Artificial Sequence
<220> FEATURE:
<223> OTHER INFORMATION: KpnI-3'UTR-PbHRF-F

<400> SEQUENCE: 27
cgcggtacct tgctacatga cgcataaacc                                          30

<210> SEQ ID NO 28
<211> LENGTH: 31
<212> TYPE: DNA
<213> ORGANISM: Artificial Sequence
<220> FEATURE:
<223> OTHER INFORMATION: EcoRI-3'UTR-PbHRF-R (a')

<400> SEQUENCE: 28
cgcgaattct gtgaaatcga caatgttttg g                                        31

<210> SEQ ID NO 29
<211> LENGTH: 24
<212> TYPE: DNA
<213> ORGANISM: Artificial Sequence
<220> FEATURE:
<223> OTHER INFORMATION: HRF5'-F (b)

<400> SEQUENCE: 29
gcgatacaaa caaatttatt cagc                                                24

<210> SEQ ID NO 30
<211> LENGTH: 22
<212> TYPE: DNA
<213> ORGANISM: Artificial Sequence
<220> FEATURE:
<223> OTHER INFORMATION: HRF3'-R (c')

<400> SEQUENCE: 30
cgcaagatat cagagctttt ca                                                  22

```
<210> SEQ ID NO 31
<211> LENGTH: 32
<212> TYPE: DNA
<213> ORGANISM: Artificial Sequence
<220> FEATURE:
<223> OTHER INFORMATION: hDHFR 3'-F (c)

<400> SEQUENCE: 31
tgttgtctct tcaatgattc ataaatagtt gg                                    32

<210> SEQ ID NO 32
<211> LENGTH: 26
<212> TYPE: DNA
<213> ORGANISM: Artificial Sequence
<220> FEATURE:
<223> OTHER INFORMATION: hDHFR 5'-R (b')

<400> SEQUENCE: 32
tgctttgagg ggtgagcatt taaagc                                           26

<210> SEQ ID NO 33
<211> LENGTH: 19
<212> TYPE: DNA
<213> ORGANISM: Artificial Sequence
<220> FEATURE:
<223> OTHER INFORMATION: PbHRF -5' orf-F

<400> SEQUENCE: 33
ccatttggaa atgcggaat                                                   19

<210> SEQ ID NO 34
<211> LENGTH: 24
<212> TYPE: DNA
<213> ORGANISM: Artificial Sequence
<220> FEATURE:
<223> OTHER INFORMATION: PbHRF -3 'orf-R

<400> SEQUENCE: 34
tttttcttca aataaaccat ctga                                             24
```